US009376702B2

(12) United States Patent
Polle et al.

(10) Patent No.: US 9,376,702 B2
(45) Date of Patent: Jun. 28, 2016

(54) REGULATING THE PRODUCTION OF ISOPRENOIDS IN ALGAL CELLS

(75) Inventors: Juergen Polle, Brooklyn, NY (US); Duc Tran, Brooklyn, NY (US)

(73) Assignee: The City University of New York, New York, NY (US)

( * ) Notice: Subject to any disclaimer, the term of this patent is extended or adjusted under 35 U.S.C. 154(b) by 817 days.

(21) Appl. No.: 12/989,189

(22) PCT Filed: Apr. 24, 2009

(86) PCT No.: PCT/US2009/041687
§ 371 (c)(1), (2), (4) Date: Sep. 29, 2011

(87) PCT Pub. No.: WO2009/132286
PCT Pub. Date: Oct. 29, 2009

(65) Prior Publication Data

US 2012/0052584 A1 Mar. 1, 2012

Related U.S. Application Data

(60) Provisional application No. 61/125,434, filed on Apr. 24, 2008.

(51) Int. Cl.

| | |
|---|---|
| ***C12P 23/00*** | (2006.01) |
| ***C12N 9/02*** | (2006.01) |
| ***C12N 1/12*** | (2006.01) |
| ***C12N 15/85*** | (2006.01) |

(52) U.S. Cl.
CPC . *C12P 23/00* (2013.01); *C12N 1/12* (2013.01); *C12N 15/85* (2013.01); *C12N 9/0004* (2013.01)

(58) Field of Classification Search
CPC ........... C12P 7/065; C12P 5/007; C12P 23/00
See application file for complete search history.

(56) References Cited

U.S. PATENT DOCUMENTS

| | | | | |
|---|---|---|---|---|
| 6,929,928 | B2 | 8/2005 | Cheng et al. | |
| 2006/0194274 | A1 | 8/2006 | Flachmann et al. | |
| 2007/0269864 | A1 | 11/2007 | Lee | |
| 2011/0008861 | A1 * | 1/2011 | Berry et al. | 435/161 |

OTHER PUBLICATIONS

Kucho et al., "Cis-acting Elements and DNA-Binding Proteins Involved in CO2-responsive Transcriptional Activation of Cah1 encoding a Periplasmic Carbonic Anhydrase in Chlamydomonas Reinhardtii", Plant Physiol. vol. 133, No. 2, pp. 783-793 (2003).
FC099850.1—CACW26995.fwd CACW Chlamydomonas Reinhardtii Strain S1D2 Normal Chlamydomonas Reinhardtii cDNA Clone CACW26995 5-, mRNA sequence. NCBI (online) 6 URL:<http://www.ncbi.nlm.nih.gov/nucest/161810024>.
Lee W. Young, International Search Report for corresponding PCT Application No. PCT/US09/41687 filed Apr. 24, 2009, pp. 1-6, Sep. 23, 2009.

* cited by examiner

*Primary Examiner* — Addison D Ault
(74) *Attorney, Agent, or Firm* — Hoffmann & Baron, LLP

(57) ABSTRACT

The invention relates to a method for increasing the production level of isoprenoids in an algal cell. The method includes increasing expression of a polynucleotide sequence that encodes 4-hydroxy-3-methylbut-2-enyl diphosphate reductase (IDS) in the algal cell. In another aspect, the invention relates to a method for increasing the production level of carotenoids in an algal cell. The method includes increasing expression of polynucleotide sequence that encodes phytoene desaturases (PDS) in the algal cell. In a further aspect, the invention relates to an algal cell having a polynucleotide sequence that is genetically engineered to express a higher level of IDS or PDS than a corresponding wild type algal cell, wherein the cell produces an increased level of isoprenoids or carotenoids, respectively, than a corresponding wild type algal cell.

7 Claims, 19 Drawing Sheets

Fig. 5

ATTTAAAGGTGAAAGCACTCATCGTCATTCGAAGTGATGATGTTGTCCAACAGCT
TCAACAAGAGCGCGATTGGTGCAGGCCTCCCAACCGCTCAATCACAGCCCGTCTA
CCGAGTGCCAAGCCGAACCGGCCTGCGCGTGAGGGCAACTGTGGCTGATGAGAC
AGCAGCCACGCAGCAGCAGCAGGAGGAGGAGCGTGGTCGCGAAATTCGCCGGTC
CCTTAACAAGACGGGCCGCTACGTCCGGACTGTCAAAAACGACCCCGACGCGAC
CAAGGCGCTGGATGCAGACGGCGTGGGCTACTCGCTGACCGGGCTCGTGGCGCA
GATGCGGGAGGAGGGCAACTTTTGGAAGCAGGGCGATGTGACCGTCAAGCTGGC
CAAGGCATACGGCTACTGCTGGGGCGTGGAGCGAGCCGTGCGCATGGCTTACGA
GGCGCGCAGGGCGTTCCCAGGCCGCTCCATCCATGTTACCAACGAAATCATCCAC
AACCCGGAAGTGAACAGGCGCCTGCGCGAAATGGATGTGAACATTGTGAAGGAG
GACCCCCAAAAGGGCAAGGACTACAGCAAGATTGACAATGGGGATGTTGTCATC
TTCCCTGCTTTTGGGGTGGGCGCGCCTGACATGAAGTACTTCCGGGACAAGGGCG
TGAACATTGTGGACACTACTTGCCCTTGGGTGGCCAAGGTGTGGAACTCCGTTGA
CACCTATGCCAAGAAAAAGTGCACCTCAATCATCCATGGCAAGTACTCGCACGA
GGAGACTGTGGCCACCGCTTCCTTTGCTGAGGACTACCTGATCATCAAGGACCTC
AATGAAGCACAGTATGTGTGTGACTACATCCTGAAGGGCGGCGACCGAGAGGAG
TTCATGAAGAAGTTCTCCAAGGCCGTCTCCAAGGGCTTTGACCCTGATGTCCACC
TCAACCGCGTGGGCCTGGCCAACCAGACGACCATGCTCAAGGGTGAGACCCAGG
CCATCGGCAAGATGCTGGAGCGCACCATGATGGAGAAATTTGGGCCTCAGAATC
TCCAGGACCACTTCATGGTCATGGACACCATCTGCGATGCCACTCAGGAACGCCA
AGATGCGCTGTACGAGATCACTGATGACCCTACTATTGACATGATGCTTGTGGTG
GGCGGCTTCAACTCTTCCAACACCAGCCACCTACAGGAAATCCCCCACAATAAG
GGCCTGCCTGCATTCTGGGTGGACACTGCCGACCGCATTGACATGGCCAACAACT
CCATTGCGCACAAGCTGCACTACGGGGAGCTCAAGGTGACGgAGAACTgGCTGCC
CGAGGGCCCCATCACCATTGGCGTTACTAGCGGGGCTTCCACACCCGATCGAGCG
GTGGAGGAGGTGCTTGAGCGCGTGTTCCGCATGAAGGATCCCAACTTCAAGGGT
ATCCAGcCTAGGGAATGTGCGCCCCCCGTCCTGCCCACCCACTAAGCACTTGCAG
TCTGTGGCTTGGCCAATGCAGCTGCAATAAGCAAGTATGGCCAGCTGATATGTGA
GTGCCCTGAGGGTTTGCCCTGCAATGGGTGCTCTTGCGTTTCAAGGTCGAGGCCT
TTCATCCTGGGGCTTGAAGCTCAGGTGGGGAGTCTCACCAAACAGCTTGGTCATA
CTAGAATGAAGCCCCTCGCCGTGGTCCTCTTACCAAGCCTGCGCATTTGTACATG
TACTTTCGTATTATTGAATCAATTGTACACGGATTAGATCAGGATATTCCAACCG
GRAAAAACTTCAATGGTGAGCGGGTAGGAGAAATGAGGGAGCAAGGAGTGTGTT
TGGGATTTTTTGTCTCTTCGGTCTGTGATGAAGCAGGTCCAAAGTCATGAGTGGG
AAAACATCCATAATGTTTTACAACACGTTGGCCTTGCCAGTTTTGTACCATAATTT
TGTGTTTTCCTTCACCTTGCTTTGCTAATCTAATCCACTTGCCAACATTTGCCACA
AACATTGGCACAAAATGCAGTGGAATCATTGTTATTGCTTAAATCTGGGAGCTAA
GCTCCTATAACTT (SEQ ID NO: 1)

Fig. 6

MMLSNSFNKSAIGAGLPTAQSQPVYRVPSRTGLRVRATVADETAATQQQQEEER
GREIRRSLNKTGRYVRTVKNDPDATKALDADGVGYSLTGLVAQMREEGNFWKQGD
VTVKLAKAYGYCWGVERAVRMAYEARRAFPGRSIHVTNEIIHNPEVNRRLREMDV
NIVKEDPQKGKDYSKIDNGDVVIFPAFGVGAPDMKYFRDKGVNIVDTTCPWVAKV
WNSVDTYAKKKCTSIIHGKYSHEETVATASFAEDYLIIKDLNEAQYVCDYILKGGDR
EEFMKKFSKAVSKGFDPDVHLNRVGLANQTTMLKGETQAIGKMLERTMMEKFGPQ
NLQDHFMVMDTICDATQERQDALYEITDDPTIDMMLVVGGFNSSNTSHLQEIPHNK
GLPAFWVDTADRIDMANNSIAHKLHYGELKVTENWLPEGPITIGVTSGASTPDRAVE
EVLERVFRMKDPNFKGIQPRECAPPVLPTH (SEQ ID NO: 3)

Fig. 7

ATGCAGACCATGCAGGGCAGGGCACATGCTCAGACACTCAACAGACAGCCTGTT
ACCCAGGTTGCCGGGCGCACCCAGAGGCGGGTTGGCAGGTCTCGCTTGCAAGTG
TATGCTAGGGATTTCCCTCCTCCTCAGTTCGATGGCACTGCGTCGTACCAAGATG
CTGTGGCCCTGTCCACAAAGCTGCAAAATGCACCTCGGCCCGCCAAGCCTCAACG
CGTCGTGATCGCCGGAGCCGGCCTGGCTGGCCTGTCCGCAGCCAAGTACCTGTCC
GATGCTGGCCACATCCCCATCGTGTTGGAGGCCCGCGATGTGCTGGGGGGCAAG
GTGGCTGCATGGAAGGATGAGGATGGAGACTGGTACGAGACTGGCTTGCACATC
TTCTTTGGTGCATACCCCAACATCCAGAGGCTATTTAAGGAGCTCAACATCTCTG
ACAGGCTGCAGTGGAAGAGCCACTCAATGATCTTTGCCATGCAAGACAAGCCTG
GACAGTTCTCACGCTTTGAGTTCCCAGACATCCCTGCCCCCTGGAATGGTGTTGT
CGCCATCCTGCGCAATAACGAGATGTTGTCTTGGACTGAGAAGATTAAGTTTGCC
ATTGGCCTCCTGCCTGCCATCATCTTCGGCCAAAAGTATGTGGAGGAGCAGgATG
AGCTAACAGTAACCCAGTGGATGGAGAAGCAGGGTGTTCCTAGCCGAGTGAACG
ACGAGGTCTTCATTGCCATGGCGaAGGCCCTGAACTTCATCGACCCTGATGAGCT
TTCTATGACCGTTGTGCTAACAGCACTGAACCGTTTCCTGCAAGAGCGACATGGT
AGCAAGATGGCCTTCCTTGATGGTGCTCCCCCAGAGCGGTTGTGCGAACCAATGG
TGAACTACTTCACTTCCAGGGGCGGAGAGCTGAGGATGAATGCACGCCTCAAGC
AAATTGTGCTGAATGAGGACAACAGTGTCAAGCACTTTGAGCTGCTGAATGGAG
AGATTGTTGAGGGAGATGCCTACATGTCCGCTATGCCAGTGGACATCATGAAGA
AGCTGATGCCCCAGCCCTGGAAGAATGTTCCCTTCTTCCAGAAGTTGAATGGCCT
TGAAgGGGTGCCAGTTATCAACATCCACATCTGGTTTGACCGCAAGCTGTCCACA
GTGGACCACCTGCTCTtCTCGCGCTCTGAGTTGCTCAGTGTGTATGCCGACATGAG
CACCACCTGTAAAGAGTACTCAGATGACAAGGCCAGCATGCTTGAGCTGGTGTTT
GCACCTGCTGCCGACTGGATTGGCAGGCCAGATTCAGAGATCGTGGACGCAACC
ATGAAGGAGCTCGAAAAGCTGTTCCCCAACGAGATCAAGGCTGACCAGTCACTG
GCCAAGATCCGCAAATCCAAGGTCATCAAGACACCCCTCTCGGTCTACAAGTCCA
CAGCTGGACGAGAGAAGTACAGGCCCAGCCAAAAGACTCCCATCCCCAACTTCT
AcCTGGCGGGTGACTACACCAAGCAGAAGTACTTGGCATCTATGGAGGGTGCTGT
CTTCAGTGGCAAGCTGGCTTGCGAGCAGGTGGTAGATGATGCTGTCATGCGCGTC
GGCCAGCAGAGCACTGCCCCTAGCCAGcCTGCTCTGGCTGCTGcCTCTGCTGCTGT
GCTGCTGGCCATGGGCGCAGCGCTTGCGGGCAATGCATCTGCCCAGGTCCTGACA
GAGACCATCTGGGGCTCCCCAGTGTTGACCGAGGCAGTCACCTTCCCTTGGTTCT
AA
(SEQ ID NO: 2)

Fig. 8

MQTMQGRAHAQTLNRQPVTQVAGRTQRRVGRSRLQVYARDFPPPQFDGTASYQD
AVALSTKLQNAPRPAKPQRVVIAGAGLAGLSAAKYLSDAGHIPIVLEARDVLGGKV
AAWKDEDGDWYETGLHIFFGAYPNIQRLFKELNISDRLQWKSHSMIFAMQDKPGQF
SRFEFPDIPAPWNGVVAILRNNEMLSWTEKIKFAIGLLPAIIFGQKYVEEQDELTVTQ
WMEKQGVPSRVNDEVFIAMAKALNFIDPDELSMTVVLTALNRFLQERHGSKMAFLD
GAPPERLCEPMVNYFTSRGGELRMNARLKQIVLNEDNSVKHFELLNGEIVEGDAYM
SAMPVDIMKKLMPQPWKNVPFFQKLNGLEGVPVINIHIWFDRKLSTVDHLLFSRSEL
LSVYADMSTTCKEYSDDKASMLELVFAPAADWIGRPDSEIVDATMKELEKLFPNEIK
ADQSLAKIRKSKVIKTPLSVYKSTAGREKYRPSQKTPIPNFYLAGDYTKQKYLASME
GAVFSGKLACEQVVDDAVMRVGQQSTAPSQPALAAASAAVLLAMGAALAGNASA
QVLTETIWGSPVLTEAVTFPWF (SEQ ID NO: 4)

Fig. 9A

IDS/HDr protein sequences from the Joint Genome Institute

Aureococcus
>e_gw1.9.78.1 [Auran1:26431]
MLSEMKSEMLDKMRESNYEVTRGEGNGAVTFTLAKEYGMCWGAERSIEIALAATE
KFGDKQLHITNELLHNPGVNKMLEDEGVSFIEKTGDGGKRFDDVKEGDVVILPAFGA
TLAEMQHFSDMGVTTVDTTCPWVTKVWNVVDKQVQRSMTTIIHGKYAHEEAIATA
SMCDDYLMVKNIDEAEYVCNYMLNPTPEGREDLLHKFAKAMSKGFDPDVHLEKIGI
ANQTTMYKKETQAVGRLFEQVILKKYPDEAADRFVAFDTICSATQERQDAIHEMVD
DESVKDLDFILVVGGFDSSNTAHLVEIPYEAGIPVFHINEADCISETNAVSHRLVSGEM
AVEENWLPTDRPARIGVTSGASTPDAYVQEALERLVLLKSVISTDAAPAAPAEKWA
WSGPVF* (SEQ ID NO: 5)

Chlamydomonas reinhardtii
>estExt_GenewiseH_1.C_640019 [Chlre3:59822]
MQVFANRQASGFKARAERPSRISRVLVPVVHAVAAETKQVGPDGRTLRRSLNQTGR
YVRQPTNDPASQVKMDEHGVGYSTSGLVAQMRTQNNLWKEGDVTVKLAKAYGYC
WGVERAVRMAYEARLAHPDKKVFVTNEIIHNPEVNSRLKEMNIEIVEDEGKGKDYS
MIGGGDVVIFPAFGATVQELTDFKEKGVQMVDTTCPWVAKVWNSVDTHTRKQYTS
VIHGKYSHEETIATASFASNYIIVKDLKEAQYVCDYILQGGNREEFLQKFSKAVSAGF
DPETMLDRVGLANQTTMLKGETEQIGKMLEKTMLTKYGPAKLNDHFLLMETICDAT
QERQDALYEMVADPEIDMMIVVGGFNSSNTSHLQEIAEHKGLASFWVDSAARIDVE
KNVILHKLAHGELKETTGWLNPGKPVTIGITSGASTPDRAVEEVLHKVFKIYNPNFGG
VAPKDCGRVATPDEEH* (SEQ ID NO: 6)

Volvox carteri
>estExt_Genewise1Plus.C_50310 [Volca1:79586]
MQTTKTSRKAAFTGIKSRVHVVVLRPVQASRALVPVVQSVAAGATEAAKVDGRAL
RRSLNQTGRYVRQPTNDPVSQQLMDEHGVGYSTNGLVAQMRNDGNIWKQGTVTV
KLAKAYGYCWGVERAVRMAYEARQAHPDKKLFVTNEIIHNPEVNKRLKEMNIEIIE
DEGDGKDYSQIGNGDVVIFPAFGATVKELSDFRDKGVQMVDTTCPWVAKVWNSVD
THTRKQYTSVIHGKYSHEETIATASFASNYVIVKDLKEAQYVCDYILHGGNKEEFLA
KFSKAVSKGFDPDTMLDRVGLANQTTMLKGETEQIGKMLEATMMQKYGPAELNNH
FLLMETICDATQERQDALYDMVADPEVDFLIVVGGFNSSNTSHLQEIAEHKGLPSFW
VDSAARIDVEKNTVLHKLAHGELRETVGWLTPGKPVTIGITSGASTPDRAVEEVLAK
VFKIYDPNFTGIAPKDCGRLATPEEH* (SEQ ID NO: 7)

Chlorella vulgaris
>estExt_Genewise1.C_120060 [Chlvu1:38265]
MDDAESLALMEEHGVGYSSTGLVARMRANGNLWQEGDVKVKLAKAYGYCWGVE
RAVQMAYEARKQYPNSKLHVTNEIIHNPATVCHDQRLKEMEVNIIEDVGKGKDFSGI
KGEDVVILPAFGASWQEMKMLSDKGVQIVDTTCPWVAKVWSAVDNQARKQHTSII
HGKYSHEETIATASFATTYLIVRDIPETQYVVDYILNGGDREEFLAKFSNAMSEGFDP
DRDLLRIGLANQTTMLRDETLTIGKMLEKTMMQKYGPAELKDHYMVLDTICDATQ
AGSSPLLAERQDAVTELVQKQSDPAERVDFMLVVGGFNSSNTSHLQEIPEMAGVPSF
WVNSAACVDVEHNKITHKLAHGELVETQPWLRDGPITVGVTSGASTPDRAVEEVLD
KLFRIKDPSFSGIAQLSMEAALTPPSRPEH* (SEQ ID NO: 8)

Fig. 9B

Chlorella NC64A
>estExt_fgenesh3_kg.C_80007 [ChlNC64A_1:59658]
MQSAACATRSWLAGSPAPAPAGGSSGSGRAPRRAAAATRRLPLRVAAAAEVQQPSS
SSAKEVLERAADRTGADGAAFDPRAFRRSLNSTGRYTRKPSNDPDSLSLMEEHGVG
YSTAGLVAQMREQGYAWRQGDVNVKLAEAYGFCWGVERAVQMAYEARRAYPGQ
RLHITNEIIHNPSVNQRLKEMDVQFIDEGADGGKDFSGVKEGEVVILPAFGASVQEM
RLLNDRNVQIVDTTCPWVSKVWNAVDNQARKGHTSIIHGKWAHEETIATASFAGTY
LIVKDLKEAQYVCDYIMHGGDRAEFLAKFENAMSAGFDPEQDLQRIGMANQTTML
KGETEAIGKLLEKTQLQKYGPGELSQRFMIMDTICDATQERQDAVYKLVGQQSTPEG
IDMMLVVGGFNSSNTSHLQEIGEMKGIPSFWVDSAARIDVGANKVTHKLAHGELVE
TENWLPEGPITLGVTSGASTPDKAVEDVLDRVFRIKDPSFTGITPRKTSVQKAAHGEE
E* (SEQ ID NO: 9)

Emiliania huxleii
>e_gw1.148.2.1 [Emihu1:71395]
MIELGWTSPLATRDLGRTSIESRLHLDRTSAVPRLYLGCTAVPRLPPRLPSRLKAYPD
KRMHITNELIHNPGVNDLLKGMDIEFMEKDGRLGGGGGASGKGWLMNGHYVILPA
FGASLEEMSLLDAKGVTTVDTTCPWVSKVWTTVDKHQLSEMTSLIHGKYQHEEAIA
TASMCETYLIIKDMAQAQEVAPYILDEGLVDSYEEFMDKYRKAASPHFDPRKHLKKI
GLANQTTMYKKETQAIGKLLEKTMMVVHGPENVKHHFAAFDTICDATQVRQDAVN
EMSDEALAGDKELDFILVVGGWDSSNTAHPGLERSRLSATVPGYHVNEAPCIRPDDT
RFVDSAILVTDNFLPSGRPVRIGVTSGASTPDSVVQECIETITMLRKVQGGGARADAA
PREAESEAEAPPADTPPPADTPPPAGFEWGPAF* (SEQ ID NO: 10)

Micromonas pusilla CCMP1545
>estExt_Genewise1.C_50231 [MicpuC2:26764]
MSVMATASFAGTAMPLGRRNARATRRANAFRVRAAHDEEEPEEKADAGFKFDPSS
YGDKFDPRTFRRDLSKSDQYNRRFAKDKESAERMAREGIGYSVGASRLDRATISRSL
LSLLSLRPVPSRYRSLARAIAPPRLTTAPHRTEPNPNSTDGLVAKMRESGNSYVDAET
GVTLKLADAYGFCWGVERAVQMAYEARKQYPDAKLWITNEIIHNPTVNKRLGDMG
VNFIEETKDGKDFSGVGNGEVVILPAFGASVHEMKLLAEKGASIVDTTCPWVSKVW
NAVDAHTRKEFTSIIHGKWAHEETVATASFAGTYLVIKDMKEATYLCDYILNGGDK
EEFMAKFVNAHSEGFDPDVDLDGLGIANQTTMLKGETQAIGKLLERTMMEKHGVA
NLADHYMVMDTICDATQERQDAMYQLVEDKPDMMLVVGGYNSSNTQHLQEISED
ASVPSFWVDTPERLDEDNVIAHRLAHGELVETKDWLPEGDVVIGVTSGASTPDKVV
EDVVDMIFKTKRNMKTATPAR* (SEQ ID NO: 11)

Micromonas strain RCC299
>fgenesh2_pm.C_Chr_06000119 [MicpuN2:97588]
MEDDGIGYSKSGLVAKMRESGNVHVDGDVTFKLAEAYGFCWGVERAVQMAYEAK
KQFPDANLWITNEIIHNPTVNDRLGEMGVQFIEETAEGKDFSGCKEGEVVILPAFGAS
VHEMKLLNDKGVNIVDTTCPWVSKVWNAVDAHTRKEFTSIIHGKWAHEETIATASF
AKTYLVVKDMKEAQYVCDYVLDGGDREEFLAKFKNAYSEGFDPDTDLGALGIANQ
TTMLKGETEAIGKLLEKTMMQKHGVDKLNDHYMVMDTICDATQERQDAMYKLVD
DKPDMMLVVGGFNSSNTSHLQEISEDASIPSFWVDTHARLDADTNTITHRLAHGELV
ETKDWLPAGKVTIGVTSGASTPDKVVEDVIDVIMATKKKMSGAPAR* (SEQ ID NO:
12)

Fig. 9C

Ostreococcus strain RCC809
>fgenesh1_pm.C_scaffold_10000061 [OstRCC809_1:42594]
MANDGVSYSKTGLVATMREGGFAYAADGLTFKLADAYGFCWGVERAVQMAYEA
RKRFPEKELWITNEIIHNPTVNERLSEMGVRFIRETESDGKDFSGVREGDVVILPAFGA
SVHEMKFLADRGANIVDTTCPWVSKVWTAVDQHKRKEFTSIIHGKYSHEETVATAS
FATRYLIVKDMKEATYVREYILNGGDKAEFMQKFKNAMSLGFDPDDDLEGVGIANQ
TTMLKGETEAIGKLFEKTMMEKHGVENIADHFIVMDTICDATQERQDAMYKLVDEE
PDIMLVIGGFNSSNTSHLQEISEDKSIPSYWVDTCDRMNADTNSITHKLAHGELVQTD
DWLPRSDVVIGVTSGASTPDKVVEDVIDVVFATKRALTSEVS* (SEQ ID NO: 13)

Ostreococcus tauri
>fgenesh1_pg.C_Chr_08.0001000076 [Ostta4:11954]
MQTRVYRRELGKSDQYSRKFLNDDEAATKMANDGISYSKSGLVAKMKDEGFAYVK
DGITFKLADAYGFCWGVERAVQMAYEARKQFPESKLWITNEIIHNPTVNERLSDMG
VNFIEESENGKDFSGVQSGEVVILPAFGASVHEMKFLADRGANIVDTTCPWVSKVW
NAVDTHKRKEFTSIIHGKYSHEETVATASFATTYLIVKDMTEAEYVRDYIMNGGDKA
EFMEKFKNAMSEGFDPDEDLNGVGIANQTTMLKGETEAIGKLFQQTMMEKFGVEN
ADQHFVVMDTICDATQERQDAMYKLVDDKPDIMLVVGGFNSSNTSHLQEIAEDKSI
PSYWVDTAERLDPSKNSITHKLAHGELVTTDAWLPASDVVIGITSGASTPDKVVEDVI
DVVFATKTALKSAVSR* (SEQ ID NO: 14)

Ostreococcus lucimarinus
>eugene.0800010105 [Ost9901_3:32979]
MANDGISYSKTGLVAKMKENGLSYVEDGITFKLADAYGFCWGVERAVQMAYEAR
KQFPEAKLWITNEIIHNPTVNDRLSEMGVNFVEETSDGKDFSGVKRGEVVILPAFGAS
VHEMKFLADKGANIVDTTCPWVSKVWNAVDTHKRKDFTSIIHGKYSHEETVATASF
ATTYLIVKDMREANYVRDYILKGGDKAEFMEKFKNAMSQGFDPDEDLDGVGIANQ
TTMLKGETEAIGKLFQSTMMEKFGVENVDQHFVVMDTICDATQERQDAMYKLVDA
KPDIMLVVGGLNSSNTQHLQEISEDKAIPSYWVDTADRLNADTNSISHKLAHGELVT
TDGWLPAGDVVIGITSGASTPDKVVEDVMDVVFATKRALESAVSR* (SEQ ID NO:
15)

Phaeodactylum tricornutum
>fgenesh1_pm.C_chr_4000025 [Phatr2:41845]
MKSDRFHRRGFKEVREGVESNMEDQFQSPIVNSLRTSNFVMDRDGVKVYLAKDFGF
CWGVERSIALAYEAAEHFPDRKLHITNELIHNPEVNENLKAKNVQFIEKLGDGTKNF
ASVQDGDVVILPAFGASFEEMDYFDKKNVEIVDTTCPWVSKVWNTVDKHQKQGLT
SVIHGKYAHEETVATTSFCEDFICVKNFKEAEMVANYILNGGDKDAFMKHFENAVS
EGFDPDKHLEKVGLANQTTMYKKETRAIGQLFQKTMMKKFGPVKSKEHYMEFDTIC
DATQERQDAIHDMVESAQKDGLDFILVIGGWDSSNTAHLLEIPVHAGIRAFHINRAEC
IGADNTITHRTVDGEIVTTQLLEDMDKEVVMGVTSGASTPDAAVQDSLSQIFLLKKM
YDESKK* (SEQ ID NO: 16)

Fig. 9D

Thalassiosira pseudonana
>estExt_Genewise1.C_chr_50354 [Thaps3:28326]
MEDQFKSSLVDELKTNDFVIEKDGVKVYLAKDFGFCWGVERSIALAYEAVEHFPGK
TVHITNELIHNPEVNDKLHDMNVQFIEKLGEGKKDFSKIGEGDVVILPAFGASFEEMT
LMNNKNVEVVDTTCPWVSKVWNTVDQHQRKGLTSVIHGKYGHEETVATVSFCEDY
ICVKDIKEAEMVADYIINGGDKEKFLKYFEKAVSKGFDPDTMLDKVGLANQTTMYK
KETRAIGQLMQKAMMKKFGPVNAKDHYLEFDTICDATQERQDAISDLVENSDELGL
DFILVVGGWDSSNTAHLLEIPEKAGVRSFHINKSECIGADNTITHRTVDGEIVTEKFIE
DIENKDKKLVMGVTSGASTPDKAVQDSLDQIFMLKKVYSKEE* (SEQ ID NO: 17)

Fig. 10A

ESTs of Phytoene desaturase (PDS) from differrent algal genomes, JGI

| Algae | PDS1 | EST | PDS2 | EST |
|---|---|---|---|---|
| Micromonas sp.RCC299 | MicpuN3/Chr_07:126545-128430 | 6 | MicpuN3/Chr_10:1133416-1135162 | 2 |
| Micromonas pusilla CCMP1545 | MicpuC2/scaffold_1:1585868-1587673 | 12 | MicpuC2/scaffold_16:22128-24332 | 2 |
| Ostreococcus tauri | Ostta4/Chr_10.0001:464856-466664 | 2 | Ostta4/Chr_16.0001:77361-78983 | 0 |
| Ostreococcus lucimarinus | Ost9901_3/Chr_10:488156-489955 | 0 | Ost9901_3/Chr_15:64879-66564 | 2 |
| Ostreococus RCC809 | OstRCC809_1/scaffold_3:868854-870784 | 2 | OstRCC809_1/scaffold_8:754092-755669 | 0 |
| Thalassiosira pseudonana | Thaps3/chr_6:1793806-1795708 | 3 | Thaps3/chr_1:1371106-1373101 | 2 |
| Phaeodactylum tricornutum | Phatr2/chr_8:74943-76736 | 5 | Phatr2/chr_24:265288-267343 | 1 |
| Aureococcus anophagefferences | Auran1/scaffold_1:1218979-1220427 | 5 | Auran1/scaffold_3:75201-77110 | 4 |
| Emiliania huxleyi CCMP1516 | Emihu1/scaffold_328:65825-68598 | 2 | Emihu1/scaffold_322:6682-11348 | 6 |
| Dunaliella salina CCAP1918 | | 1 | | 10 |

Micromonas sp.RCC299

PDS1

>estExt_fgenesh2_kg.C_Chr_070003 [MicpuN3:104873]

MSALSSRAAVGQRVRARVAVPSATSPSSRRPLRVVAEDFPQPAQIKNTDNYRDGEAL
SKKFKELKGMGEKKKVVIVGGGLSGLACAKYLVDAGHEPIVLEGRDVLGGKVSAW
KDKDGDWIETGLHIFFGAYPNMMNLFAELDIEDRLQWKVHKMIFAMQELPGEFTTF
DFVKGIPAPLNFGLAILLNQKMLTLGEKLQTAPPLIPMLIEGQDFIDEQDELSVLDFMR
KYGMPDRINEEVFISMAKALDFIDPDKLSMTVVLTAMNRFLNETDGLQMAFLDGNQ
PDRLCAPMVDHIKAGGGDVKLKQRVKEFVLNDDGSVKCLKMVSGEEIVADEYVSA
VPVDIMKRMMPKQWGTMPFFHQIQELEGIPVINIHLWFDRKLKNVDHLCFSRSPLLS
VYADMSTTCKEYYDEEKSMLELVFAPCSPLAGGKTNWIAKSNEEIVEATMKELERLF
PLEIGPKSPDGVGAKLLKHAVVKTPRSVYAAIPGRNKYRPSQATPISNFTLAGDWTSQ
KFLGSMEGAVLAGKLAAEVVTDKAVYGAPTKGLKKIVPDVIAEARKLQEKEPVGVT
GESEVSFGGGCVMEDADEKELAVLDPEQMVKLEGAPAR* (SEQ ID NO: 18)

Fig. 10B

PDS2
>fgenesh2_kg.C_Chr_10000024 [MicpuN3:96647]
MSAAIRAVSTLPSSTTRTLSGQKRHRHRRRFARSSSLRAVAGDFPTPDLDKPGNANY
QEAKALSAKLAGNAASVGASHEPKRVVVVGGGLAGLSCAKYLADAGHVPVVLERG
DVLGGKVSAWQDEDGDWIETGLHIFFGAYPNMMNLFKELGIEDRLQWKEHAMTFA
MQDYPGEFTKFYFPPNLPAPFNMAYAILTNDKMLTWTEKLRTGIPLVPMLLGGQEYI
NAQDELSVQQWMRKNFMPERVREELFIAMGKALDFIDSDKLSMTVILTAMNRFINE
THGSKTAFLDGNQPDRLCAPMAKHVETVAGGEVRTKAGLKRILVDETTGDVTGME
LIGGEVVTGDHYVSAMPVDALKLLLPDVWKPDPFFKQLEELEGIPVINVHIWFDRKL
RPYDGLVFSRSPLLSVYADMSECCKEYASDDTSMLELVFAPCSKEAGSDVNWIGKSD
EEIVQATLGELERLFPDEIAADGSKAKVVKHAVVKTPRSVYAAVPGRNKFRPSQNTP
VKNFTLAGDFTYQKFLGSMEGAVLSGKLAAEVVADKMAGREAKPVKEVVARYR*
(SEQ ID NO: 19)

Micromonas pusilla CCMP1545
PDS1
>e_gw1.1.1174.1 [MicpuC2:12341]
MTARRVAQSRVAPAAASRARALRVVAKDYPKPDKISDTDNYREGAALSQKFKELK
GMGKKKKVAIVGGGLSGLACAKYLVDAGHEPIVLEGRDVLGGKVSAWQDKDGDW
IETGLHIFFGAYPNMMNLFAELDIEDRLQWKVHKMIFAMQELPGEFTTFDFMKGIPA
PLNFGLAILLNQKMLSLPEKLQTAPPLIPMLIEGQDFIDAQDELSVLDFMRKYGMPERI
NEEVFISMAKALDFIDPDKLSMTVVLTAMNRFLNETDGLQMAFLDGNQPDRLCAPM
ADHVKAGGGEVRMKARLKEFVLNDDGSVKCLKMTNGEEIVADEYVSAVPVDVMK
RLLPKKWSNMPFFHQIQNLEGIPVINIHLWFDRKLQNVDHLCFSRSPLLSVYADMSTT
CKEYYDEEKSMLELVFAPCSPLAGGNTNWIAKSNQEIVDATMKELERLFPLEIGPGSP
DGVGAKLLKHAVVKTPRSVYAAIPGRNKYRPSQATPISNFTLAGDWTSQKFLGSME
GAVLGGKLAAEVVTDKAIYGGPTKGIKKIVPDVVKEANAMEAREPEGSKGESELSY
GAGCVMGEEQEKELAVFDPEQMVTMDNYVARESIPVSR* (SEQ ID NO: 20)

PDS2
>estExt_fgenesh1_pg.C_160006 [MicpuC2:49039]
MAPHALSSASWTTPTRLPSRRCRRASAARGRFAASPSPLVVAPRAGDYPAPDLDVPS
NRNYQDAKALSAKLTRNVADVGASHAPKRVVVVGGGLAGLSCAKYLADAGHVPIV
IERGDVLGGKVSAWRDDDGDWIETGLHIFFGAYPNMMNLFDELGIGDRLQWKEHA
MTFAMRDFPGEFTKFNFPKGVPAPFNMAYAILSNDRMLSPAEKLRTGAPLVPMLLG
GQDYIDAQDELSVQEWMRRNFMPERVREELFIAMGKALDFIDSDKLSMTVILTAMN
RFINETHGSKTAFLDGNQPDRLCAPMAEHFVSRGGSVRLGAGMKKFLTTDDSVSVT
GIELVSGEVVTGDHYVSAMPVDALKLLLPEPWKRAPFFAQLKELEGIPVINVHLWFD
RKLRPYDGLVFSRSKLLSVYADMSECCAEYADAERSMLELVFAPCDERAGSDVNWI
AKSDQDIVDATVAELRRLFPNEIKADGTGAKVVKHAVVKTPRSVYAAIPGRNKFRPS
QRTPIENFTLAGDFTSQKFLGSMEGAVLSGKLAAEVIADQYAGRVGKPIKEVDARYR
* (SEQ ID NO: 21)

Fig. 10C

*Ostreococcus tauri*
PDS1
>e_gw1.10.00.97.1 [Ostta4:19516]
MDARALRAQKTQRGSTSSSRRAVRVVAKDYPKPDNIDKTENYRIAGDLSKRFASDL
RVRDGEKKKVAIVGGGLSGLACAKYLAEAGHEPIVLEARDVLGGKVSAWKDKDGD
WIETGLHIFFGAYPNMMNLFAELDIEDRLQWKVHKMIFAMQELPGEFTSFDFIKGIPA
PLNFGLAILLNQKMLTLPEKLQTAPPLLPMLIEGQDFIDKQDELSVQQFMRKYGMPE
RINEEVFISMAKALDFIDPDKLSMTVVLTAMNRFLNETDGLQMAFLDGNQPDRLCAP
MVESITKNGGSVMTKQRLKEFVLNEDGSVKHLAMANGDIVEADEYISAMPVDVMK
RMMPKKWGEIPHFAQLKELEGIPVINIHLWFDRKLKNVDHLCFSRSPLLSVYADMST
TCKEYYDEEKSMLELVFAPCSPIAGGKTNWIAKSNQEIVDATMLELERLFPLEIGPKS
PDGVGARLLKHAVVKTPRSVYAAIPGRNKFRPSQETPIKNFTLAGDYTSQKFLGSME
GAVLAGKLAAEVVASRAKGKATQGLKPVQQSIINAIGPVSEPVGVIGDTEFAFGGGK
VMEVADEAELEKFDAEQLVKLDGWTGSKEKAARAR* (SEQ ID NO: 22)

PDS2
>e_gw1.16.00.59.1 [Ostta4:21852]
MRSALITAPIVDARRARVHRHASITRARDYPKPDLDVPSNGNYQESKALSQKLKSIAL
AERKSVLIIGGGLAGLSCGKYLSDAGARPIVVERNKMLGGKVSAWRDAEGDWIETG
LHIFFGAYPNMMNLFAELGIEDRLQWKEHSMTFAMKDYPGEFTKFKFPENVPAPFN
MAYAILSNDKMLTWTEKLRTGAPLVPMLAGGQGYIDAQDELSVEEWMKKNFMPK
RVSDELFIAMGKALDFIDVDKLSMTVILTAMNRFINETHGSKTAFLDGNQPDRLCAP
MKEHIERVGGGEVMVDTPMQEILTDVEGNVEGVKLRNGEILTADHYVSAMPVDAL
KLKLPDAWKPMPFFKQLDELEGIPVINVHLWFDRKLRPYDGLVFSRSPLLSVYADMS
ECCKEYTDSERSMLELVFAPCDKRAGSDINWIGASDEEIVAATLKELEKLFPDELGSN
GGAKLRKSAVVKTPRSVYAAIPGRNKFRPSQQTPIKNFTLAGDFTSQKFLGSMEGAV
LSGKLAAEVVAETLAGCEPTRGIKPVHESVRV* (SEQ ID NO: 23)

*Ostreococcus lucimarinus*
PDS1
>e_gwEuk.10.107.1 [Ost9901_3:38345]
MTSRAGTKAKTRATRRSGMRVEAKDYPKPDNIDKTDNYRIASELSKRFATDLKANG
TEKKRVAIVGGGLSGLACAKYLAEAGHEPIVLEARDVLGGKVSAWQDKDGDWIET
GLHIFFGAYPNMMNLFNELKIEDRLQWKVHKMIFAMQELPGEFTSFDFIKGIPAPFNF
GLAILMNQKMLSLPEKLQTAPPLLPMLIEGQDFIDKQDELSVQDFMRKYGMPERINE
EVFISMAKALDFIDPDKLSMTVVLTAMNRFLNETDGLQMAFLDGNQPDRLCAPMVD
SIEKNGGSVKTKQRLKEFVLNEDGSVKHLAMANGDIIEADEYISAMPVDVIKRMMPK
PWAEMPHFAQLKELEGIPVINIHLWFDRKLKNVDHLCFSRSPLLSVYADMSTTCKEY
YDEEKSMLELVFAPCSPIAGGKTNWIAKSNQEIVDATMLELERLFPLEIGPKSPDGVG
AKLLKHAVVKTPRSVYAAIPGRNKFRPSQETPIKNFTLAGDYTSQKFLGSMEGAVLG
GKLAAEVVASRAKGMKTQGLKAVQKSIIDSIGPAKEPLGVVGESEFAFGGGKVMED
ADEAELANFDAEQLTKLDGWTGSKEAASVRAR* (SEQ ID NO: 24)

Fig. 10D

PDS2
>estExt_GenewiseEukaryote.C_Chr_150066 [Ost9901_3:47627]
MRAALAPRPIPLSRASGARARTATPRTRCADYPKPDLDVKSNANFQEAKAKSARLAT
FRARVRRDDAPEKPTVLVIGGGLAGLSCGKYLADAGCAPTVIERGKALGGKVSAWR
DDDGDWIETGLHIFFGAYPNVMNLFRELDIEDRLQWKEHAMTFAMKDYPGEFTKFY
FPPALPAPLNMGYAILSNDKMLTWSEKLRTGAPLVPMLVGGQDYIDAQDELSCEEW
MKKNFMPKRVRDELFIAMGKALDFIDADKLSMTVILTAMNRFINETHGSKTAFLDG
NQPDRLCAPMAEHIERVGGGKVITDAPMQEILVDADGNVEGVKMRDGQIMTADHY
VSAMPVDALKLKLPDVWKAMPFFRQLNELEGIPVINVHLWFDRKLRPYDGLVFSRS
PLLSVYADMSECCAEYKDDDRSMLELVFAPCDKRAGSDVNWIGASDEDIVAATMK
ELETLFPDELGAGKDGASGAKLRKFAVVKTPRSVYAAIPGRNKFRPSQHTPIKNFTLA
GDYTSQKFLGSMEGAVLSGKLAAEVVAETFAGVEPTTRVKPVHESVA* (SEQ ID
NO: 25)

Ostreococus RCC809
PDS1
>estExt_Genewise1Plus.C_31180 [OstRCC809_1:45356]
MSSSALSARRGALSQGSPTTRGARNQRRQHRAGGRARVVRVEAKDYPKPDAISQTE
NYRVAGALSSRFTSDLKVSGEGQKKKVAIVGGGLSGLACAKYLAEAGHEPIVLEAR
DVLGGKVSAWQDKDGDWIETGLHIFFGAYPNMMNLFSELDIEDRLQWKVHKMIFA
MQELPGEFTTFDFIKGIPAPFNFGLAILLNQKMLTLPEKLQTAPALLPMLIKGQEFIDE
QDELSVLDFMRKYGMPERINKEVFISMAKALDFIDPDKLSMTVVLTAMNRFLNETD
GLQMAFLDGNQPDRLCAPMVDSITKNGGSVHMKQRLKEFVLNEDGSVKHLAMAN
GDIIEADEYISAMPVDVMKRMMPKQWGEMPHFAQLKELEGIPVINIHLWFDRKLTN
VDHLCFSRSPLLSVYADMSTTCKEYYDEEKSMLELVFAPCSPIAGGKTNWIAKSNQEI
VDATMKELERLFPLDIGPNSPDGVGAKLLKHAVVKTPRSVYAAIPGRNKFRPSQETPI
SNFTLAGDYTSQKFLGSMEGAVLGGKLAAEVVASRAKGMATQGLKPVQQSIINGLS
AGADEAMGPVGETELAFGGGKVMDESDEADLARFDAEQLVKLDGWTGSKEAARA
R* (SEQ ID NO: 26)

PDS2
>e_gw1.8.589.1 [OstRCC809_1:26801]
MTSSALRLGDFPKPALDVPTNENYAEAKALSQKLRNFQIDRSSTEKPTVLVIGGGLA
GLSCGKYCSDAGAEVTLIERAKMLGGKTSAWQDKDGDWIETGLHIFFGAYPNMMN
LFAELEIEDRLQWKEHSMTFAMRDFPGEFTKFFFPPALPAPFNMGWAILSNDKMLSW
TEKIRTGIPLLPMLLGGQEYIDAQDELSVEEWMKKNFMPKRVRDELFIAMGKALDFI
DADKLSMTVILTAMNRFINETHGSKTAFLDGNQPDRLCAPMAEHIERVGGGKVLVD
TPMQEILVDENGRVEGVKLRNGEIVTADHYVSAMPVDALKLKLPEKWRAMPFFKQL
DELEGIPVINVHLWFDRKLRPYNGLVFSRSPLLSVYADMSECCAEYADENRSMLELV
FAPCDMTAGSDVNWIAASDDEIVSATLKELENLFPDEIGGEEGAKLRKAAVVKTPRS
VYAATPGRNKFRPSQNTPIENFTLAGDFTSQKFLGSMEGAILSGKLAAEVTAEKLSGR
QPSRGVKPVHHSMKM* (SEQ ID NO: 27)

Fig. 10E

Thalassiosira pseudonana
PDS1
>estExt_fgenesh1_pg.C_chr_60677 [Thaps3:23291]
MIITNFILSTVLATSMAFQPHTPILSKPSFSNRVHRSPKIGSSNLVMKDFPKPNVEDTD
NYRYAEAMSTSFKTSLRVTNDSQKKKVAIIGGGLSGLSCAKYLSDAGHEPTVYEARD
VLGGKVSAWQDEDGDWIETGLHIFFGAYPNVMNMFAELGIHDRLQWKIHQMIFAM
QELPGEFTTFDFIPGIPAPFNFGLAILMNQKMLTLGEKIQTAPPLLPMLIEGQSFIDAQD
ELSVTQFMRKYGMPERINEEVFIAMAKALDFIDPDKLSMTVVLTAMNRFLNESNGLQ
MAFLDGNQPDRWCTPTKEYVEARGGKVKLNSPIKEIVTNDDGTINHLLLRSGEKIVA
DEYVSAMPVDIVKRMLPTTWQTMPYFRQLDELEGIPVINLHMWFDRKLKAVDHLCF
SRSPLLSVYADMSVTCKEYEDPNKSMLELVFAPCSPIAGGNVNWIGKSDEEIIDATM
GELARLFPTEIANDDKWPATKMQGPNGQAKLEKYAVVKVPRSVYAAIPGRNKYRPS
QTSPIPHFTMAGCYTSQKFLGSMEGATLAGKLAAEVIANRALGNADKPVKEIQQHIID
SASKHVVKEPVGVKGEGAIAFGGGYTVGKKEEDLLRESDPAQYELAVAK* (SEQ ID
NO: 28)

PDS2
>fgenesh1_pg.C_chr_1000517 [Thaps3:1383]
MKFLLPLLPAVAGAFSITHLSQHPSLRMHQSLSTSLYSSSSSTSQRPRRPTPDRIRNTQ
NFKEAKELSQKFITDFQQLQKVGSGEPKRVAIFGGGLSGLSCAKYLSDAGHIPTLYEA
RGVLGGKVSAWQDEDGDTVETGLHIFFGAYPNIHNLFDGLKIQDRLQWAPHRMTFA
MQELPGQFTTFEFPAGVPAPLNMAAAILGNTEMLTLEEKIKMVPGLLPMLLEGQSFID
EQDELSVLQFMRKYGMPERINEEIFIAMGKALDFIDPDLLSMTVVLTAMNRFINEAD
GSQTAFLDGNPPERLCQPMKESIEKKGGEVVCNSPVVEIQLNEESNVKSLKLANGTEI
TADYYVSAVPVDVFKRLVPTQWSTMPYFRQLDELEGIPVINIQIWFDRKLNSVDGLC
FSRSPLLSVYADMSTCCEEYASNDKSMLELVFAPCSPEAGSPLNWIAKPDSDIIDATM
KELERLFPLEIGPDAPEEKRANVVKSTVVRVPRSVYAAVPGRNKYRPSQESPIENFIM
AGDYATQKYLGSMEGAVLSGKLAAEVICDKFMGRAERKGVKEVHSSVLTKQIEERT
PAGIAMEKGRVSPTSYGGGQQGGFENP* (SEQ ID NO: 29)

Phaeodactylum tricornutum
PDS1
>estExt_fgenesh1_pg.C_chr_80031 [Phatr2:45735]
MMFHYKTGSSWFLLLSASITTTLTTTTMTTTHAFAPHTRLSVPHGASRLVMKDFPKP
NLEDTDNYRFYRDLSHSFSTTLKAPSPESRKKVAIIGGGLSGLACAKYLADAGHQPV
VYEARDVLGGKVSAWQDADGDWIETGLHIFFGAYPNMMNLFAELDIHDRLQWKVH
KMIFAMQELPGEFTTFDFIPGIPAPFNFGLAILMNQKMLTLPEKIQTAPPLLPMLVRGQ
DFIDEQDELSVLDFMRKYGMPERINEEVFISMAKALDFIDPDKLSMTVVLTAMNRFL
NEDNGLQMAFLDGNQPDRLCAPMVEHIQARGGQVNLNSPVQEIVTREDGSVDYLL
MRSGEKVVADEYVSAMPVDIVKRMLPEKWQTMPYFRQFDELEGIPVINLHMWFDR
KLKAVDHLCFSRSPLLSVYADMSVTCKEYYDESASMLELVFAPCSPLAGGNVNWIA
KTDEEIIDATMGELARLFPTEIAADPTWPATKNQGPNGEAKLRKYAVVKVPRSVYAA
IPGRNKYRPSQTTPIDNFTLAGDWTSQKFLGSMEGAVLGGKLAAEVLARKAANLPAP
ELANKPVRDEIVQKAQTHVARPPAGVKGQGAIAFGGGAVLGTENKALLRDVDPSQF
VEA* (SEQ ID NO: 30)

Fig. 10F

PDS2
>estExt_Phatr1_ua_kg.C_chr_240013 [Phatr2:55102]
MKLVFSVAVLSCWNAWAEAFAPNTNVPFHRIAKAQSSLSIVQAPDFSSVGSHLEAQA
NVEYLKKLARPDKPLQVIVVGGGLAGLSTAKHLVDAGHRPIVLEARSLLGGKVAAW
RDTDGDVTETGLHVFFGAYPNALTLFDELKIADRLQWKPHQMLFAKPGRPTREFSVF
DFPPLPAPLNAAVAILSCTDMLTWPEKIRLGIGLIPAYLQGQTYVESQEHVTVQQWM
EQRGIPQSVTDEVFLAMSKALGFIGPEQLSMQCVLIALNRFLQETNGSRIAFLDGSPTE
RLCEPLKEYIEARGGLVRTNVPVKRILTNLDENDSVAGLLLKGGEVVSGDAYVNAM
PVDALKKLTPEPWRKMEYFQRMQKLRGVPVMNLHLWFDRKLSTVDNLIFSRSPLLS
VYADMSEACEGYASKIIVSMLELVLAPAAKYMTKSDDEILQATMLELERLFPQEIKA
DGSLAAVTKFTLVRTPTSVYETLPGMEAARPTQKSPISNFFCAGDFSSQKYLASMEG
AILSGQLAAKAVADSYVNAASNDQSAVVAPPRQLTPRPADPSAADAHDVVPDRTM
YVAKVASHIPASVQEELEGAVVV* (SEQ ID NO: 31)

Aureococcus anophagefferences
PDS1
>ADA_fgenesh2_pg.C_scaffold_1000203 [Auran1:77905]
MSRLLCIAAFAAALQPQPRAPEPPRIEKTANYKAAAEASARLAGELKAPPASRTPEPP
RIEKTANYKAAAEASARLAGELKAPPASRKTVAVVGGGLSGLACGKYLSDAGHEAT
VYEARDVLGGKVSAWQDDDGDWIETGLHVFFGAYPNVLNLFKELDIRDRLQWKAH
RMSFAMRERPGEFTSFEFPEGVPAPLNMAAAILTNTEMLSLVDKIRMVPGLLPMLLE
GQSFIDEQDELSVLQFMKKYGMPDTINEEIFIAMGKALDFIDPDKLSMTVVLTAMNR
FINEADGSQTAFLDGNQPERVCAPMADRIRDAGGDVETDAPLAEIRVNDDGGVAAL
VLKDGREVVADEYVLAMPVDVTKRLIPEAWSTMPFFRQLNELEGIPVINVQLWFDA
KFDSLDGLAFSRSPLLSVYADMSRSCAEYADDDRSMLELVFAPCAPEAGSPVNWLA
KPDDDVVAATLDELKQLFPADMADAKLLKSAVVRTPRSVYAAIPGRNKYRPSQRTPI
PNLTLAGCYTSQKFLGSMEGAVLAGKLAAEVVAARAVGAAAPGLKDVQRTVVAA
AADAAPRRPTGCGKGDSAIAYGGGAVLAARGS* (SEQ ID NO: 32)

PDS2
>estExt_fgenesh2_pg.C_30012 [Auran1:70771]
MARLVCLSLAAVAGALVGSRSRLPAPAARSSRATTVMKDFAKPNVEDTIPYREASTL
SDRFPNELYAPAPQKKKVAIIGGGLSGLSCAKYLSDAGHEPTVYEARDVLGGKVHK
MVFAMQELPGEFTTFDFIPGIPAPFNFGLAILLNQKMLTLGEKLQTAPPLLPMLIEGQD
FINAQDELSVLDFMRKYGMPDRINDEVFISMAKALDFIDPDKLSMTVVLTAMNRFLN
EDNGLQMAFLDGNQPDRLCAPMVESVEKKGGRVVTGAPLDRIEVDAAGNVDKLVL
RSGEEVVADEYVSAMPVDVLKRMVPEAWSTMPYFKQLDELEGIPVINLHLWFDEKL
TTIDHLCFSRSPLLSVYADMSTTCKEYYDEDKSMLELVFAPCSPLAGGDTNWIGKTD
EDIIQATMGELARLFPTEIAADPAYPGTMTERTFLGEKQAQLTGGAKLRKSTVVKVP
RSVYAAIPGRNKYRPSQKTPIPNFSLCGCFTSQKFLGSMEGAILAGKLAAEVVSARAV
GADAPGLKEVQQHVIDAAADAAPKKPVGCRGDTAIAFGGGYTFDQLVTRELKEQD
AVQFN* (SEQ ID NO: 33)

Fig. 10G

Emiliania huxleyii
PDS1
>e_gw1.328.3.1 [Emihu1:74977]
MLRTATISLLAALSSLLSVAAAAHAPRPPTPSRIKLTQNFREAAALSAKLADPATPQQ
RKKVAVIGGGLSGLACAKYLSDAGHTPLVLEARDVLGGKVSAWQDADGDMIETGL
HIFFGAYPNMMNLFQELGIEDRLQWKAHRMTFAMPQLPGEFTSFDFPDGVPAPLNM
AAAILGNTEMLSLLDKVRMVPGLLPMLLEGQPFIDAQDELSVKEFMDKYGMPETVN
EEIFIAMAKALYHTAHSPEPTLDSAALDFMDPDRMSMAVVLTAMNRFINEADGSQT
AFLDGGQPERLCAPVVDHVLSRGGEVRLGAPLAAIEVGDDGQVACLRLADGSSVEA
DVYVSAVPVDVFKKLLPASWSTMPFFRQTEELIGIPVINVQLWFDKKLRSVDGLCFS
RSPLLSVYADMSTCVEEYADADRSMLELVFAPATREVGADRNWIGASDAEVVAACL
GELSRLFPGEIGGEGGAELLKHAVVRTPRSVYAATPGRNRYRPSQATQATPVPNFVL
AGDWTSQKFLGSMEGAVLAGKLAAEVIADRAAGRAAATSQTLKPVHEEVVAAAEG
AAPREPVGVRGRHPIAFGGGQQGLGETKFEHA* (SEQ ID NO: 34)

PDS2
>estExtDG_Genewise1Plus.C_3220001 [Emihu1:430592]
MLRAATISLLAALSSLLSVAAAAHAPRPPTPSRIKLTQNFREAAALSAKLADPATPQQ
RKKVAVIGGGLSGLACAKYLSDAGHTPLVLEARDVLGGKVSAWQDADGDMIETGL
HIFFGAYPNMMNLFQELGIEDRLQWKAHRMTFAMPQLPGEFTSFDFPDGVPAPLNM
AAAILGNTEMLSLLDKVRMVPGLLPMLLEGQPFIDAQDELSVKEFMDKYGMPETVN
EEIFIAMAKALYHTAHSPEPTLDSAALDFMDPDRMSMAVVLTAMNRFINEADGSQA
RACTAFLDGGQPERLCAPVVDHVLSRGGEVRLGAPLAAIEVGDDGQVACLRLADGS
SVEADVYVSAVPVDVFKKLLPASWSTMPFFRQTEELVGIPVINVQLWFDKKLRSVDG
LCFSRSPLLSVYADMSTCVEEYADADRSMLELVFAPATREVGADRNWIGASDAEVV
AACLGELSRLFPGAPCTPPRPAATATGRARRRPSPTLCSRATGQAKSSSARWRGRCW
RASSRPRSSPTAPPAAPPRRRRRSSPCTRRWSPRPRAPPRASQWACAGGTQLPLAAGS
RAWERRSLSTRDRARGRGGGSRHTPAGPGPGRQGPGRILIRVQQAWLSSTHTNTHTS
VRCVRGYTSYN* (SEQ ID NO: 35)

REGULATING THE PRODUCTION OF ISOPRENOIDS IN ALGAL CELLS

CROSS REFERENCE TO RELATED APPLICATIONS

This application is a U.S. National Phase Application of International Application No. PCT/US2009/041687 filed on Mar. 24, 2009 and asserts priority to U.S. Application Ser. No. 61/125,434 filed on Mar. 24, 2008, all of which are hereby incorporated by reference in their entirety.

BACKGROUND OF THE INVENTION

Isoprenoids isolated from plants and other natural sources are useful as biofuels, nutraceuticals, commercial flavor and fragrance compounds as well as anti-malarial and anti-cancer drugs. A majority of isoprenoids in use today are natural products from source organisms, such as trees and marine invertebrates, which are not amenable to large-scale cultivation to produce commercially viable quantities.

Carotenoids are pigments that are useful for pharmaceuticals, food supplements, electro-optic applications, animal feed additives, colorants, etc. Carotenoids are synthesized from isoprenoid precursors only in photosynthetic organisms and some microorganisms Extraction of a natural product, such as isoprenoids and carotenoids, from a natural source, such as photosynthetic organisms, is typically limited by the availability of the natural source, and synthetic production of the natural products. Accordingly, there is a need in the art for improved host cells that provide for increased production of isoprenoids or carotenoids.

SUMMARY OF THE INVENTION

In one aspect, the invention relates to a method for increasing the production level of isoprenoids in an algal cell. The method includes increasing expression of a polynucleotide sequence that encodes 4-hydroxy-3-methylbut-2-enyl diphosphate reductase (IDS) in the cell.

In another aspect, the invention relates to a method for increasing the production level of carotenoids in an algal cell. The method includes increasing expression of a polynucleotide sequence that encodes phytoene desaturases (PDS) in the cell.

In a further aspect, the invention relates to an algal cell that includes a polynucleotide sequence. The polynucleotide sequence is genetically engineered to express a higher level of 4-hydroxy-3-methylbut-2-enyl diphosphate reductase (IDS) than a corresponding wild type algal cell, wherein the cell produces an increased level of isoprenoids than a corresponding wild type algal cell.

In yet a further aspect, the invention relates to an algal cell that includes a polynucleotide sequence. The polynucleotide sequence is genetically engineered to express a higher level of phytoene desaturases (PDS) than a corresponding wild type algal cell, wherein the cell produces an increased level of carotenoids than a corresponding wild type algal cell.

BRIEF DESCRIPTION OF THE DRAWINGS

FIG. 5: The cDNA sequence of the LytB gene of *Dunaliella salina* CCAP 19/18, which was assembled from EST sequences obtained from the Joint Genome Institute in Walnut Creek, Calif. Shown is the LytB cDNA sequence deduced from EST data with the predicted translation start site and stop codon highlighted in bold letters.

FIG. 6: Shown is the predicted chloroplast precursor protein of IDS with a length of 474 amino acids, including the ChloroP predicted transit peptide highlighted in bold letters.

FIG. 7: Phytoene Desaturase from *Dunaliella salina* strain CCAP19/18. cDNA sequence from start codon to stop codon.

FIG. 8: Protein Sequence of phytoene Desaturase from *Dunaliella salina* strain CCAP19/18 with the predicted 19 amino acids of the transit peptide (ChloroP Program) in bold letters FIGS. 9A-9D: IDS/HDR protein sequences from the Joint Genome Institute.

FIGS. 10A-10G: ESTs of Phytoene desaturase (PDS) from various algal genomes.

DETAILED DESCRIPTION OF THE INVENTION

Figure 1:
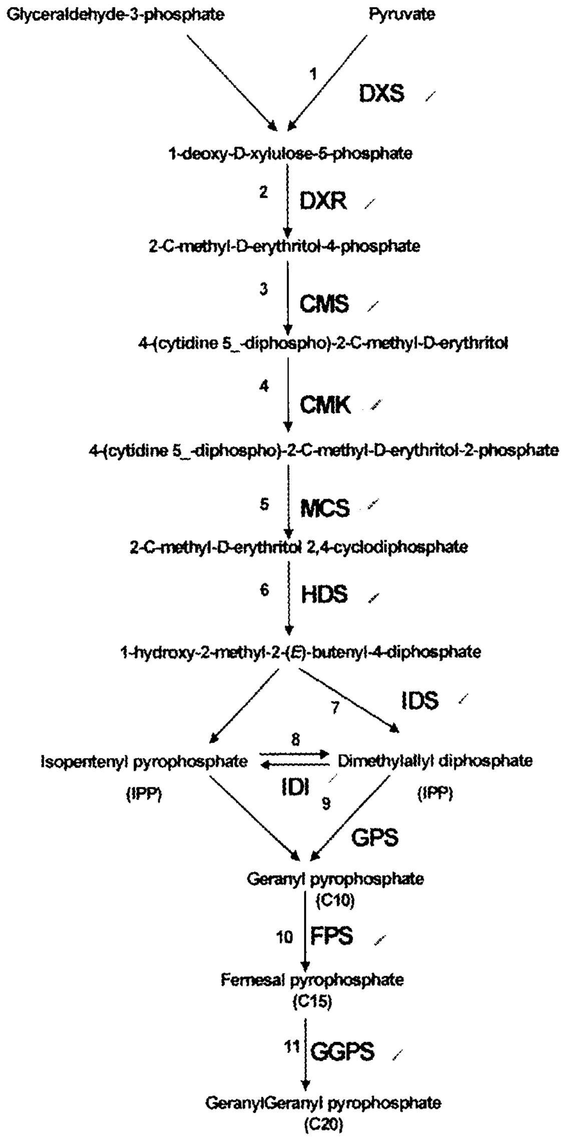
FIG. 1: A schematic diagram for the biosynthesis pathway of isoprenoid precursors or the MEP (methylerythritol) pathway from higher plants. 1) DXS: 1-deoxy-D-xylulose5phosphate synthase, 2) DXR: 2-C-methyl-D-erythritol 4-phosphate synthase, 3) CMS: 4-(cytidine 5_-diphospho)-2-C-methyl-D-erythritol synthase, 4) CMK: 4-(cytidine 5_-diphospho)-2-C-methyl-D-erythritol kinase, 5) MCS: 2-C-methyl-D-erythritol 2,4-cyclodiphosphate synthase, 6) HDS: 1-hydroxy-2-methyl-2-(E)-butenyl-4-diphosphate synthase, 7) IDS, isopentenyl diphosphate:dimethylallyl diphosphate synthase, 8) IDI: isopentenyl diphosphate: dimethylallyl diphosphate isomerase, 9) GPS: Geranyl pyrophosphate synthase, 10) FPS: Fernesyl Pyrophosphate synthase, 11) GGPS, geranylgeranyl pyrophosphate synthase.

Applicants have discovered that the expression of polynucleotide sequences that encode 4-hydroxy-3-methylbut-2-enyl diphosphate reductase (IDS) and phytoene desaturases (PDS) is the rate-limiting step in the pathway for production of isoprenoids and carotenoids, respectively. Accordingly, enhancing expression of genes encoding IDS and PDS in an algal cell increases the production of isoprenoids and carotenoids, respectively.

Method for Increasing Production of Isoprenoids

In one aspect, the invention relates to a method for increasing the production level of isoprenoids in an algal cell. The method includes increasing expression of a polynucleotide sequence that encodes 4-hydroxy-3-methylbut-2-enyl diphosphate reductase (IDS) in the algal cell.

The term “isoprenoid” refers to compounds that have a common biosynthetic origin, i.e., a single metabolic precursor, isopentenyl disphosphate (IPP) and its isomer dimethylallyl diphosphate (DMAPP). Isoprenoids are made up of isoprene (C5) units. The number of carbon atoms present in isoprenoids are typically divisible by five (C5, C10, C15, C20, C25, C30 and C40). Irregular isoprenoids and polyterpenes have been reported, and are also included in the definition of “isoprenoid.” Isoprenoid compounds include, for example, monoterpenes, diterpenes, sesquiterpenes, triterpenes, and polyterpenes.

Production of an isoprenoid is considered increased according to the invention if the production is increased at least about 10%, preferably, at least about 20%, more preferably at least about 30%, even more preferably at least about 40%, and most preferably at least about 50%, or more, than the production in a corresponding wild type algal cell. Optimally, production of an isoprenoid is considered increased according to the invention if production is increased at least about 70%, more optimally at least about 85%, and most optimally 100%.

4-hydroxy-3-methylbut-2-enyl-diphosphate reductase (IDS) refers to a protein having an enzymatic activity of converting 4-hydroxy-3-methylbut-2-enyl-diphosphate into isopentenyl diphosphate and dimethylallyl diphosphate. The IDS protein is also known in the art as HDR. The gene encoding IDS (hereinafter IDS gene) is known in the art as LytB or IspH. Preferably, the IDS is encoded by a coding sequence of a LytB gene.

The term “polynucleotide sequence” refers to a polymeric form of nucleotides of any length, either ribonucleotides or deoxynucleotides. Polynucleotide sequences may include, for example, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The polynucleotide sequences that encode IDS in various algal species is known. FIG. 9 provides some of these polynucleotide sequences, as listed in Table A. Table A lists locations of the genes that encode IDS. The predicted sequence for IDS in the species *Dunaliella salina* is set forth in FIG. 5, i.e., SEQ ID NO:1.

TABLE A

List of algal species including the gene locations for the HDR/IDS genes in each genome.

| Group of Organisms | Algal Species | IDS/HDR genomic location |
|---|---|---|
| Haptophyte | *Emiliana huxleyi* CCMP1516 | Emihu1/scaffold_148:110265-111903 |
| Heterokontophyta | *Aureococcus anophagefferens* | Auran1/scaffold_9:487989-489191 |
| Heterokontophyta, Bacillariophyceae | *Phaeodactylum tricornutum* | Phatr2/chr_4:980823-982163 |
| Heterokontophyta, Bacillariophyceae | *Thalassiosira psuedonana* | Thaps3/chr_5:1227393-1228798 |
| Chlorophyta, Chlorophyceae | *Volvox carteri f. nagariensis* | Volca1/scaffold_5:2446445-2448934 |
| Chlorophyta, Chlorophyceae | *Chlamydomonas reinhardtii* | Chlre3/scaffold_64:375804-380164 |
| Chlorophyta, Trebouxiophyceae | *Chlorella* sp. NC64A | ChlNC64A_1/scaffold_8:1409019-1412156 |
| Chlorophyta, Chlorophyceae | *Chlorella vulgaris* C-169 | Chlvu1/scaffold_12:172678-175481 |

TABLE A-continued

List of algal species including the gene locations for the HDR/IDS genes in each genome.

| Group of Organisms | Algal Species | IDS/HDR genomic location |
|---|---|---|
| Chlorophyceae, Prasinophyceae | *Micromonas pusilla* CCMP1545 | MicpuC2/scaffold_5:373713-375581 |
| Chlorophyceae, Prasinophyceae | *Micromonas strain* RCC299 | MicpuN2/Chr_06:1051378-1052677 |
| Chlorophyceae, Prasionophyceae | *Ostreococcus* RCC809 | OstRCC809_1/scaffold_10:177541-178683 |
| Chlorophyceae, Prasinophyceae | *Ostreococcus tauri* | Ostta4/Chr_08.0001:187586-188956 |
| Chlorophyceae, Prasinophyceae | *Ostreococcus luciminaris* | Ost9901_3/Chr_8:183933-185075 |
| Chlorophyta, Chlorophyceae | *Dunaliella salina* | NA (only cDNA sequence is available) |

Expression of a polynucleotide that encodes IDS can be increased by any genetic engineering means suitable in an algal cell. The term “genetic engineering” or “genetic engineered” as used herein refers to any recombinant DNA or RNA methods used to manipulate a polynucleotide sequence in an algal cell to increase the expression level of an encoded protein in comparison to the level of expression of the protein in a corresponding wild type algal cell. Such genetic engineering methods are described, for example, in Sambrook, J., Fritsch, E. F., Maniatis, T., in: Molecular Cloning (A Laboratory Manual), $2^{nd}$ Edition, Cold Spring Harbor Laboratory Press, 1989.

In one embodiment, the polynucleotide sequence that encodes IDS is genetically engineered to include additional regulatory sequences operationally linked to the polynucleotide sequence. The term “operationally linked” as used herein refers to linkage of a polynucleotide regulatory sequence to a coding sequence such that the regulatory sequence increases transcription of the polynucleotide coding sequence. A “coding sequence” refers to a polynucleotide sequence that encodes a specific amino acid sequence.

A “regulatory sequence” refers to a polynucleotide sequence that controls some aspect of the expression of another polynucleotide sequence. The regulatory sequence may result, for example, in an increase in the transcription of DNA to RNA, or in an increase in translation from RNA to IDS or PDS. Regulatory sequences include, for example, promoters, enhancers, transcription factor binding sites, polyadenylation signals, termination signals, etc. The term “additional” regulatory sequence refers to a regulatory sequence that is in addition to the number and type of regulatory sequences that are typically associated with the corresponding wild type algal cell.

The term “promoter” refers to a polynucleotide sequence located upstream or downstream from the start of transcription of the polynucleotide sequence that encodes the desired end product, i.e., IDS or PDS. A promoter drives expression of an operationally linked polynucleotide sequence and is typically located upstream (5') to a coding sequence. A wide variety of promoters useful for an algal cell is known in the art and may be used to enhance expression of the polynucleotide sequence that encodes IDS or PDS in the algal cell. Examples of suitable promoters include constitutive promoters, inducible promoters, and viral promoters.

The promoter may be derived from the host algal cell, other algal species, or may be obtained from non-algal sources, including bacteria, viruses, yeast, plant, and mammalian cells. The promoter may be constitutive or inducible.

Promoter sequences for an algal cell are preferably isolated from an algal species or a closely related organism. Promoters that are functional in higher plants are less preferred except for groups of algae closely related to higher plants. For example, the 35S CaMV promoter, which is active in many plant species, is completely inactive in *Chlamydomonas* (Day et al. (1990) Physiol. Plantarum 78:254-260).

Specific examples of suitable promoters include hydrogenase promoters, Cytochrome C 6 (Cyc6) promoter, Nial promoter, CabII-1 promoter, Ca1 promoter, Ca2 promoter, coprogen oxidase promoter, algal ribulose bisphosphate carboxylase small subunit gene (SSU) promoter, and algal pyruvate kinase promoter. Additional suitable promoters include the arylsulfatase promoter, and the aminoglycoside 3'-phosphotransferase gene (aphVIII) promoter from the multicellular green alga Volvox, atpA promoter, and RbcS2 promoter which has been widely used to drive gene expression in the nucleus of *C. reinhardii.*

Genetic engineering may further include introducing an expression enhancer operationally linked to a polynucleotide sequence that encodes the desired end product, i.e., IDS or PDS, in order to increase expression of the polynucleotide sequence. An "expression enhancer" refers to a sequence of DNA that functions to increase transcription from nearby promoters. An expression enhancer can be either upstream or downstream to the start of transcription. Examples of suitable expression enhancers include enhancer elements, EE-1 (AGATTTTCACCGGTTGGAAGGAGGT)(SEQ ID NO: 36) and EE-2 (CGACTTACGAA) (SEQ ID NO: 37), as described in Kucho et al. (*Plant Physiol.* 2003 October;133(2):783-93); the GCC-box enhancer element, as described in Wu et al. (*Mol Genet Genomics.* 2001 July;265(5):763-70); and those described in Fischer, et al. (*Mol Genet Genomics.* 2001 July; 265(5):888-94) regarding flanking regions of PsaD.

In another preferred embodiment, at least one additional polynucleotide sequence, and preferably multiple polynucleotide sequences, encoding IDS is functionally introduced into an algal cell. The polynucleotide sequence may, for example, be incorporated in a vector that is then used to functionally introduce the additional polynucleotide sequence into an algal cell.

The introduction of polynucleotide sequences can be either temporary, e.g., by use of vectors, or permanent, e.g., by integration of the entire vector or a fragment thereof into either the nuclear genome, the plastid genome, or the mitochondrial genome of the host alga.

Suitable vectors for increasing expression of the polynucleotide sequence that encodes the desired end product, i.e., IDS or PDS, in an algal cell are known in the art, such as the expression vectors described in U.S. Pat. No. 7,232,679. Such vectors for increasing expression of the polynucleotide sequence that encodes IDS or PDS are incorporated herein by reference. For example, suitable vectors include pBBR-K-mev-op16-1, pBBR-K-mev-op16-2, pDS-mvaA, pDS-idi, pDS-hcs, pDS-mvk, pDS-pmk, pDS-mvd, pDS-His-mvaA, pDS-His-idi, pDS-His-hcs, pDS-His-mvk, pDS-His-pmk, pDS-His-mvd, pBBR-K-Zea4, pBBR-K-Zea4-up, pBBR-K-Zea4-down, pBBR-K-PcrtE-crtE-3, pBBR-tK-PcrtE-mvaA, pBBR-tK-PcrtE-idi, pBBR-tK-PcrtE-hcs, pBBR-tK-PcrtE-mvk, pBBR-tK-PcrtE-pmk, pBBR-tK-PcrtE-mvd, pBBR-K-PcrtE-mvaA-crtE-3, pDS-His-phaA, pBBR-K-PcrtE-crtW, pBBR-K-PcrtE-crtWZ, pBBR-K-PcrtE-crtZW, and combinations thereof Methods and vectors for genetically engineering an algal cell are well known in the art. A person having ordinary skill can readily adapt the known methods and vectors for use in enhancing expression of IDS and PDS in algal cells. See, for example, the disclosure in Melis et al., (U.S. patent application Ser. No. 11/770, 412, specifically Example 1, column 9, paragraph [0092] of US Publication No. 2008/0038805) regarding methods and vectors relating to genetic modification of microalgae to increase expression of Dxs and Dxr genes; Hallmann et al. (*Proc Natl Acad Sci USA.* 1994 Nov 22;91(24):11562-6, specifically page 11563, section "Transformation") regarding methods and vectors relating to genetic modification of Volvox carteri alga to increase expression of a pheromone; and Xue et al, (U.S. Pat. No. 7,081,567, specifically Example 1, Section I-"Culture of *Dunaliella salina*," and Section III-"Introducing Foreign Target Genes into the Cells of *Dunaliella salina*") regarding genetic transformation (functional introduction) techniques that include introducing a foreign target gene into the cells of *Dunaliella salina* and screening the transformed cells of Dunaliella salina. The general methods and vectors for genetic engineering microalgae disclosed in Melis et al., Hallmann et al., and Xue et al. are incorporated herein by reference. For example, the nuclear, mitochondrial, and chloroplast genomes are functionally introduced into algae through a variety of known methods, including by microparticle bombardment, or using glass bead methods.

Method for Increasing Production of Carotenoids

In another aspect, the invention relates to a method for increasing the production level of carotenoids in an algal cell. The method includes increasing expression of a polynucleotide sequence that encodes phytoene desaturases (PDS) in the algal cell.

The term "carotenoid" refers to a compound composed of a polyene backbone that is condensed from five-carbon isoprene unit, and is a member of a class of isoprenoids. Carotenoids can be acyclic or terminated with one (monocyclic) or two (bicyclic) cyclic end groups. The term "carotenoid" may include both carotenes and xanthophylls. A carotene refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as xanthophylls.

Production of a carotenoid is considered increased according to the invention if the production is increased at least about 10%, preferably, at least about 20%, more preferably at least about 30%, even more preferably at least about 40%, and most preferably at least about 50%, or more, than the production in a corresponding wild type algal cell. Optimally, production of a carotenoid is considered increased according to the invention if production is increased at least about 70%, more optimally at least about 85%, and most optimally 100%.

A phytoene desaturase (PDS) refers to a protein having an enzymatic activity of converting phytoene into phytofluene and/or phytofluene into ζ-carotene (zetacarotene) into isopentenyl diphosphate and dimethylallyl diphosphate. The gene encoding PDS is known in the art as crtI.

The polynucleotide sequence that encodes PDS in various algal species is known. FIG. 10 provides some of these polynucleotide sequences, as listed in Table B. Table B lists locations of the genes that encode PDS in the genomes of the various algal species. The predicted sequence for PDS in the species *Dunaliella salina* is set forth in FIG. 5, i.e., SEQ ID NO: 2.

TABLE B

| Location of PDS genes in exemplary algal genomes. | | |
|---|---|---|
| Algae | PDS1 | PDS2 |
| *Micromonas* sp. RCC299 | MicpuN3/Chr_07:126545-128430 | MicpuN3/Chr_10:1133416-1135162 |
| *Micromonas pusilla* CCMP1545 | MicpuC2/scaffold_1:1585868-1587673 | MicpuC2/scaffold_16:22128-24332 |
| *Ostreococcus tauri* | Ostta4/Chr_10.0001:464856-466664 | Ostta4/Chr_16.0001:77361-78983 |
| *Ostreococcus lucimarinus* | 9901_3/Chr_10:488156-489955 | Ost9901_3/Chr_15:64879-66564 |
| *Ostreococus* RCC809 | OstRCC809_1/scaffold_3:868854-870784 | OstRCC809_1/scaffold_8:754092-755669 |
| *Thalassiosira pseudonana* | Thaps3/chr_6:1793806-1795708 | Thaps3/chr_1:1371106-1373101 |
| *Phaeodactylum tricornutum* | Phatr2/chr_8:74943-76736 | Phatr2/chr_24:265288-267343 |
| *Aureococcus anophagefferences* | Auran1/scaffold_1:1218979-1220427 | Auran1/scaffold_3:75201-77110 |
| *Emiliania huxleyi* CCMP1516 | Emihu1/scaffold_328:65825-68598 | Emihu1/scaffold_322:6682-11348 |
| *Dunaliella salina* CCAP1918 | NA (only cDNA sequence is available) | — |

Expression of a polynucleotide that encodes PDS can be increased in an algal cell by any of the same genetic engineering means described above with regard to expression of a polynucleotide that encodes IDS. For example, expression of a polynucleotide that encodes PDS may include genetically engineering a polynucleotide sequence to include a promoter, an expression enhancer, or one or more than one copy of an additional polynucleotide sequence that encodes PDS.

Genetically Engineered Algal Cells

In a further aspect, the invention relates to an algal cell that includes a polynucleotide sequence that is genetically engineered to express a higher level of IDS or PDS than a corresponding wild type algal cell, wherein the cell produces an increased level of isoprenoids than a corresponding wild type algal cell.

The term "algal cell" refers to a eukaryotic cell containing one or multiple plastids. The term "algal cell" also includes cells belonging to the group of cyanophyta. Algae are unicellular or multicellular, photosynthetic, oxygenic, and are organisms without true roots, stems, or leaves. Algae contain chlorophyll and can vary in size from microscopic unicellular forms of smaller than 10 μm (microns) to large macroscopic multi-cellular forms up to dozens of meters long. The algal cell may be from green, blue-green, red, or brown algae. Preferably, the algal cell is a cell from green algae.

The algal cell may be derived from any macroalgae or microalgae organism. The algae can be unicellular or multicellular organisms. In some instances the organism is a rhodophyte, chlorophyte, heterokontophyte, tribophyte, glaucophyte, chlorarachniophyte, euglenoid, haptophyte, cryptomonad, dinoflagellum, or phytoplankton. Algae strains from which the algal cell may be derived include, for example, *Chlamydomonas reinhardtii, Scenedesmus obliquus, Chlorella vulgaris, Botryococcus braunii, Botryococcus sudeticus, Dunaliella salina, Dunaliella bardawil*, and *Haematococcus pluvialis*. Preferably, the algal cell is from *Dunaliella salina* or *Dunaliella bardawil.*

The algal cell may include a polynucleotide sequence that is genetically engineered by any method and means as described above to increase expression of a polynucleotide sequence that encodes IDS or PDS in the algal cell, when compared to a corresponding wild type algal cell. A "wild type algal cell" refers to an algal cell that has not been genetically engineered or treated in an experimental sense or an algal cell that has the characteristics of an algal cell isolated from a naturally occurring source. A "corresponding" wild type algal cell refers to a wild type algal cell that is of the same species as the genetically engineered algal cell.

EXAMPLES

Example 1

Carotenoid Biosynthesis Pathway in *Dunaliella Salina*

A. Biosynthesis Pathway of Isoprenoid Precursors in *Dunaliella Salina*

The biosynthesis pathway of isoprenoid precursors is an important part for all isoprenoid biosynthesis, including carotenoid biosynthesis pathway. *D. salina* CCAP19/18 was grown under different stress conditions. Total RNA was isolated from cells at different times of 0 h, 6 h, 12 h, 24 h, 48 h and 72 h following exposure to stress conditions of high irradiance and/or low nutrient concentration. The total RNA pool was submitted to the Joint Genome Institute (JGI) for generation of cDNA libraries and production of ESTs. For EST generation, cDNA clones were size-fractionated and two libraries were made, one library called CBZT with 2 kb and one termed CBZS with 8 kb. JGI partially sequenced cDNA clones from the 5'UTR and 3'UTR to obtain ESTs which were then used for BLAST analysis with the National Center for Biotechnology Information (NCBI) database. Overall, about 7,725 cDNA clones produced usable EST sequences. The results of matches between the EST sequences and genes in NCBI relating to isoprenoid precursor and carotenoid biosynthesis were documented. Thus most of the genes for isoprenoid precursor biosynthesis were identified by representative ESTs (Table 1): 1-deoxy-D-xylulose5 phosphate synthase (DXS), 2-C-methyl-D-erythritol 4-phosphate synthase (DXR), 4-(cytidine 5_-diphospho)-2-C-methyl-D-erythritol synthase (CMS), 1-hydroxy-2-methyl-2-(E)-butenyl-4-diphosphate synthase (HDS), isopentenyl diphosphate: dimethylallyl diphosphate synthase (IDS), 4-(cytidine 5_-diphospho)-2-C-methyl-D-erythritol kinase (CMK), 2-C-methyl-D-erythritol 2,4-cyclodiphosphate synthase (MCS). Isopentenyl diphosphate:dimethylallyl diphosphate isomerase (IDI) is expected to be found at least two isoforms, one in the plastid and one in the cytosol. The cDNA clone for IDI was not identified in our libraries, but IDI was identified in another library of different stresses of high salt and anaerobic.

The ESTs of IDI gave full length coding sequence, which was translated into the protein. IDI is predicted to contain a chloroplast transit peptide (cTP) of 53 aa using ChloroP predicting program. Therefore, the identified IDI is a predicted to be localized in the plastid. Table 1: Number of cDNA clones encoding enzymes for isoprenoid precusors biosynthesis in *Dunaliella* were identified from EST data. Totally eight genes encoding for the pathway of isoprenoid precursors biosynthesis/ MEP pathway were identified: DXS: 1-deoxy-D-xylulose5 phosphate synthase, DXR: 2-C-methyl-D-erythritol 4-phosphate synthase, CMS: 4-(cytidine 5_-diphospho)-2-C-methyl-D-erythritol synthase, CMK: 4-(cytidine 5_-diphospho)-2-C-methyl-D-erythritol kinase, MCS: 2-C-methyl-D-erythritol 2,4-cyclodiphosphate synthase, HDS: 1-hydroxy-2-methyl-2-(E)-butenyl-4-diphosphate synthase, IDS, isopentenyl diphosphate:dimethylallyl diphosphate synthase, FPPS: Farnesyl Pyrophosphate synthase, GGPS, geranylgeranyl pyrophosphate synthase

*IDI: isopentenyl diphosphate:dimethylallyl diphosphate isomerase, not found in our libraries, but found in libraries of salt stress and anaerobic stress GPS: geranyl pyrophosphate synthase, not found in our libraries

| Number | Enzymes | Number of cDNA clones in the library | |
|---|---|---|---|
| 1 | DXS | 8 | MEP |
| 2 | DXR | 4 | pathway |
| 3 | CMS | 4 | |
| 4 | CMK | 1 | |
| 5 | MCS | 1 | |
| 6 | HDS | 3 | |
| 7 | IDS | 26 | |
| 8 | IDI | * | |

Example 2

B. Biosynthesis Pathway Of Carotenoids in *Dunaliella*

The EST data analysis was extended to investigate genes encoding for enzymes of the carotenoid biosynthesis pathway. Based on the known genes for enzymes found in higher plants, ESTs were identified representing cDNA clones in the library for the following enzymes: Phytoene synthase (PSY), Phytoene desaturase (PDS), ζ-carotene desaturase (ZDS), Carotenoid isomerase (CRTISO), Lycopene ϵ-cyclase (LCYe), Lycopene β-cyclase (LCYb), Zeaxanthin epoxidase (ZEP)(Table 2). β-Carotene hydroxylase (CHYb) was not found in our libraries, but found in libraries of salt stress and anaerobic stress. Analysis of the EST data showed that some of the genes in the pathway were represented by cDNA clones with different sequences: phytoene synthase (PSY), phytoene desaturase (PDS), carotene isomerase (CRTISO), which indicated existence of multiple copies of the genes in the genome of *D. salina*. That multiple cDNA clones coding for PSY were identified for the strain CCAP19/18 confirmed our PCR cloning data and southern blot analysis. The EST data established and confirmed a carotenoid biosynthesis pathway in *Dunaliela* similar to that in higher plants.

Table 2: Number and identity of cDNA clones encoding enzymes for carotenoid biosynthesis identified from EST data of *Dunaliella salina* CCAP19/18. Totally eight genes encoding for the pathway of carotenoid biosynthesis were identified. 12. Phytoene synthase (PSY); 13. Phytoene desaturase (PDS); 14. ZISO, not found in our libraries; 15. ζ-carotene desaturase (ZDS); 16. Carotenoid isomerase (CRTISO); 17. Lycopene □-cyclase (LCYe); 18. Lycopene β-cyclase (LCYb); *19. β-Carotene hydroxylase (CHYb), not found in our libraries, but found in libraries of salt stress and anaerobic stress; 20. Zeaxanthin epoxidase (ZEP)

| Number | Enzymes | Number of cDNA clones from the EST libraries |
|---|---|---|
| 12 | PSY1A | 2 |
| | PSY1B | 1 |
| | PSY2 | 1 |
| 13 | PDS1 | 8 |
| | PDS2 | 2 |
| 14 | ZISO | Not identified |
| 15 | ZDS | 1 |
| 16 | CRT ISO1 | 3 |
| | CRT ISO2 | 2 |
| 17 | LCYe | 2 |
| 18 | LCYb | 3 |
| 19 | CHYb | * |
| 20 | ZEP | 2 |

C. Expression of Genes of the Biosynthesis Pathway of Isoprenoid Precursor and Carotenoid Biosynthesis Pathway in *Dunaliella*

1. Expression of Genes in the Isoprenoid Precursor Biosynthesis Pathway (MEP Pathway) and Prenyl Transferases Isoprenoid precursors are not only the substrates for the carotenoid biosynthesis pathway, but also are substrates for other isoprenoid biosynthesis such as chlorophyll, ubiquinone, gibberellines, cholesterol etc. Because the number of cDNA clones corresponding to one gene in a cDNA library relates directly to the level of the gene's mRNA. The higher the number of cDNA clones corresponding to a given gene, the higher the expression level. The highest number of cDNA clones was found for DXS and IDS indicating that these genes were differentially up-regulated and played important roles under stress conditions (Table 1, FIG. 1).

Figure 2:
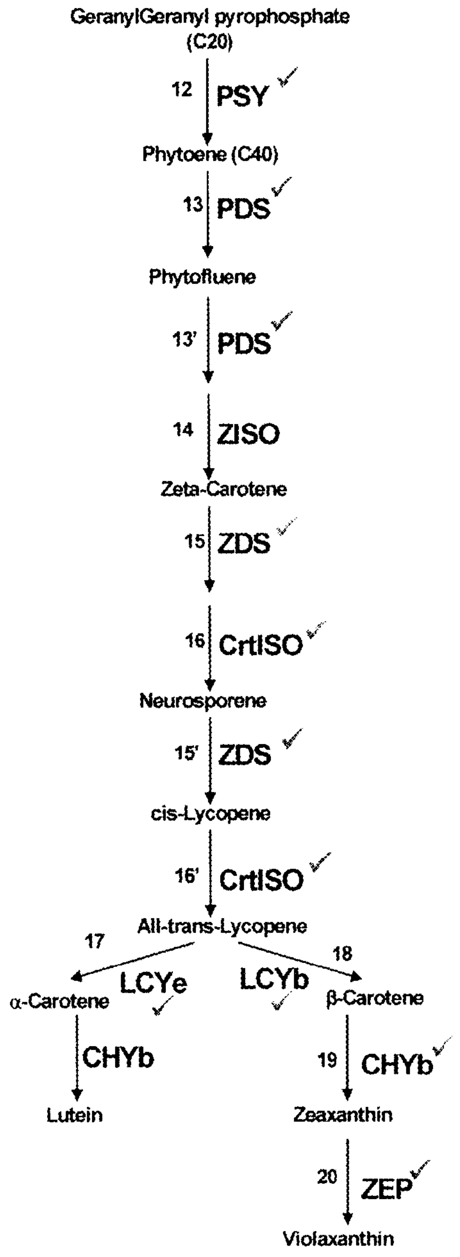
FIG. 2: A schematic diagram for the biosynthesis pathway of carotenoids, which was based on literatures on higher plants. 12. PSY: Phytoene synthase, 13. PDS: Phytoene desaturase, 14. ZDS: zeta-carotene desaturase, 15. ZISO: Zeta-carotene isomerase, 16. CrtIso: Carotene isomerase, 17. LCYe: α-lycopene cyclase, 18. LCYb: β-lycopene cyclase, 19. CHY: carotene hydroxylase, 20. ZEP: zeaxanthin epoxidase. ✓=EST evidence

The result from the EST sequences of genes encoding enzymes for the biosynthesis of isoprenoid precursors confirmed and established the MEP (methylerythritol) pathway for *Dunaliella*, which is one of the important parts for the later carotenoid biosynthesis pathway and biosynthesis other isoprenoids (FIG. 2).

2.Expression of Genes in the Carotenoid Biosynthesis Pathway

As shown earlier, most of the genes for the carotenoid biosynthesis pathway were identified in the EST data libraries. Several of the genes were identified with two different sequences (Table 2) such as phytoene synthase (PSY), phytoene desaturase (PDS).

Figure 3:
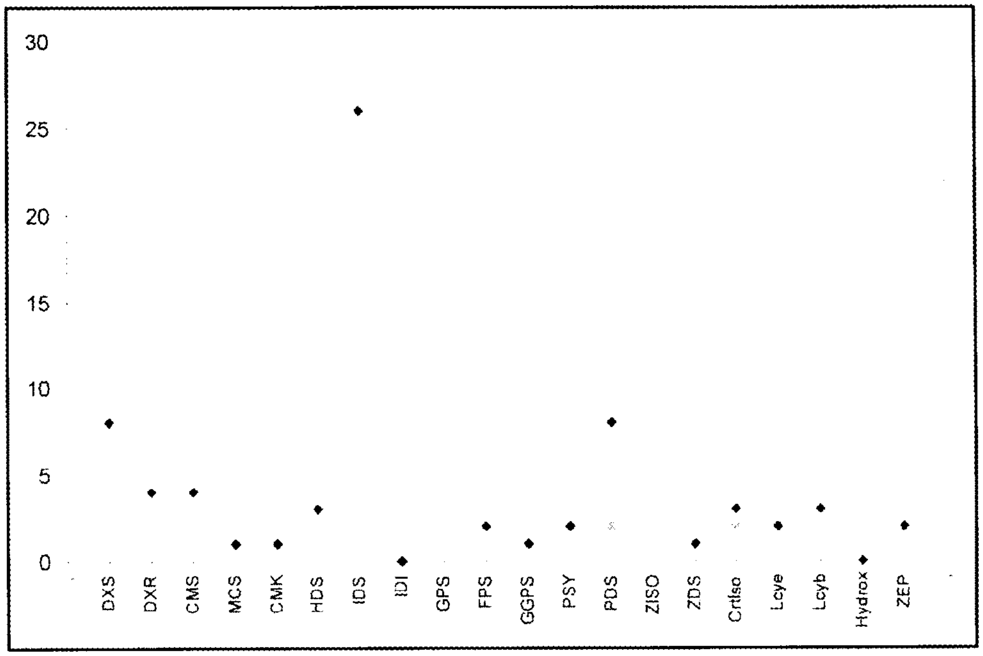
FIG. 3: A diagram showing the number of cDNA clones from *Dunaliella salina* that were identified for genes of MEP pathway, the prenyl transferase and carotenoid biosynthesis pathway. If genes were represented by multiple cDNA clones, it indicated that they were up-regulated under stress conditions and suggested that they played important roles for regulation of metabolic flux through the isoprenoid biosynthesis pathway.
Figure 4:
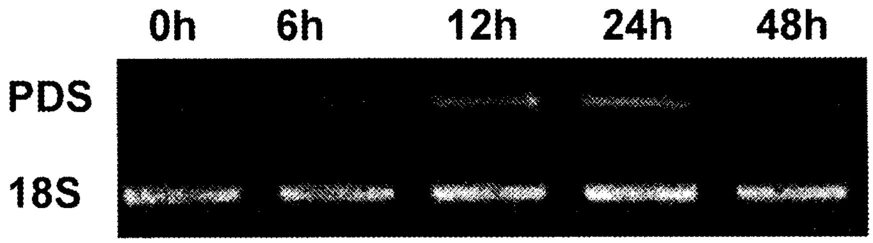
FIG. 4: RT-PCR for the transcriptional expression analysis of the gene phytoene desaturase in *Dunaliella salina* variety *bardawil*. Following a transition from low light (LL) to high light (HL), expression of PDS was followed by RT-PCR analysis. It appears that the expression of PDS strongly increased following transition of growth conditions to high light coinciding with the accumulation of carotene coloring the algal cells orange.

Because abundance of mRNA is directly related to the number of cDNA clones identified for a gene, it indicated that the phytoene desaturase gene with the large number of clones (Table 2, FIG. 3) may be transcriptionally up-regulated under stress conditions, which was then confirmed by RT-PCR expression analysis (FIG. 4).

INCORPORATION OF SEQUENCE LISTING

Incorporated herein by reference in its entirety is the Sequence Listing for the application. The Sequence Listing is disclosed on a computer-readable ASCII text file titled, "sequence listing.txt", created on Oct. 21, 2010. The sequence listing.txt file is 152 kb in size.

What is claimed is:

1. A method for increasing the production level of isoprenoids in an algal cell, said method comprising providing an algal cell introducing at least one polynucleotide that encodes the polypeptide of SEQ ID NO: 3 or a homolog thereof with at least 90% homology thereto into said cell, wherein expression of said polynucleotide sequence is under the control of an inducible regulatory sequence inducing expression of said polynucleotide sequence by inducing said regulatory sequence to increase production level of isoprenoids; and harvesting isoprenoids.

2. The method according to claim 1, wherein said polynucleotide has a sequence that comprises SEQ ID NO. 1.

3. The method according to claim 1, wherein said algal cell is derived from Dunaliella salina or Dunaliella bardawil.

4. The method according to claim 1, wherein the regulatory sequence comprises a promoter.

5. The method according to claim 4, wherein said promoter is selected from the group consisting of hydrogenase promoters, Cytochrome C 6 (Cyc6) promoter, Nial promoter, CabII-1 promoter, Ca1 promoter, Ca2 promoter, coprogen oxidase promoter, algal ribulose bisphosphate carboxylase small subunit gene (SSU) promoter, algal pyruvate kinase promoter, arylsulfatase promoter, aminoglycoside 3'-phosphotransferase gene (aphVIII) promoter, atpA promoter, and RbcS2 promoter.

6. The method according to claim 1, wherein the polynucleotide comprises an expression enhancer.

7. The method according to claim 6, wherein the expression enhancer is selected from the group consisting of EE-1 (AGATTTTCACCGGTTGGAAGGAGGT), (SEQ ID NO. 36), EE-2 (CGACTTACGAA), (SEQ ID NO. 37), and GCC-box enhancer element.

* * * * *

SEQUENCE LISTING

<160> NUMBER OF SEQ ID NOS: 37

<210> SEQ ID NO 1
<211> LENGTH: 2035
<212> TYPE: DNA
<213> ORGANISM: Artificial Sequence
<220> FEATURE:
<223> OTHER INFORMATION: Synthetic nucleotide sequence

<400> SEQUENCE: 1

```
atttaaaggt gaaagcactc atcgtcattc gaagtgatga tgttgtccaa cagcttcaac     60
aagagcgcga ttggtgcagg cctcccaacc gctcaatcac agcccgtcta ccgagtgcca    120
agccgaaccg gcctgcgcgt gagggcaact gtggctgatg agacagcagc cacgcagcag    180
cagcaggagg aggagcgtgg tcgcgaaatt cgccggtccc ttaacaagac gggccgctac    240
gtccggactg tcaaaaacga ccccgacgcg accaaggcgc tggatgcaga cggcgtgggc    300
tactcgctga ccgggctcgt ggcgcagatg cgggaggagg gcaacttttg gaagcagggc    360
gatgtgaccg tcaagctggc caaggcatac ggctactgct ggggcgtgga gcgagccgtg    420
cgcatggctt acgaggcgcg cagggcgttc ccaggccgct ccatccatgt taccaacgaa    480
atcatccaca acccggaagt gaacaggcgc ctgcgcgaaa tggatgtgaa cattgtgaag    540
gaggaccccc aaaagggcaa ggactacagc aagattgaca atggggatgt tgtcatcttc    600
cctgcttttg gggtgggcgc gcctgacatg aagtacttcc gggacaaggg cgtgaacatt    660
gtggacacta cttgcccttg ggtggccaag gtgtggaact ccgttgacac ctatgccaag    720
aaaaagtgca cctcaatcat ccatggcaag tactcgcacg aggagactgt ggccaccgct    780
tcctttgctg aggactacct gatcatcaag gacctcaatg aagcacagta tgtgtgtgac    840
tacatcctga agggcggcga ccgagaggag ttcatgaaga agttctccaa ggccgtctcc    900
aagggctttg accctgatgt ccacctcaac cgcgtgggcc tggccaacca gacgaccatg    960
ctcaagggtg agacccaggc catcggcaag atgctggagc gcaccatgat ggagaaattt   1020
gggcctcaga atctccagga ccacttcatg gtcatggaca ccatctgcga tgccactcag   1080
gaacgccaag atgcgctgta cgagatcact gatgacccta ctattgacat gatgcttgtg   1140
gtgggcggct tcaactcttc caacaccagc cacctacagg aaatccccca caataagggc   1200
ctgcctgcat tctgggtgga cactgccgac cgcattgaca tggccaacaa ctccattgcg   1260
cacaagctgc actacgggga gctcaaggtg acggagaact ggctgcccga gggccccatc   1320
accattggcg ttactagcgg ggcttccaca cccgatcgag cggtggagga ggtgcttgag   1380
cgcgtgttcc gcatgaagga tcccaacttc aagggtatcc agcctaggga atgtgcgccc   1440
cccgtcctgc ccacccacta agcacttgca gtctgtggct tggccaatgc agctgcaata   1500
agcaagtatg gccagctgat atgtgagtgc cctgagggtt tgccctgcaa tgggtgctct   1560
tgcgtttcaa ggtcgaggcc tttcatcctg gggcttgaag ctcaggtggg gagtctcacc   1620
aaacagcttg gtcatactag aatgaagccc ctcgccgtgg tcctcttacc aagcctgcgc   1680
atttgtacat gtactttcgt attattgaat caattgtaca cggattagat caggatattc   1740
caaccggraa aaacttcaat ggtgagcggg taggagaaat gagggagcaa ggagtgtgtt   1800
tgggattttt tgtctcttcg gtctgtgatg aagcaggtcc aaagtcatga gtgggaaaac   1860
atccataatg ttttacaaca cgttggcctt gccagttttg taccataatt ttgtgttttc   1920
cttcaccttg ctttgctaat ctaatccact tgccaacatt tgccacaaac attggcacaa   1980
aatgcagtgg aatcattgtt attgcttaaa tctgggagct aagctcctat aactt        2035
```

<210> SEQ ID NO 2
<211> LENGTH: 1752
<212> TYPE: DNA
<213> ORGANISM: Artificial Sequence
<220> FEATURE:
<223> OTHER INFORMATION: Synthetic nucleotide sequence

<400> SEQUENCE: 2
atgcagacca tgcagggcag ggcacatgct cagacactca acagacagcc tgttacccag 60
gttgccgggc gcacccagag gcgggttggc aggtctcgct tgcaagtgta tgctagggat 120
ttccctcctc ctcagttcga tggcactgcg tcgtaccaag atgctgtggc cctgtccaca 180
aagctgcaaa atgcacctcg gcccgccaag cctcaacgcg tcgtgatcgc cggagccggc 240
ctggctggcc tgtccgcagc caagtacctg tccgatgctg gccacatccc catcgtgttg 300
gaggcccgcg atgtgctggg gggcaaggtg gctgcatgga aggatgagga tggagactgg 360
tacgagactg gcttgcacat cttctttggt gcatacccca acatccagag gctatttaag 420
gagctcaaca tctctgacag gctgcagtgg aagagccact caatgatctt tgccatgcaa 480
gacaagcctg gacagttctc acgctttgag ttcccagaca tccctgcccc ctggaatggt 540
gttgtcgcca tcctgcgcaa taacgagatg ttgtcttgga ctgagaagat taagtttgcc 600
attggcctcc tgcctgccat catcttcggc caaaagtatg tggaggagca ggatgagcta 660
acagtaaccc agtggatgga gaagcagggt gttcctagcc gagtgaacga cgaggtcttc 720
attgccatgg cgaaggccct gaacttcatc gaccctgatg agctttctat gaccgttgtg 780
ctaacagcac tgaaccgttt cctgcaagag cgacatggta gcaagatggc cttccttgat 840
ggtgctcccc cagagcggtt gtgcgaacca atggtgaact acttcacttc caggggcgga 900
gagctgagga tgaatgcacg cctcaagcaa attgtgctga atgaggacaa cagtgtcaag 960
cactttgagc tgctgaatgg agagattgtt gagggagatg cctacatgtc cgctatgcca 1020
gtggacatca tgaagaagct gatgccccag ccctggaaga atgttccctt cttccagaag 1080
ttgaatggcc ttgaaggggt gccagttatc aacatccaca tctggtttga ccgcaagctg 1140
tccacagtgg accacctgct cttctcgcgc tctgagttgc tcagtgtgta tgccgacatg 1200
agcaccacct gtaaagagta ctcagatgac aaggccagca tgcttgagct ggtgtttgca 1260
cctgctgccg actggattgg caggccagat tcagagatcg tggacgcaac catgaaggag 1320
ctcgaaaagc tgttccccaa cgagatcaag gctgaccagt cactggccaa gatccgcaaa 1380
tccaaggtca tcaagacacc cctctcggtc tacaagtcca cagctggacg agagaagtac 1440
aggcccagcc aaaagactcc catccccaac ttctacctgg cgggtgacta caccaagcag 1500
aagtacttgg catctatgga gggtgctgtc ttcagtggca agctggcttg cgagcaggtg 1560
gtagatgatg ctgtcatgcg cgtcggccag cagagcactg cccctagcca gcctgctctg 1620
gctgctgcct ctgctgctgt gctgctggcc atgggcgcag cgcttgcggg caatgcatct 1680
gcccaggtcc tgacagagac catctggggc tccccagtgt tgaccgaggc agtcaccttc 1740
ccttggttct aa 1752

<210> SEQ ID NO 3
<211> LENGTH: 474
<212> TYPE: PRT
<213> ORGANISM: Artificial Sequence
<220> FEATURE:
<223> OTHER INFORMATION: Synthetic peptide sequence -continued

<400> SEQUENCE: 3

```
Met Met Leu Ser Asn Ser Phe Asn Lys Ser Ala Ile Gly Ala Gly Leu
1               5                   10                  15

Pro Thr Ala Gln Ser Gln Pro Val Tyr Arg Val Pro Ser Arg Thr Gly
            20                  25                  30

Leu Arg Val Arg Ala Thr Val Ala Asp Glu Thr Ala Ala Thr Gln Gln
        35                  40                  45

Gln Gln Glu Glu Glu Arg Gly Arg Glu Ile Arg Arg Ser Leu Asn Lys
    50                  55                  60

Thr Gly Arg Tyr Val Arg Thr Val Lys Asn Asp Pro Asp Ala Thr Lys
65                  70                  75                  80

Ala Leu Asp Ala Asp Gly Val Gly Tyr Ser Leu Thr Gly Leu Val Ala
                85                  90                  95

Gln Met Arg Glu Glu Gly Asn Phe Trp Lys Gln Gly Asp Val Thr Val
            100                 105                 110

Lys Leu Ala Lys Ala Tyr Gly Tyr Cys Trp Gly Val Glu Arg Ala Val
        115                 120                 125

Arg Met Ala Tyr Glu Ala Arg Arg Ala Phe Pro Gly Arg Ser Ile His
    130                 135                 140

Val Thr Asn Glu Ile Ile His Asn Pro Glu Val Asn Arg Arg Leu Arg
145                 150                 155                 160

Glu Met Asp Val Asn Ile Val Lys Glu Asp Pro Gln Lys Gly Lys Asp
                165                 170                 175

Tyr Ser Lys Ile Asp Asn Gly Asp Val Val Ile Phe Pro Ala Phe Gly
            180                 185                 190

Val Gly Ala Pro Asp Met Lys Tyr Phe Arg Asp Lys Gly Val Asn Ile
        195                 200                 205

Val Asp Thr Thr Cys Pro Trp Val Ala Lys Val Trp Asn Ser Val Asp
    210                 215                 220

Thr Tyr Ala Lys Lys Lys Cys Thr Ser Ile Ile His Gly Lys Tyr Ser
225                 230                 235                 240

His Glu Glu Thr Val Ala Thr Ala Ser Phe Ala Glu Asp Tyr Leu Ile
                245                 250                 255

Ile Lys Asp Leu Asn Glu Ala Gln Tyr Val Cys Asp Tyr Ile Leu Lys
            260                 265                 270

Gly Gly Asp Arg Glu Glu Phe Met Lys Lys Phe Ser Lys Ala Val Ser
        275                 280                 285

Lys Gly Phe Asp Pro Asp Val His Leu Asn Arg Val Gly Leu Ala Asn
    290                 295                 300

Gln Thr Thr Met Leu Lys Gly Glu Thr Gln Ala Ile Gly Lys Met Leu
305                 310                 315                 320

Glu Arg Thr Met Met Glu Lys Phe Gly Pro Gln Asn Leu Gln Asp His
                325                 330                 335

Phe Met Val Met Asp Thr Ile Cys Asp Ala Thr Gln Glu Arg Gln Asp
            340                 345                 350

Ala Leu Tyr Glu Ile Thr Asp Asp Pro Thr Ile Asp Met Met Leu Val
        355                 360                 365

Val Gly Gly Phe Asn Ser Ser Asn Thr Ser His Leu Gln Glu Ile Pro
    370                 375                 380

His Asn Lys Gly Leu Pro Ala Phe Trp Val Asp Thr Ala Asp Arg Ile
385                 390                 395                 400

Asp Met Ala Asn Asn Ser Ile Ala His Lys Leu His Tyr Gly Glu Leu
                405                 410                 415
```

```
Lys Val Thr Glu Asn Trp Leu Pro Glu Gly Pro Ile Thr Ile Gly Val
            420                 425                 430

Thr Ser Gly Ala Ser Thr Pro Asp Arg Ala Val Glu Glu Val Leu Glu
        435                 440                 445

Arg Val Phe Arg Met Lys Asp Pro Asn Phe Lys Gly Ile Gln Pro Arg
    450                 455                 460

Glu Cys Ala Pro Pro Val Leu Pro Thr His
465                 470


<210> SEQ ID NO 4
<211> LENGTH: 583
<212> TYPE: PRT
<213> ORGANISM: Artificial Sequence
<220> FEATURE:
<223> OTHER INFORMATION: Synthetic peptide sequence

<400> SEQUENCE: 4

Met Gln Thr Met Gln Gly Arg Ala His Ala Gln Thr Leu Asn Arg Gln
1               5                   10                  15

Pro Val Thr Gln Val Ala Gly Arg Thr Gln Arg Arg Val Gly Arg Ser
            20                  25                  30

Arg Leu Gln Val Tyr Ala Arg Asp Phe Pro Pro Pro Gln Phe Asp Gly
        35                  40                  45

Thr Ala Ser Tyr Gln Asp Ala Val Ala Leu Ser Thr Lys Leu Gln Asn
    50                  55                  60

Ala Pro Arg Pro Ala Lys Pro Gln Arg Val Val Ile Ala Gly Ala Gly
65                  70                  75                  80

Leu Ala Gly Leu Ser Ala Ala Lys Tyr Leu Ser Asp Ala Gly His Ile
                85                  90                  95

Pro Ile Val Leu Glu Ala Arg Asp Val Leu Gly Gly Lys Val Ala Ala
            100                 105                 110

Trp Lys Asp Glu Asp Gly Asp Trp Tyr Glu Thr Gly Leu His Ile Phe
        115                 120                 125

Phe Gly Ala Tyr Pro Asn Ile Gln Arg Leu Phe Lys Glu Leu Asn Ile
    130                 135                 140

Ser Asp Arg Leu Gln Trp Lys Ser His Ser Met Ile Phe Ala Met Gln
145                 150                 155                 160

Asp Lys Pro Gly Gln Phe Ser Arg Phe Glu Phe Pro Asp Ile Pro Ala
                165                 170                 175

Pro Trp Asn Gly Val Val Ala Ile Leu Arg Asn Asn Glu Met Leu Ser
            180                 185                 190

Trp Thr Glu Lys Ile Lys Phe Ala Ile Gly Leu Leu Pro Ala Ile Ile
        195                 200                 205

Phe Gly Gln Lys Tyr Val Glu Glu Gln Asp Glu Leu Thr Val Thr Gln
    210                 215                 220

Trp Met Glu Lys Gln Gly Val Pro Ser Arg Val Asn Asp Glu Val Phe
225                 230                 235                 240

Ile Ala Met Ala Lys Ala Leu Asn Phe Ile Asp Pro Asp Glu Leu Ser
                245                 250                 255

Met Thr Val Val Leu Thr Ala Leu Asn Arg Phe Leu Gln Glu Arg His
            260                 265                 270

Gly Ser Lys Met Ala Phe Leu Asp Gly Ala Pro Pro Glu Arg Leu Cys
        275                 280                 285

Glu Pro Met Val Asn Tyr Phe Thr Ser Arg Gly Gly Glu Leu Arg Met
    290                 295                 300
```

Asn Ala Arg Leu Lys Gln Ile Val Leu Asn Glu Asp Asn Ser Val Lys
305 310 315 320

His Phe Glu Leu Leu Asn Gly Glu Ile Val Glu Gly Asp Ala Tyr Met
325 330 335

Ser Ala Met Pro Val Asp Ile Met Lys Lys Leu Met Pro Gln Pro Trp
340 345 350

Lys Asn Val Pro Phe Phe Gln Lys Leu Asn Gly Leu Glu Gly Val Pro
355 360 365

Val Ile Asn Ile His Ile Trp Phe Asp Arg Lys Leu Ser Thr Val Asp
370 375 380

His Leu Leu Phe Ser Arg Ser Glu Leu Leu Ser Val Tyr Ala Asp Met
385 390 395 400

Ser Thr Thr Cys Lys Glu Tyr Ser Asp Asp Lys Ala Ser Met Leu Glu
405 410 415

Leu Val Phe Ala Pro Ala Ala Asp Trp Ile Gly Arg Pro Asp Ser Glu
420 425 430

Ile Val Asp Ala Thr Met Lys Glu Leu Glu Lys Leu Phe Pro Asn Glu
435 440 445

Ile Lys Ala Asp Gln Ser Leu Ala Lys Ile Arg Lys Ser Lys Val Ile
450 455 460

Lys Thr Pro Leu Ser Val Tyr Lys Ser Thr Ala Gly Arg Glu Lys Tyr
465 470 475 480

Arg Pro Ser Gln Lys Thr Pro Ile Pro Asn Phe Tyr Leu Ala Gly Asp
485 490 495

Tyr Thr Lys Gln Lys Tyr Leu Ala Ser Met Glu Gly Ala Val Phe Ser
500 505 510

Gly Lys Leu Ala Cys Glu Gln Val Val Asp Asp Ala Val Met Arg Val
515 520 525

Gly Gln Gln Ser Thr Ala Pro Ser Gln Pro Ala Leu Ala Ala Ala Ser
530 535 540

Ala Ala Val Leu Leu Ala Met Gly Ala Ala Leu Ala Gly Asn Ala Ser
545 550 555 560

Ala Gln Val Leu Thr Glu Thr Ile Trp Gly Ser Pro Val Leu Thr Glu
565 570 575

Ala Val Thr Phe Pro Trp Phe
580

<210> SEQ ID NO 5
<211> LENGTH: 400
<212> TYPE: PRT
<213> ORGANISM: Aureococcus anophagefferens

<400> SEQUENCE: 5

Met Leu Ser Glu Met Lys Ser Glu Met Leu Asp Lys Met Arg Glu Ser
1 5 10 15

Asn Tyr Glu Val Thr Arg Gly Glu Gly Asn Gly Ala Val Thr Phe Thr
20 25 30

Leu Ala Lys Glu Tyr Gly Met Cys Trp Gly Ala Glu Arg Ser Ile Glu
35 40 45

Ile Ala Leu Ala Ala Thr Glu Lys Phe Gly Asp Lys Gln Leu His Ile
50 55 60

Thr Asn Glu Leu Leu His Asn Pro Gly Val Asn Lys Met Leu Glu Asp
65 70 75 80

Glu Gly Val Ser Phe Ile Glu Lys Thr Gly Asp Gly Gly Lys Arg Phe

-continued

```
                85                  90                  95

Asp Asp Val Lys Glu Gly Asp Val Val Ile Leu Pro Ala Phe Gly Ala
            100                 105                 110

Thr Leu Ala Glu Met Gln His Phe Ser Asp Met Gly Val Thr Thr Val
        115                 120                 125

Asp Thr Thr Cys Pro Trp Val Thr Lys Val Trp Asn Val Val Asp Lys
    130                 135                 140

Gln Val Gln Arg Ser Met Thr Thr Ile Ile His Gly Lys Tyr Ala His
145                 150                 155                 160

Glu Glu Ala Ile Ala Thr Ala Ser Met Cys Asp Asp Tyr Leu Met Val
                165                 170                 175

Lys Asn Ile Asp Glu Ala Glu Tyr Val Cys Asn Tyr Met Leu Asn Pro
            180                 185                 190

Thr Pro Glu Gly Arg Glu Asp Leu Leu His Lys Phe Ala Lys Ala Met
        195                 200                 205

Ser Lys Gly Phe Asp Pro Asp Val His Leu Glu Lys Ile Gly Ile Ala
    210                 215                 220

Asn Gln Thr Thr Met Tyr Lys Lys Glu Thr Gln Ala Val Gly Arg Leu
225                 230                 235                 240

Phe Glu Gln Val Ile Leu Lys Lys Tyr Pro Asp Glu Ala Ala Asp Arg
                245                 250                 255

Phe Val Ala Phe Asp Thr Ile Cys Ser Ala Thr Gln Glu Arg Gln Asp
            260                 265                 270

Ala Ile His Glu Met Val Asp Asp Glu Ser Val Lys Asp Leu Asp Phe
        275                 280                 285

Ile Leu Val Val Gly Gly Phe Asp Ser Ser Asn Thr Ala His Leu Val
    290                 295                 300

Glu Ile Pro Tyr Glu Ala Gly Ile Pro Val Phe His Ile Asn Glu Ala
305                 310                 315                 320

Asp Cys Ile Ser Glu Thr Asn Ala Val Ser His Arg Leu Val Ser Gly
                325                 330                 335

Glu Met Ala Val Glu Glu Asn Trp Leu Pro Thr Asp Arg Pro Ala Arg
            340                 345                 350

Ile Gly Val Thr Ser Gly Ala Ser Thr Pro Asp Ala Tyr Val Gln Glu
        355                 360                 365

Ala Leu Glu Arg Leu Val Leu Leu Lys Ser Val Ile Ser Thr Asp Ala
    370                 375                 380

Ala Pro Ala Ala Pro Ala Glu Lys Trp Ala Trp Ser Gly Pro Val Phe
385                 390                 395                 400


<210> SEQ ID NO 6
<211> LENGTH: 465
<212> TYPE: PRT
<213> ORGANISM: Chlamydomonas reinhardtii

<400> SEQUENCE: 6

Met Gln Val Phe Ala Asn Arg Gln Ala Ser Gly Phe Lys Ala Arg Ala
1               5                   10                  15

Glu Arg Pro Ser Arg Ile Ser Arg Val Leu Val Pro Val Val His Ala
            20                  25                  30

Val Ala Ala Glu Thr Lys Gln Val Gly Pro Asp Gly Arg Thr Leu Arg
        35                  40                  45

Arg Ser Leu Asn Gln Thr Gly Arg Tyr Val Arg Gln Pro Thr Asn Asp
    50                  55                  60
```

-continued

```
Pro Ala Ser Gln Val Lys Met Asp Glu His Gly Val Gly Tyr Ser Thr
65                  70                  75                  80

Ser Gly Leu Val Ala Gln Met Arg Thr Gln Asn Asn Leu Trp Lys Glu
                85                  90                  95

Gly Asp Val Thr Val Lys Leu Ala Lys Ala Tyr Gly Tyr Cys Trp Gly
            100                 105                 110

Val Glu Arg Ala Val Arg Met Ala Tyr Glu Ala Arg Leu Ala His Pro
        115                 120                 125

Asp Lys Lys Val Phe Val Thr Asn Glu Ile Ile His Asn Pro Glu Val
    130                 135                 140

Asn Ser Arg Leu Lys Glu Met Asn Ile Glu Ile Val Glu Asp Glu Gly
145                 150                 155                 160

Lys Gly Lys Asp Tyr Ser Met Ile Gly Gly Gly Asp Val Val Ile Phe
                165                 170                 175

Pro Ala Phe Gly Ala Thr Val Gln Glu Leu Thr Asp Phe Lys Glu Lys
            180                 185                 190

Gly Val Gln Met Val Asp Thr Thr Cys Pro Trp Val Ala Lys Val Trp
        195                 200                 205

Asn Ser Val Asp Thr His Thr Arg Lys Gln Tyr Thr Ser Val Ile His
    210                 215                 220

Gly Lys Tyr Ser His Glu Glu Thr Ile Ala Thr Ala Ser Phe Ala Ser
225                 230                 235                 240

Asn Tyr Ile Ile Val Lys Asp Leu Lys Glu Ala Gln Tyr Val Cys Asp
                245                 250                 255

Tyr Ile Leu Gln Gly Gly Asn Arg Glu Glu Phe Leu Gln Lys Phe Ser
            260                 265                 270

Lys Ala Val Ser Ala Gly Phe Asp Pro Glu Thr Met Leu Asp Arg Val
        275                 280                 285

Gly Leu Ala Asn Gln Thr Thr Met Leu Lys Gly Glu Thr Glu Gln Ile
    290                 295                 300

Gly Lys Met Leu Glu Lys Thr Met Leu Thr Lys Tyr Gly Pro Ala Lys
305                 310                 315                 320

Leu Asn Asp His Phe Leu Leu Met Glu Thr Ile Cys Asp Ala Thr Gln
                325                 330                 335

Glu Arg Gln Asp Ala Leu Tyr Glu Met Val Ala Asp Pro Glu Ile Asp
            340                 345                 350

Met Met Ile Val Val Gly Gly Phe Asn Ser Ser Asn Thr Ser His Leu
        355                 360                 365

Gln Glu Ile Ala Glu His Lys Gly Leu Ala Ser Phe Trp Val Asp Ser
    370                 375                 380

Ala Ala Arg Ile Asp Val Glu Lys Asn Val Ile Leu His Lys Leu Ala
385                 390                 395                 400

His Gly Glu Leu Lys Glu Thr Thr Gly Trp Leu Asn Pro Gly Lys Pro
                405                 410                 415

Val Thr Ile Gly Ile Thr Ser Gly Ala Ser Thr Pro Asp Arg Ala Val
            420                 425                 430

Glu Glu Val Leu His Lys Val Phe Lys Ile Tyr Asn Pro Asn Phe Gly
        435                 440                 445

Gly Val Ala Pro Lys Asp Cys Gly Arg Val Ala Thr Pro Asp Glu Glu
    450                 455                 460

His
465
```

<210> SEQ ID NO 7
<211> LENGTH: 472
<212> TYPE: PRT
<213> ORGANISM: Volvox carteri

<400> SEQUENCE: 7

```
Met Gln Thr Thr Lys Thr Ser Arg Lys Ala Ala Phe Thr Gly Ile Lys
1               5                   10                  15

Ser Arg Val His Val Val Val Leu Arg Pro Val Gln Ala Ser Arg Ala
            20                  25                  30

Leu Val Pro Val Val Gln Ser Val Ala Ala Gly Ala Thr Glu Ala Ala
        35                  40                  45

Lys Val Asp Gly Arg Ala Leu Arg Arg Ser Leu Asn Gln Thr Gly Arg
    50                  55                  60

Tyr Val Arg Gln Pro Thr Asn Asp Pro Val Ser Gln Gln Leu Met Asp
65                  70                  75                  80

Glu His Gly Val Gly Tyr Ser Thr Asn Gly Leu Val Ala Gln Met Arg
                85                  90                  95

Asn Asp Gly Asn Ile Trp Lys Gln Gly Thr Val Thr Val Lys Leu Ala
            100                 105                 110

Lys Ala Tyr Gly Tyr Cys Trp Gly Val Glu Arg Ala Val Arg Met Ala
        115                 120                 125

Tyr Glu Ala Arg Gln Ala His Pro Asp Lys Lys Leu Phe Val Thr Asn
    130                 135                 140

Glu Ile Ile His Asn Pro Glu Val Asn Lys Arg Leu Lys Glu Met Asn
145                 150                 155                 160

Ile Glu Ile Ile Glu Asp Glu Gly Asp Gly Lys Asp Tyr Ser Gln Ile
                165                 170                 175

Gly Asn Gly Asp Val Val Ile Phe Pro Ala Phe Gly Ala Thr Val Lys
            180                 185                 190

Glu Leu Ser Asp Phe Arg Asp Lys Gly Val Gln Met Val Asp Thr Thr
        195                 200                 205

Cys Pro Trp Val Ala Lys Val Trp Asn Ser Val Asp Thr His Thr Arg
    210                 215                 220

Lys Gln Tyr Thr Ser Val Ile His Gly Lys Tyr Ser His Glu Glu Thr
225                 230                 235                 240

Ile Ala Thr Ala Ser Phe Ala Ser Asn Tyr Val Ile Val Lys Asp Leu
                245                 250                 255

Lys Glu Ala Gln Tyr Val Cys Asp Tyr Ile Leu His Gly Gly Asn Lys
            260                 265                 270

Glu Glu Phe Leu Ala Lys Phe Ser Lys Ala Val Ser Lys Gly Phe Asp
        275                 280                 285

Pro Asp Thr Met Leu Asp Arg Val Gly Leu Ala Asn Gln Thr Thr Met
    290                 295                 300

Leu Lys Gly Glu Thr Glu Gln Ile Gly Lys Met Leu Glu Ala Thr Met
305                 310                 315                 320

Met Gln Lys Tyr Gly Pro Ala Glu Leu Asn Asn His Phe Leu Leu Met
                325                 330                 335

Glu Thr Ile Cys Asp Ala Thr Gln Glu Arg Gln Asp Ala Leu Tyr Asp
            340                 345                 350

Met Val Ala Asp Pro Glu Val Asp Phe Leu Ile Val Val Gly Gly Phe
        355                 360                 365

Asn Ser Ser Asn Thr Ser His Leu Gln Glu Ile Ala Glu His Lys Gly
    370                 375                 380
```

-continued

```
Leu Pro Ser Phe Trp Val Asp Ser Ala Ala Arg Ile Asp Val Glu Lys
385                 390                 395                 400

Asn Thr Val Leu His Lys Leu Ala His Gly Glu Leu Arg Glu Thr Val
                405                 410                 415

Gly Trp Leu Thr Pro Gly Lys Pro Val Thr Ile Gly Ile Thr Ser Gly
            420                 425                 430

Ala Ser Thr Pro Asp Arg Ala Val Glu Glu Val Leu Ala Lys Val Phe
        435                 440                 445

Lys Ile Tyr Asp Pro Asn Phe Thr Gly Ile Ala Pro Lys Asp Cys Gly
    450                 455                 460

Arg Leu Ala Thr Pro Glu Glu His
465                 470


<210> SEQ ID NO 8
<211> LENGTH: 421
<212> TYPE: PRT
<213> ORGANISM: Chlorella vulgaris

<400> SEQUENCE: 8

Met Asp Asp Ala Glu Ser Leu Ala Leu Met Glu Glu His Gly Val Gly
1               5                   10                  15

Tyr Ser Ser Thr Gly Leu Val Ala Arg Met Arg Ala Asn Gly Asn Leu
            20                  25                  30

Trp Gln Glu Gly Asp Val Lys Val Lys Leu Ala Lys Ala Tyr Gly Tyr
        35                  40                  45

Cys Trp Gly Val Glu Arg Ala Val Gln Met Ala Tyr Glu Ala Arg Lys
    50                  55                  60

Gln Tyr Pro Asn Ser Lys Leu His Val Thr Asn Glu Ile Ile His Asn
65                  70                  75                  80

Pro Ala Thr Val Cys His Asp Gln Arg Leu Lys Glu Met Glu Val Asn
                85                  90                  95

Ile Ile Glu Asp Val Gly Lys Gly Lys Asp Phe Ser Gly Ile Lys Gly
            100                 105                 110

Glu Asp Val Val Ile Leu Pro Ala Phe Gly Ala Ser Trp Gln Glu Met
        115                 120                 125

Lys Met Leu Ser Asp Lys Gly Val Gln Ile Val Asp Thr Thr Cys Pro
    130                 135                 140

Trp Val Ala Lys Val Trp Ser Ala Val Asp Asn Gln Ala Arg Lys Gln
145                 150                 155                 160

His Thr Ser Ile Ile His Gly Lys Tyr Ser His Glu Glu Thr Ile Ala
                165                 170                 175

Thr Ala Ser Phe Ala Thr Thr Tyr Leu Ile Val Arg Asp Ile Pro Glu
            180                 185                 190

Thr Gln Tyr Val Val Asp Tyr Ile Leu Asn Gly Gly Asp Arg Glu Glu
        195                 200                 205

Phe Leu Ala Lys Phe Ser Asn Ala Met Ser Glu Gly Phe Asp Pro Asp
    210                 215                 220

Arg Asp Leu Leu Arg Ile Gly Leu Ala Asn Gln Thr Thr Met Leu Arg
225                 230                 235                 240

Asp Glu Thr Leu Thr Ile Gly Lys Met Leu Glu Lys Thr Met Met Gln
                245                 250                 255

Lys Tyr Gly Pro Ala Glu Leu Lys Asp His Tyr Met Val Leu Asp Thr
            260                 265                 270

Ile Cys Asp Ala Thr Gln Ala Gly Ser Ser Pro Leu Leu Ala Glu Arg
        275                 280                 285
```

```
Gln Asp Ala Val Thr Glu Leu Val Gln Lys Gln Ser Asp Pro Ala Glu
    290                 295                 300

Arg Val Asp Phe Met Leu Val Val Gly Gly Phe Asn Ser Ser Asn Thr
305                 310                 315                 320

Ser His Leu Gln Glu Ile Pro Glu Met Ala Gly Val Pro Ser Phe Trp
                325                 330                 335

Val Asn Ser Ala Ala Cys Val Asp Val Glu His Asn Lys Ile Thr His
            340                 345                 350

Lys Leu Ala His Gly Glu Leu Val Glu Thr Gln Pro Trp Leu Arg Asp
        355                 360                 365

Gly Pro Ile Thr Val Gly Val Thr Ser Gly Ala Ser Thr Pro Asp Arg
    370                 375                 380

Ala Val Glu Glu Val Leu Asp Lys Leu Phe Arg Ile Lys Asp Pro Ser
385                 390                 395                 400

Phe Ser Gly Ile Ala Gln Leu Ser Met Glu Ala Ala Leu Thr Pro Pro
                405                 410                 415

Ser Arg Pro Glu His
            420


<210> SEQ ID NO 9
<211> LENGTH: 505
<212> TYPE: PRT
<213> ORGANISM: Chlorella virus NC64A

<400> SEQUENCE: 9

Met Gln Ser Ala Ala Cys Ala Thr Arg Ser Trp Leu Ala Gly Ser Pro
1               5                   10                  15

Ala Pro Ala Pro Ala Gly Gly Ser Ser Gly Ser Gly Arg Ala Pro Arg
            20                  25                  30

Arg Ala Ala Ala Ala Thr Arg Arg Leu Pro Leu Arg Val Ala Ala Ala
        35                  40                  45

Ala Glu Val Gln Gln Pro Ser Ser Ser Ser Ala Lys Glu Val Leu Glu
    50                  55                  60

Arg Ala Ala Asp Arg Thr Gly Ala Asp Gly Ala Ala Phe Asp Pro Arg
65                  70                  75                  80

Ala Phe Arg Arg Ser Leu Asn Ser Thr Gly Arg Tyr Thr Arg Lys Pro
                85                  90                  95

Ser Asn Asp Pro Asp Ser Leu Ser Leu Met Glu Glu His Gly Val Gly
            100                 105                 110

Tyr Ser Thr Ala Gly Leu Val Ala Gln Met Arg Glu Gln Gly Tyr Ala
        115                 120                 125

Trp Arg Gln Gly Asp Val Asn Val Lys Leu Ala Glu Ala Tyr Gly Phe
    130                 135                 140

Cys Trp Gly Val Glu Arg Ala Val Gln Met Ala Tyr Glu Ala Arg Arg
145                 150                 155                 160

Ala Tyr Pro Gly Gln Arg Leu His Ile Thr Asn Glu Ile Ile His Asn
                165                 170                 175

Pro Ser Val Asn Gln Arg Leu Lys Glu Met Asp Val Gln Phe Ile Asp
            180                 185                 190

Glu Gly Ala Asp Gly Gly Lys Asp Phe Ser Gly Val Lys Glu Gly Glu
        195                 200                 205

Val Val Ile Leu Pro Ala Phe Gly Ala Ser Val Gln Glu Met Arg Leu
    210                 215                 220

Leu Asn Asp Arg Asn Val Gln Ile Val Asp Thr Thr Cys Pro Trp Val
```

-continued

```
225                 230                 235                 240

Ser Lys Val Trp Asn Ala Val Asp Asn Gln Ala Arg Lys Gly His Thr
                245                 250                 255

Ser Ile Ile His Gly Lys Trp Ala His Glu Glu Thr Ile Ala Thr Ala
            260                 265                 270

Ser Phe Ala Gly Thr Tyr Leu Ile Val Lys Asp Leu Lys Glu Ala Gln
        275                 280                 285

Tyr Val Cys Asp Tyr Ile Met His Gly Gly Asp Arg Ala Glu Phe Leu
    290                 295                 300

Ala Lys Phe Glu Asn Ala Met Ser Ala Gly Phe Asp Pro Glu Gln Asp
305                 310                 315                 320

Leu Gln Arg Ile Gly Met Ala Asn Gln Thr Thr Met Leu Lys Gly Glu
                325                 330                 335

Thr Glu Ala Ile Gly Lys Leu Leu Glu Lys Thr Gln Leu Gln Lys Tyr
            340                 345                 350

Gly Pro Gly Glu Leu Ser Gln Arg Phe Met Ile Met Asp Thr Ile Cys
        355                 360                 365

Asp Ala Thr Gln Glu Arg Gln Asp Ala Val Tyr Lys Leu Val Gly Gln
    370                 375                 380

Gln Ser Thr Pro Glu Gly Ile Asp Met Met Leu Val Val Gly Gly Phe
385                 390                 395                 400

Asn Ser Ser Asn Thr Ser His Leu Gln Glu Ile Gly Glu Met Lys Gly
                405                 410                 415

Ile Pro Ser Phe Trp Val Asp Ser Ala Ala Arg Ile Asp Val Gly Ala
            420                 425                 430

Asn Lys Val Thr His Lys Leu Ala His Gly Glu Leu Val Glu Thr Glu
        435                 440                 445

Asn Trp Leu Pro Glu Gly Pro Ile Thr Leu Gly Val Thr Ser Gly Ala
    450                 455                 460

Ser Thr Pro Asp Lys Ala Val Glu Asp Val Leu Asp Arg Val Phe Arg
465                 470                 475                 480

Ile Lys Asp Pro Ser Phe Thr Gly Ile Thr Pro Arg Lys Thr Ser Val
                485                 490                 495

Gln Lys Ala Ala His Gly Glu Glu Glu
            500                 505


<210> SEQ ID NO 10
<211> LENGTH: 429
<212> TYPE: PRT
<213> ORGANISM: Emiliania huxleyi

<400> SEQUENCE: 10

Met Ile Glu Leu Gly Trp Thr Ser Pro Leu Ala Thr Arg Asp Leu Gly
1               5                   10                  15

Arg Thr Ser Ile Glu Ser Arg Leu His Leu Asp Arg Thr Ser Ala Val
            20                  25                  30

Pro Arg Leu Tyr Leu Gly Cys Thr Ala Val Pro Arg Leu Pro Pro Arg
        35                  40                  45

Leu Pro Ser Arg Leu Lys Ala Tyr Pro Asp Lys Arg Met His Ile Thr
    50                  55                  60

Asn Glu Leu Ile His Asn Pro Gly Val Asn Asp Leu Leu Lys Gly Met
65                  70                  75                  80

Asp Ile Glu Phe Met Glu Lys Asp Gly Arg Leu Gly Gly Gly Gly Gly
                85                  90                  95
```

-continued

```
Ala Ser Gly Lys Gly Trp Leu Met Asn Gly His Tyr Val Ile Leu Pro
            100                 105                 110

Ala Phe Gly Ala Ser Leu Glu Glu Met Ser Leu Leu Asp Ala Lys Gly
        115                 120                 125

Val Thr Thr Val Asp Thr Thr Cys Pro Trp Val Ser Lys Val Trp Thr
    130                 135                 140

Thr Val Asp Lys His Gln Leu Ser Glu Met Thr Ser Leu Ile His Gly
145                 150                 155                 160

Lys Tyr Gln His Glu Glu Ala Ile Ala Thr Ala Ser Met Cys Glu Thr
                165                 170                 175

Tyr Leu Ile Ile Lys Asp Met Ala Gln Ala Gln Glu Val Ala Pro Tyr
            180                 185                 190

Ile Leu Asp Glu Gly Leu Val Asp Ser Tyr Glu Glu Phe Met Asp Lys
        195                 200                 205

Tyr Arg Lys Ala Ala Ser Pro His Phe Asp Pro Arg Lys His Leu Lys
    210                 215                 220

Lys Ile Gly Leu Ala Asn Gln Thr Thr Met Tyr Lys Lys Glu Thr Gln
225                 230                 235                 240

Ala Ile Gly Lys Leu Leu Glu Lys Thr Met Met Val Val His Gly Pro
                245                 250                 255

Glu Asn Val Lys His His Phe Ala Ala Phe Asp Thr Ile Cys Asp Ala
            260                 265                 270

Thr Gln Val Arg Gln Asp Ala Val Asn Glu Met Ser Asp Glu Ala Leu
        275                 280                 285

Ala Gly Asp Lys Glu Leu Asp Phe Ile Leu Val Val Gly Gly Trp Asp
    290                 295                 300

Ser Ser Asn Thr Ala His Pro Gly Leu Glu Arg Ser Arg Leu Ser Ala
305                 310                 315                 320

Thr Val Pro Gly Tyr His Val Asn Glu Ala Pro Cys Ile Arg Pro Asp
                325                 330                 335

Asp Thr Arg Phe Val Asp Ser Ala Ile Leu Val Thr Asp Asn Phe Leu
            340                 345                 350

Pro Ser Gly Arg Pro Val Arg Ile Gly Val Thr Ser Gly Ala Ser Thr
        355                 360                 365

Pro Asp Ser Val Val Gln Glu Cys Ile Glu Thr Ile Thr Met Leu Arg
    370                 375                 380

Lys Val Gln Gly Gly Gly Ala Arg Ala Asp Ala Ala Pro Arg Glu Ala
385                 390                 395                 400

Glu Ser Glu Ala Glu Ala Pro Pro Ala Asp Thr Pro Pro Pro Ala Asp
                405                 410                 415

Thr Pro Pro Pro Ala Gly Phe Glu Trp Gly Pro Ala Phe
            420                 425
```

<210> SEQ ID NO 11
<211> LENGTH: 523
<212> TYPE: PRT
<213> ORGANISM: Micromonas pusilla

<400> SEQUENCE: 11

```
Met Ser Val Met Ala Thr Ala Ser Phe Ala Gly Thr Ala Met Pro Leu
1               5                   10                  15

Gly Arg Arg Asn Ala Arg Ala Thr Arg Arg Ala Asn Ala Phe Arg Val
            20                  25                  30

Arg Ala Ala His Asp Glu Glu Glu Pro Glu Glu Lys Ala Asp Ala Gly
        35                  40                  45
```

-continued

```
Phe Lys Phe Asp Pro Ser Ser Tyr Gly Asp Lys Phe Asp Pro Arg Thr
    50                  55                  60

Phe Arg Arg Asp Leu Ser Lys Ser Asp Gln Tyr Asn Arg Arg Phe Ala
65                  70                  75                  80

Lys Asp Lys Glu Ser Ala Glu Arg Met Ala Arg Glu Gly Ile Gly Tyr
                85                  90                  95

Ser Val Gly Ala Ser Arg Leu Asp Arg Ala Thr Ile Ser Arg Ser Leu
            100                 105                 110

Leu Ser Leu Leu Ser Leu Arg Pro Val Pro Ser Arg Tyr Arg Ser Leu
        115                 120                 125

Ala Arg Ala Ile Ala Pro Pro Arg Leu Thr Thr Ala Pro His Arg Thr
    130                 135                 140

Glu Pro Asn Pro Asn Ser Thr Asp Gly Leu Val Ala Lys Met Arg Glu
145                 150                 155                 160

Ser Gly Asn Ser Tyr Val Asp Ala Glu Thr Gly Val Thr Leu Lys Leu
                165                 170                 175

Ala Asp Ala Tyr Gly Phe Cys Trp Gly Val Glu Arg Ala Val Gln Met
            180                 185                 190

Ala Tyr Glu Ala Arg Lys Gln Tyr Pro Asp Ala Lys Leu Trp Ile Thr
        195                 200                 205

Asn Glu Ile Ile His Asn Pro Thr Val Asn Lys Arg Leu Gly Asp Met
    210                 215                 220

Gly Val Asn Phe Ile Glu Glu Thr Lys Asp Gly Lys Asp Phe Ser Gly
225                 230                 235                 240

Val Gly Asn Gly Glu Val Val Ile Leu Pro Ala Phe Gly Ala Ser Val
                245                 250                 255

His Glu Met Lys Leu Leu Ala Glu Lys Gly Ala Ser Ile Val Asp Thr
            260                 265                 270

Thr Cys Pro Trp Val Ser Lys Val Trp Asn Ala Val Asp Ala His Thr
        275                 280                 285

Arg Lys Glu Phe Thr Ser Ile Ile His Gly Lys Trp Ala His Glu Glu
    290                 295                 300

Thr Val Ala Thr Ala Ser Phe Ala Gly Thr Tyr Leu Val Ile Lys Asp
305                 310                 315                 320

Met Lys Glu Ala Thr Tyr Leu Cys Asp Tyr Ile Leu Asn Gly Gly Asp
                325                 330                 335

Lys Glu Glu Phe Met Ala Lys Phe Val Asn Ala His Ser Glu Gly Phe
            340                 345                 350

Asp Pro Asp Val Asp Leu Asp Gly Leu Gly Ile Ala Asn Gln Thr Thr
        355                 360                 365

Met Leu Lys Gly Glu Thr Gln Ala Ile Gly Lys Leu Leu Glu Arg Thr
    370                 375                 380

Met Met Glu Lys His Gly Val Ala Asn Leu Ala Asp His Tyr Met Val
385                 390                 395                 400

Met Asp Thr Ile Cys Asp Ala Thr Gln Glu Arg Gln Asp Ala Met Tyr
                405                 410                 415

Gln Leu Val Glu Asp Lys Pro Asp Met Met Leu Val Val Gly Gly Tyr
            420                 425                 430

Asn Ser Ser Asn Thr Gln His Leu Gln Glu Ile Ser Glu Asp Ala Ser
        435                 440                 445

Val Pro Ser Phe Trp Val Asp Thr Pro Glu Arg Leu Asp Glu Asp Asn
    450                 455                 460
```

-continued

```
Val Ile Ala His Arg Leu Ala His Gly Glu Leu Val Glu Thr Lys Asp
465                 470                 475                 480

Trp Leu Pro Glu Gly Asp Val Val Ile Gly Val Thr Ser Gly Ala Ser
                485                 490                 495

Thr Pro Asp Lys Val Val Glu Asp Val Val Asp Met Ile Phe Lys Thr
            500                 505                 510

Lys Arg Asn Met Lys Thr Ala Thr Pro Ala Arg
        515                 520


<210> SEQ ID NO 12
<211> LENGTH: 380
<212> TYPE: PRT
<213> ORGANISM: Artificial Sequence
<220> FEATURE:
<223> OTHER INFORMATION: Synthetic peptide sequence

<400> SEQUENCE: 12

Met Glu Asp Asp Gly Ile Gly Tyr Ser Lys Ser Gly Leu Val Ala Lys
1               5                   10                  15

Met Arg Glu Ser Gly Asn Val His Val Asp Gly Asp Val Thr Phe Lys
            20                  25                  30

Leu Ala Glu Ala Tyr Gly Phe Cys Trp Gly Val Glu Arg Ala Val Gln
        35                  40                  45

Met Ala Tyr Glu Ala Lys Lys Gln Phe Pro Asp Ala Asn Leu Trp Ile
    50                  55                  60

Thr Asn Glu Ile Ile His Asn Pro Thr Val Asn Asp Arg Leu Gly Glu
65                  70                  75                  80

Met Gly Val Gln Phe Ile Glu Glu Thr Ala Glu Gly Lys Asp Phe Ser
                85                  90                  95

Gly Cys Lys Glu Gly Glu Val Val Ile Leu Pro Ala Phe Gly Ala Ser
            100                 105                 110

Val His Glu Met Lys Leu Leu Asn Asp Lys Gly Val Asn Ile Val Asp
        115                 120                 125

Thr Thr Cys Pro Trp Val Ser Lys Val Trp Asn Ala Val Asp Ala His
    130                 135                 140

Thr Arg Lys Glu Phe Thr Ser Ile Ile His Gly Lys Trp Ala His Glu
145                 150                 155                 160

Glu Thr Ile Ala Thr Ala Ser Phe Ala Lys Thr Tyr Leu Val Val Lys
                165                 170                 175

Asp Met Lys Glu Ala Gln Tyr Val Cys Asp Tyr Val Leu Asp Gly Gly
            180                 185                 190

Asp Arg Glu Glu Phe Leu Ala Lys Phe Lys Asn Ala Tyr Ser Glu Gly
        195                 200                 205

Phe Asp Pro Asp Thr Asp Leu Gly Ala Leu Gly Ile Ala Asn Gln Thr
    210                 215                 220

Thr Met Leu Lys Gly Glu Thr Glu Ala Ile Gly Lys Leu Leu Glu Lys
225                 230                 235                 240

Thr Met Met Gln Lys His Gly Val Asp Lys Leu Asn Asp His Tyr Met
                245                 250                 255

Val Met Asp Thr Ile Cys Asp Ala Thr Gln Glu Arg Gln Asp Ala Met
            260                 265                 270

Tyr Lys Leu Val Asp Asp Lys Pro Asp Met Met Leu Val Val Gly Gly
        275                 280                 285

Phe Asn Ser Ser Asn Thr Ser His Leu Gln Glu Ile Ser Glu Asp Ala
    290                 295                 300
```

-continued

```
Ser Ile Pro Ser Phe Trp Val Asp Thr His Ala Arg Leu Asp Ala Asp
305                 310                 315                 320

Thr Asn Thr Ile Thr His Arg Leu Ala His Gly Glu Leu Val Glu Thr
                325                 330                 335

Lys Asp Trp Leu Pro Ala Gly Lys Val Thr Ile Gly Val Thr Ser Gly
            340                 345                 350

Ala Ser Thr Pro Asp Lys Val Val Glu Asp Val Ile Asp Val Ile Met
        355                 360                 365

Ala Thr Lys Lys Lys Met Ser Gly Ala Pro Ala Arg
    370                 375                 380


<210> SEQ ID NO 13
<211> LENGTH: 380
<212> TYPE: PRT
<213> ORGANISM: Artificial Sequence
<220> FEATURE:
<223> OTHER INFORMATION: Synthetic peptide sequence

<400> SEQUENCE: 13

Met Ala Asn Asp Gly Val Ser Tyr Ser Lys Thr Gly Leu Val Ala Thr
1               5                   10                  15

Met Arg Glu Gly Gly Phe Ala Tyr Ala Ala Asp Gly Leu Thr Phe Lys
            20                  25                  30

Leu Ala Asp Ala Tyr Gly Phe Cys Trp Gly Val Glu Arg Ala Val Gln
        35                  40                  45

Met Ala Tyr Glu Ala Arg Lys Arg Phe Pro Glu Lys Glu Leu Trp Ile
    50                  55                  60

Thr Asn Glu Ile Ile His Asn Pro Thr Val Asn Glu Arg Leu Ser Glu
65                  70                  75                  80

Met Gly Val Arg Phe Ile Arg Glu Thr Glu Ser Asp Gly Lys Asp Phe
                85                  90                  95

Ser Gly Val Arg Glu Gly Asp Val Val Ile Leu Pro Ala Phe Gly Ala
            100                 105                 110

Ser Val His Glu Met Lys Phe Leu Ala Asp Arg Gly Ala Asn Ile Val
        115                 120                 125

Asp Thr Thr Cys Pro Trp Val Ser Lys Val Trp Thr Ala Val Asp Gln
    130                 135                 140

His Lys Arg Lys Glu Phe Thr Ser Ile Ile His Gly Lys Tyr Ser His
145                 150                 155                 160

Glu Glu Thr Val Ala Thr Ala Ser Phe Ala Thr Arg Tyr Leu Ile Val
                165                 170                 175

Lys Asp Met Lys Glu Ala Thr Tyr Val Arg Glu Tyr Ile Leu Asn Gly
            180                 185                 190

Gly Asp Lys Ala Glu Phe Met Gln Lys Phe Lys Asn Ala Met Ser Leu
        195                 200                 205

Gly Phe Asp Pro Asp Asp Asp Leu Glu Gly Val Gly Ile Ala Asn Gln
    210                 215                 220

Thr Thr Met Leu Lys Gly Glu Thr Glu Ala Ile Gly Lys Leu Phe Glu
225                 230                 235                 240

Lys Thr Met Met Glu Lys His Gly Val Glu Asn Ile Ala Asp His Phe
                245                 250                 255

Ile Val Met Asp Thr Ile Cys Asp Ala Thr Gln Glu Arg Gln Asp Ala
            260                 265                 270

Met Tyr Lys Leu Val Asp Glu Glu Pro Asp Ile Met Leu Val Ile Gly
        275                 280                 285
```

-continued

```
Gly Phe Asn Ser Ser Asn Thr Ser His Leu Gln Glu Ile Ser Glu Asp
    290                 295                 300

Lys Ser Ile Pro Ser Tyr Trp Val Asp Thr Cys Asp Arg Met Asn Ala
305                 310                 315                 320

Asp Thr Asn Ser Ile Thr His Lys Leu Ala His Gly Glu Leu Val Gln
                325                 330                 335

Thr Asp Asp Trp Leu Pro Arg Ser Asp Val Val Ile Gly Val Thr Ser
            340                 345                 350

Gly Ala Ser Thr Pro Asp Lys Val Val Glu Asp Val Ile Asp Val Val
        355                 360                 365

Phe Ala Thr Lys Arg Ala Leu Thr Ser Glu Val Ser
    370                 375                 380


<210> SEQ ID NO 14
<211> LENGTH: 409
<212> TYPE: PRT
<213> ORGANISM: Artificial Sequence
<220> FEATURE:
<223> OTHER INFORMATION: Synthetic peptide sequence

<400> SEQUENCE: 14

Met Gln Thr Arg Val Tyr Arg Arg Glu Leu Gly Lys Ser Asp Gln Tyr
1               5                   10                  15

Ser Arg Lys Phe Leu Asn Asp Asp Glu Ala Ala Thr Lys Met Ala Asn
            20                  25                  30

Asp Gly Ile Ser Tyr Ser Lys Ser Gly Leu Val Ala Lys Met Lys Asp
        35                  40                  45

Glu Gly Phe Ala Tyr Val Lys Asp Gly Ile Thr Phe Lys Leu Ala Asp
    50                  55                  60

Ala Tyr Gly Phe Cys Trp Gly Val Glu Arg Ala Val Gln Met Ala Tyr
65                  70                  75                  80

Glu Ala Arg Lys Gln Phe Pro Glu Ser Lys Leu Trp Ile Thr Asn Glu
                85                  90                  95

Ile Ile His Asn Pro Thr Val Asn Glu Arg Leu Ser Asp Met Gly Val
            100                 105                 110

Asn Phe Ile Glu Glu Ser Glu Asn Gly Lys Asp Phe Ser Gly Val Gln
        115                 120                 125

Ser Gly Glu Val Val Ile Leu Pro Ala Phe Gly Ala Ser Val His Glu
    130                 135                 140

Met Lys Phe Leu Ala Asp Arg Gly Ala Asn Ile Val Asp Thr Thr Cys
145                 150                 155                 160

Pro Trp Val Ser Lys Val Trp Asn Ala Val Asp Thr His Lys Arg Lys
                165                 170                 175

Glu Phe Thr Ser Ile Ile His Gly Lys Tyr Ser His Glu Glu Thr Val
            180                 185                 190

Ala Thr Ala Ser Phe Ala Thr Thr Tyr Leu Ile Val Lys Asp Met Thr
        195                 200                 205

Glu Ala Glu Tyr Val Arg Asp Tyr Ile Met Asn Gly Gly Asp Lys Ala
    210                 215                 220

Glu Phe Met Glu Lys Phe Lys Asn Ala Met Ser Glu Gly Phe Asp Pro
225                 230                 235                 240

Asp Glu Asp Leu Asn Gly Val Gly Ile Ala Asn Gln Thr Thr Met Leu
                245                 250                 255

Lys Gly Glu Thr Glu Ala Ile Gly Lys Leu Phe Gln Gln Thr Met Met
            260                 265                 270
```

-continued

```
Glu Lys Phe Gly Val Glu Asn Ala Asp Gln His Phe Val Val Met Asp
        275                 280                 285

Thr Ile Cys Asp Ala Thr Gln Glu Arg Gln Asp Ala Met Tyr Lys Leu
    290                 295                 300

Val Asp Asp Lys Pro Asp Ile Met Leu Val Val Gly Gly Phe Asn Ser
305                 310                 315                 320

Ser Asn Thr Ser His Leu Gln Glu Ile Ala Glu Asp Lys Ser Ile Pro
                325                 330                 335

Ser Tyr Trp Val Asp Thr Ala Glu Arg Leu Asp Pro Ser Lys Asn Ser
            340                 345                 350

Ile Thr His Lys Leu Ala His Gly Glu Leu Val Thr Thr Asp Ala Trp
        355                 360                 365

Leu Pro Ala Ser Asp Val Val Ile Gly Ile Thr Ser Gly Ala Ser Thr
    370                 375                 380

Pro Asp Lys Val Val Glu Asp Val Ile Asp Val Val Phe Ala Thr Lys
385                 390                 395                 400

Thr Ala Leu Lys Ser Ala Val Ser Arg
                405


<210> SEQ ID NO 15
<211> LENGTH: 380
<212> TYPE: PRT
<213> ORGANISM: Artificial Sequence
<220> FEATURE:
<223> OTHER INFORMATION: Synthetic peptide sequence

<400> SEQUENCE: 15

Met Ala Asn Asp Gly Ile Ser Tyr Ser Lys Thr Gly Leu Val Ala Lys
1               5                   10                  15

Met Lys Glu Asn Gly Leu Ser Tyr Val Glu Asp Gly Ile Thr Phe Lys
            20                  25                  30

Leu Ala Asp Ala Tyr Gly Phe Cys Trp Gly Val Glu Arg Ala Val Gln
        35                  40                  45

Met Ala Tyr Glu Ala Arg Lys Gln Phe Pro Glu Ala Lys Leu Trp Ile
    50                  55                  60

Thr Asn Glu Ile Ile His Asn Pro Thr Val Asn Asp Arg Leu Ser Glu
65                  70                  75                  80

Met Gly Val Asn Phe Val Glu Glu Thr Ser Asp Gly Lys Asp Phe Ser
                85                  90                  95

Gly Val Lys Arg Gly Glu Val Val Ile Leu Pro Ala Phe Gly Ala Ser
            100                 105                 110

Val His Glu Met Lys Phe Leu Ala Asp Lys Gly Ala Asn Ile Val Asp
        115                 120                 125

Thr Thr Cys Pro Trp Val Ser Lys Val Trp Asn Ala Val Asp Thr His
    130                 135                 140

Lys Arg Lys Asp Phe Thr Ser Ile Ile His Gly Lys Tyr Ser His Glu
145                 150                 155                 160

Glu Thr Val Ala Thr Ala Ser Phe Ala Thr Thr Tyr Leu Ile Val Lys
                165                 170                 175

Asp Met Arg Glu Ala Asn Tyr Val Arg Asp Tyr Ile Leu Lys Gly Gly
            180                 185                 190

Asp Lys Ala Glu Phe Met Glu Lys Phe Lys Asn Ala Met Ser Gln Gly
        195                 200                 205

Phe Asp Pro Asp Glu Asp Leu Asp Gly Val Gly Ile Ala Asn Gln Thr
    210                 215                 220
```

-continued

Thr Met Leu Lys Gly Glu Thr Glu Ala Ile Gly Lys Leu Phe Gln Ser
225 230 235 240

Thr Met Met Glu Lys Phe Gly Val Glu Asn Val Asp Gln His Phe Val
245 250 255

Val Met Asp Thr Ile Cys Asp Ala Thr Gln Glu Arg Gln Asp Ala Met
260 265 270

Tyr Lys Leu Val Asp Ala Lys Pro Asp Ile Met Leu Val Val Gly Gly
275 280 285

Leu Asn Ser Ser Asn Thr Gln His Leu Gln Glu Ile Ser Glu Asp Lys
290 295 300

Ala Ile Pro Ser Tyr Trp Val Asp Thr Ala Asp Arg Leu Asn Ala Asp
305 310 315 320

Thr Asn Ser Ile Ser His Lys Leu Ala His Gly Glu Leu Val Thr Thr
325 330 335

Asp Gly Trp Leu Pro Ala Gly Asp Val Val Ile Gly Ile Thr Ser Gly
340 345 350

Ala Ser Thr Pro Asp Lys Val Val Glu Asp Val Met Asp Val Val Phe
355 360 365

Ala Thr Lys Arg Ala Leu Glu Ser Ala Val Ser Arg
370 375 380

<210> SEQ ID NO 16
<211> LENGTH: 401
<212> TYPE: PRT
<213> ORGANISM: Phaeodactylum tricornutum

<400> SEQUENCE: 16

Met Lys Ser Asp Arg Phe His Arg Arg Gly Phe Lys Glu Val Arg Glu
1 5 10 15

Gly Val Glu Ser Asn Met Glu Asp Gln Phe Gln Ser Pro Ile Val Asn
20 25 30

Ser Leu Arg Thr Ser Asn Phe Val Met Asp Arg Asp Gly Val Lys Val
35 40 45

Tyr Leu Ala Lys Asp Phe Gly Phe Cys Trp Gly Val Glu Arg Ser Ile
50 55 60

Ala Leu Ala Tyr Glu Ala Ala Glu His Phe Pro Asp Arg Lys Leu His
65 70 75 80

Ile Thr Asn Glu Leu Ile His Asn Pro Glu Val Asn Glu Asn Leu Lys
85 90 95

Ala Lys Asn Val Gln Phe Ile Glu Lys Leu Gly Asp Gly Thr Lys Asn
100 105 110

Phe Ala Ser Val Gln Asp Gly Asp Val Val Ile Leu Pro Ala Phe Gly
115 120 125

Ala Ser Phe Glu Glu Met Asp Tyr Phe Asp Lys Lys Asn Val Glu Ile
130 135 140

Val Asp Thr Thr Cys Pro Trp Val Ser Lys Val Trp Asn Thr Val Asp
145 150 155 160

Lys His Gln Lys Gln Gly Leu Thr Ser Val Ile His Gly Lys Tyr Ala
165 170 175

His Glu Glu Thr Val Ala Thr Thr Ser Phe Cys Glu Asp Phe Ile Cys
180 185 190

Val Lys Asn Phe Lys Glu Ala Glu Met Val Ala Asn Tyr Ile Leu Asn
195 200 205

Gly Gly Asp Lys Asp Ala Phe Met Lys His Phe Glu Asn Ala Val Ser
210 215 220

```
Glu Gly Phe Asp Pro Asp Lys His Leu Glu Lys Val Gly Leu Ala Asn
225                 230                 235                 240

Gln Thr Thr Met Tyr Lys Lys Glu Thr Arg Ala Ile Gly Gln Leu Phe
                245                 250                 255

Gln Lys Thr Met Met Lys Lys Phe Gly Pro Val Lys Ser Lys Glu His
            260                 265                 270

Tyr Met Glu Phe Asp Thr Ile Cys Asp Ala Thr Gln Glu Arg Gln Asp
        275                 280                 285

Ala Ile His Asp Met Val Glu Ser Ala Gln Lys Asp Gly Leu Asp Phe
    290                 295                 300

Ile Leu Val Ile Gly Gly Trp Asp Ser Ser Asn Thr Ala His Leu Leu
305                 310                 315                 320

Glu Ile Pro Val His Ala Gly Ile Arg Ala Phe His Ile Asn Arg Ala
                325                 330                 335

Glu Cys Ile Gly Ala Asp Asn Thr Ile Thr His Arg Thr Val Asp Gly
            340                 345                 350

Glu Ile Val Thr Thr Gln Leu Leu Glu Asp Met Asp Lys Glu Val Val
        355                 360                 365

Met Gly Val Thr Ser Gly Ala Ser Thr Pro Asp Ala Ala Val Gln Asp
    370                 375                 380

Ser Leu Ser Gln Ile Phe Leu Leu Lys Lys Met Tyr Asp Glu Ser Lys
385                 390                 395                 400

Lys


<210> SEQ ID NO 17
<211> LENGTH: 382
<212> TYPE: PRT
<213> ORGANISM: Thalassiosira pseudonana

<400> SEQUENCE: 17

Met Glu Asp Gln Phe Lys Ser Ser Leu Val Asp Glu Leu Lys Thr Asn
1               5                   10                  15

Asp Phe Val Ile Glu Lys Asp Gly Val Lys Val Tyr Leu Ala Lys Asp
            20                  25                  30

Phe Gly Phe Cys Trp Gly Val Glu Arg Ser Ile Ala Leu Ala Tyr Glu
        35                  40                  45

Ala Val Glu His Phe Pro Gly Lys Thr Val His Ile Thr Asn Glu Leu
    50                  55                  60

Ile His Asn Pro Glu Val Asn Asp Lys Leu His Asp Met Asn Val Gln
65                  70                  75                  80

Phe Ile Glu Lys Leu Gly Glu Gly Lys Lys Asp Phe Ser Lys Ile Gly
                85                  90                  95

Glu Gly Asp Val Val Ile Leu Pro Ala Phe Gly Ala Ser Phe Glu Glu
            100                 105                 110

Met Thr Leu Met Asn Asn Lys Asn Val Glu Val Val Asp Thr Thr Cys
        115                 120                 125

Pro Trp Val Ser Lys Val Trp Asn Thr Val Asp Gln His Gln Arg Lys
    130                 135                 140

Gly Leu Thr Ser Val Ile His Gly Lys Tyr Gly His Glu Glu Thr Val
145                 150                 155                 160

Ala Thr Val Ser Phe Cys Glu Asp Tyr Ile Cys Val Lys Asp Ile Lys
                165                 170                 175

Glu Ala Glu Met Val Ala Asp Tyr Ile Ile Asn Gly Gly Asp Lys Glu
            180                 185                 190
```

```
Lys Phe Leu Lys Tyr Phe Glu Lys Ala Val Ser Lys Gly Phe Asp Pro
        195                 200                 205

Asp Thr Met Leu Asp Lys Val Gly Leu Ala Asn Gln Thr Thr Met Tyr
    210                 215                 220

Lys Lys Glu Thr Arg Ala Ile Gly Gln Leu Met Gln Lys Ala Met Met
225                 230                 235                 240

Lys Lys Phe Gly Pro Val Asn Ala Lys Asp His Tyr Leu Glu Phe Asp
                245                 250                 255

Thr Ile Cys Asp Ala Thr Gln Glu Arg Gln Asp Ala Ile Ser Asp Leu
            260                 265                 270

Val Glu Asn Ser Asp Glu Leu Gly Leu Asp Phe Ile Leu Val Val Gly
        275                 280                 285

Gly Trp Asp Ser Ser Asn Thr Ala His Leu Leu Glu Ile Pro Glu Lys
    290                 295                 300

Ala Gly Val Arg Ser Phe His Ile Asn Lys Ser Glu Cys Ile Gly Ala
305                 310                 315                 320

Asp Asn Thr Ile Thr His Arg Thr Val Asp Gly Glu Ile Val Thr Glu
                325                 330                 335

Lys Phe Ile Glu Asp Ile Glu Asn Lys Asp Lys Lys Leu Val Met Gly
            340                 345                 350

Val Thr Ser Gly Ala Ser Thr Pro Asp Lys Ala Val Gln Asp Ser Leu
        355                 360                 365

Asp Gln Ile Phe Met Leu Lys Lys Val Tyr Ser Lys Glu Glu
    370                 375                 380


<210> SEQ ID NO 18
<211> LENGTH: 604
<212> TYPE: PRT
<213> ORGANISM: Artificial Sequence
<220> FEATURE:
<223> OTHER INFORMATION: Synthetic peptide sequence

<400> SEQUENCE: 18

Met Ser Ala Leu Ser Ser Arg Ala Ala Val Gly Gln Arg Val Arg Ala
1               5                   10                  15

Arg Val Ala Val Pro Ser Ala Thr Ser Pro Ser Ser Arg Arg Pro Leu
            20                  25                  30

Arg Val Val Ala Glu Asp Phe Pro Gln Pro Ala Gln Ile Lys Asn Thr
        35                  40                  45

Asp Asn Tyr Arg Asp Gly Glu Ala Leu Ser Lys Lys Phe Lys Glu Leu
    50                  55                  60

Lys Gly Met Gly Glu Lys Lys Lys Val Val Ile Val Gly Gly Gly Leu
65                  70                  75                  80

Ser Gly Leu Ala Cys Ala Lys Tyr Leu Val Asp Ala Gly His Glu Pro
                85                  90                  95

Ile Val Leu Glu Gly Arg Asp Val Leu Gly Gly Lys Val Ser Ala Trp
            100                 105                 110

Lys Asp Lys Asp Gly Asp Trp Ile Glu Thr Gly Leu His Ile Phe Phe
        115                 120                 125

Gly Ala Tyr Pro Asn Met Met Asn Leu Phe Ala Glu Leu Asp Ile Glu
    130                 135                 140

Asp Arg Leu Gln Trp Lys Val His Lys Met Ile Phe Ala Met Gln Glu
145                 150                 155                 160

Leu Pro Gly Glu Phe Thr Thr Phe Asp Phe Val Lys Gly Ile Pro Ala
                165                 170                 175
```

-continued

```
Pro Leu Asn Phe Gly Leu Ala Ile Leu Leu Asn Gln Lys Met Leu Thr
            180                 185                 190

Leu Gly Glu Lys Leu Gln Thr Ala Pro Pro Leu Ile Pro Met Leu Ile
        195                 200                 205

Glu Gly Gln Asp Phe Ile Asp Glu Gln Asp Glu Leu Ser Val Leu Asp
    210                 215                 220

Phe Met Arg Lys Tyr Gly Met Pro Asp Arg Ile Asn Glu Glu Val Phe
225                 230                 235                 240

Ile Ser Met Ala Lys Ala Leu Asp Phe Ile Asp Pro Asp Lys Leu Ser
                245                 250                 255

Met Thr Val Val Leu Thr Ala Met Asn Arg Phe Leu Asn Glu Thr Asp
            260                 265                 270

Gly Leu Gln Met Ala Phe Leu Asp Gly Asn Gln Pro Asp Arg Leu Cys
        275                 280                 285

Ala Pro Met Val Asp His Ile Lys Ala Gly Gly Gly Asp Val Lys Leu
    290                 295                 300

Lys Gln Arg Val Lys Glu Phe Val Leu Asn Asp Asp Gly Ser Val Lys
305                 310                 315                 320

Cys Leu Lys Met Val Ser Gly Glu Glu Ile Val Ala Asp Glu Tyr Val
                325                 330                 335

Ser Ala Val Pro Val Asp Ile Met Lys Arg Met Met Pro Lys Gln Trp
            340                 345                 350

Gly Thr Met Pro Phe Phe His Gln Ile Gln Glu Leu Glu Gly Ile Pro
        355                 360                 365

Val Ile Asn Ile His Leu Trp Phe Asp Arg Lys Leu Lys Asn Val Asp
    370                 375                 380

His Leu Cys Phe Ser Arg Ser Pro Leu Leu Ser Val Tyr Ala Asp Met
385                 390                 395                 400

Ser Thr Thr Cys Lys Glu Tyr Tyr Asp Glu Glu Lys Ser Met Leu Glu
                405                 410                 415

Leu Val Phe Ala Pro Cys Ser Pro Leu Ala Gly Gly Lys Thr Asn Trp
            420                 425                 430

Ile Ala Lys Ser Asn Glu Glu Ile Val Glu Ala Thr Met Lys Glu Leu
        435                 440                 445

Glu Arg Leu Phe Pro Leu Glu Ile Gly Pro Lys Ser Pro Asp Gly Val
    450                 455                 460

Gly Ala Lys Leu Leu Lys His Ala Val Val Lys Thr Pro Arg Ser Val
465                 470                 475                 480

Tyr Ala Ala Ile Pro Gly Arg Asn Lys Tyr Arg Pro Ser Gln Ala Thr
                485                 490                 495

Pro Ile Ser Asn Phe Thr Leu Ala Gly Asp Trp Thr Ser Gln Lys Phe
            500                 505                 510

Leu Gly Ser Met Glu Gly Ala Val Leu Ala Gly Lys Leu Ala Ala Glu
        515                 520                 525

Val Val Thr Asp Lys Ala Val Tyr Gly Ala Pro Thr Lys Gly Leu Lys
    530                 535                 540

Lys Ile Val Pro Asp Val Ile Ala Glu Ala Arg Lys Leu Gln Glu Lys
545                 550                 555                 560

Glu Pro Val Gly Val Thr Gly Glu Ser Glu Val Ser Phe Gly Gly Gly
                565                 570                 575

Cys Val Met Glu Asp Ala Asp Glu Lys Glu Leu Ala Val Leu Asp Pro
            580                 585                 590
```

```
Glu Gln Met Val Lys Leu Glu Gly Ala Pro Ala Arg
        595                 600


<210> SEQ ID NO 19
<211> LENGTH: 559
<212> TYPE: PRT
<213> ORGANISM: Artificial Sequence
<220> FEATURE:
<223> OTHER INFORMATION: Synthetic peptide sequence

<400> SEQUENCE: 19

Met Ser Ala Ala Ile Arg Ala Val Ser Thr Leu Pro Ser Ser Thr Thr
1               5                   10                  15

Arg Thr Leu Ser Gly Gln Lys Arg His Arg His Arg Arg Arg Phe Ala
            20                  25                  30

Arg Ser Ser Ser Leu Arg Ala Val Ala Gly Asp Phe Pro Thr Pro Asp
        35                  40                  45

Leu Asp Lys Pro Gly Asn Ala Asn Tyr Gln Glu Ala Lys Ala Leu Ser
    50                  55                  60

Ala Lys Leu Ala Gly Asn Ala Ala Ser Val Gly Ala Ser His Glu Pro
65                  70                  75                  80

Lys Arg Val Val Val Val Gly Gly Gly Leu Ala Gly Leu Ser Cys Ala
                85                  90                  95

Lys Tyr Leu Ala Asp Ala Gly His Val Pro Val Val Leu Glu Arg Gly
            100                 105                 110

Asp Val Leu Gly Gly Lys Val Ser Ala Trp Gln Asp Glu Asp Gly Asp
        115                 120                 125

Trp Ile Glu Thr Gly Leu His Ile Phe Phe Gly Ala Tyr Pro Asn Met
    130                 135                 140

Met Asn Leu Phe Lys Glu Leu Gly Ile Glu Asp Arg Leu Gln Trp Lys
145                 150                 155                 160

Glu His Ala Met Thr Phe Ala Met Gln Asp Tyr Pro Gly Glu Phe Thr
                165                 170                 175

Lys Phe Tyr Phe Pro Pro Asn Leu Pro Ala Pro Phe Asn Met Ala Tyr
            180                 185                 190

Ala Ile Leu Thr Asn Asp Lys Met Leu Thr Trp Thr Glu Lys Leu Arg
        195                 200                 205

Thr Gly Ile Pro Leu Val Pro Met Leu Leu Gly Gly Gln Glu Tyr Ile
    210                 215                 220

Asn Ala Gln Asp Glu Leu Ser Val Gln Gln Trp Met Arg Lys Asn Phe
225                 230                 235                 240

Met Pro Glu Arg Val Arg Glu Glu Leu Phe Ile Ala Met Gly Lys Ala
                245                 250                 255

Leu Asp Phe Ile Asp Ser Asp Lys Leu Ser Met Thr Val Ile Leu Thr
            260                 265                 270

Ala Met Asn Arg Phe Ile Asn Glu Thr His Gly Ser Lys Thr Ala Phe
        275                 280                 285

Leu Asp Gly Asn Gln Pro Asp Arg Leu Cys Ala Pro Met Ala Lys His
    290                 295                 300

Val Glu Thr Val Ala Gly Gly Glu Val Arg Thr Lys Ala Gly Leu Lys
305                 310                 315                 320

Arg Ile Leu Val Asp Glu Thr Thr Gly Asp Val Thr Gly Met Glu Leu
                325                 330                 335

Ile Gly Gly Glu Val Val Thr Gly Asp His Tyr Val Ser Ala Met Pro
            340                 345                 350
```

```
Val Asp Ala Leu Lys Leu Leu Leu Pro Asp Val Trp Lys Pro Asp Pro
        355                 360                 365

Phe Phe Lys Gln Leu Glu Glu Leu Glu Gly Ile Pro Val Ile Asn Val
    370                 375                 380

His Ile Trp Phe Asp Arg Lys Leu Arg Pro Tyr Asp Gly Leu Val Phe
385                 390                 395                 400

Ser Arg Ser Pro Leu Leu Ser Val Tyr Ala Asp Met Ser Glu Cys Cys
                405                 410                 415

Lys Glu Tyr Ala Ser Asp Asp Thr Ser Met Leu Glu Leu Val Phe Ala
            420                 425                 430

Pro Cys Ser Lys Glu Ala Gly Ser Asp Val Asn Trp Ile Gly Lys Ser
        435                 440                 445

Asp Glu Glu Ile Val Gln Ala Thr Leu Gly Glu Leu Glu Arg Leu Phe
    450                 455                 460

Pro Asp Glu Ile Ala Ala Asp Gly Ser Lys Ala Lys Val Val Lys His
465                 470                 475                 480

Ala Val Val Lys Thr Pro Arg Ser Val Tyr Ala Ala Val Pro Gly Arg
                485                 490                 495

Asn Lys Phe Arg Pro Ser Gln Asn Thr Pro Val Lys Asn Phe Thr Leu
            500                 505                 510

Ala Gly Asp Phe Thr Tyr Gln Lys Phe Leu Gly Ser Met Glu Gly Ala
        515                 520                 525

Val Leu Ser Gly Lys Leu Ala Ala Glu Val Val Ala Asp Lys Met Ala
    530                 535                 540

Gly Arg Glu Ala Lys Pro Val Lys Glu Val Val Ala Arg Tyr Arg
545                 550                 555


<210> SEQ ID NO 20
<211> LENGTH: 601
<212> TYPE: PRT
<213> ORGANISM: Micromonas pusilla

<400> SEQUENCE: 20

Met Thr Ala Arg Arg Val Ala Gln Ser Arg Val Ala Pro Ala Ala Ala
1               5                   10                  15

Ser Arg Ala Arg Ala Leu Arg Val Val Ala Lys Asp Tyr Pro Lys Pro
            20                  25                  30

Asp Lys Ile Ser Asp Thr Asp Asn Tyr Arg Glu Gly Ala Ala Leu Ser
        35                  40                  45

Gln Lys Phe Lys Glu Leu Lys Gly Met Gly Lys Lys Lys Lys Val Ala
    50                  55                  60

Ile Val Gly Gly Gly Leu Ser Gly Leu Ala Cys Ala Lys Tyr Leu Val
65                  70                  75                  80

Asp Ala Gly His Glu Pro Ile Val Leu Glu Gly Arg Asp Val Leu Gly
                85                  90                  95

Gly Lys Val Ser Ala Trp Gln Asp Lys Asp Gly Asp Trp Ile Glu Thr
            100                 105                 110

Gly Leu His Ile Phe Phe Gly Ala Tyr Pro Asn Met Met Asn Leu Phe
        115                 120                 125

Ala Glu Leu Asp Ile Glu Asp Arg Leu Gln Trp Lys Val His Lys Met
    130                 135                 140

Ile Phe Ala Met Gln Glu Leu Pro Gly Glu Phe Thr Thr Phe Asp Phe
145                 150                 155                 160

Met Lys Gly Ile Pro Ala Pro Leu Asn Phe Gly Leu Ala Ile Leu Leu
                165                 170                 175
```

-continued

```
Asn Gln Lys Met Leu Ser Leu Pro Glu Lys Leu Gln Thr Ala Pro Pro
            180                 185                 190

Leu Ile Pro Met Leu Ile Glu Gly Gln Asp Phe Ile Asp Ala Gln Asp
        195                 200                 205

Glu Leu Ser Val Leu Asp Phe Met Arg Lys Tyr Gly Met Pro Glu Arg
    210                 215                 220

Ile Asn Glu Glu Val Phe Ile Ser Met Ala Lys Ala Leu Asp Phe Ile
225                 230                 235                 240

Asp Pro Asp Lys Leu Ser Met Thr Val Val Leu Thr Ala Met Asn Arg
                245                 250                 255

Phe Leu Asn Glu Thr Asp Gly Leu Gln Met Ala Phe Leu Asp Gly Asn
            260                 265                 270

Gln Pro Asp Arg Leu Cys Ala Pro Met Ala Asp His Val Lys Ala Gly
        275                 280                 285

Gly Gly Glu Val Arg Met Lys Ala Arg Leu Lys Glu Phe Val Leu Asn
    290                 295                 300

Asp Asp Gly Ser Val Lys Cys Leu Lys Met Thr Asn Gly Glu Glu Ile
305                 310                 315                 320

Val Ala Asp Glu Tyr Val Ser Ala Val Pro Val Asp Val Met Lys Arg
                325                 330                 335

Leu Leu Pro Lys Lys Trp Ser Asn Met Pro Phe Phe His Gln Ile Gln
            340                 345                 350

Asn Leu Glu Gly Ile Pro Val Ile Asn Ile His Leu Trp Phe Asp Arg
        355                 360                 365

Lys Leu Gln Asn Val Asp His Leu Cys Phe Ser Arg Ser Pro Leu Leu
    370                 375                 380

Ser Val Tyr Ala Asp Met Ser Thr Thr Cys Lys Glu Tyr Tyr Asp Glu
385                 390                 395                 400

Glu Lys Ser Met Leu Glu Leu Val Phe Ala Pro Cys Ser Pro Leu Ala
                405                 410                 415

Gly Gly Asn Thr Asn Trp Ile Ala Lys Ser Asn Gln Glu Ile Val Asp
            420                 425                 430

Ala Thr Met Lys Glu Leu Glu Arg Leu Phe Pro Leu Glu Ile Gly Pro
        435                 440                 445

Gly Ser Pro Asp Gly Val Gly Ala Lys Leu Leu Lys His Ala Val Val
    450                 455                 460

Lys Thr Pro Arg Ser Val Tyr Ala Ala Ile Pro Gly Arg Asn Lys Tyr
465                 470                 475                 480

Arg Pro Ser Gln Ala Thr Pro Ile Ser Asn Phe Thr Leu Ala Gly Asp
                485                 490                 495

Trp Thr Ser Gln Lys Phe Leu Gly Ser Met Glu Gly Ala Val Leu Gly
            500                 505                 510

Gly Lys Leu Ala Ala Glu Val Val Thr Asp Lys Ala Ile Tyr Gly Gly
        515                 520                 525

Pro Thr Lys Gly Ile Lys Lys Ile Val Pro Asp Val Val Lys Glu Ala
    530                 535                 540

Asn Ala Met Glu Ala Arg Glu Pro Glu Gly Ser Lys Gly Glu Ser Glu
545                 550                 555                 560

Leu Ser Tyr Gly Ala Gly Cys Val Met Gly Glu Glu Gln Glu Lys Glu
                565                 570                 575

Leu Ala Val Phe Asp Pro Glu Gln Met Val Thr Met Asp Asn Tyr Val
            580                 585                 590
```

```
Ala Arg Glu Ser Ile Pro Val Ser Arg
        595                 600


<210> SEQ ID NO 21
<211> LENGTH: 562
<212> TYPE: PRT
<213> ORGANISM: Micromonas pusilla

<400> SEQUENCE: 21

Met Ala Pro His Ala Leu Ser Ser Ala Ser Trp Thr Thr Pro Thr Arg
1               5                   10                  15

Leu Pro Ser Arg Arg Cys Arg Arg Ala Ser Ala Ala Arg Gly Arg Phe
            20                  25                  30

Ala Ala Ser Pro Ser Pro Leu Val Val Ala Pro Arg Ala Gly Asp Tyr
        35                  40                  45

Pro Ala Pro Asp Leu Asp Val Pro Ser Asn Arg Asn Tyr Gln Asp Ala
    50                  55                  60

Lys Ala Leu Ser Ala Lys Leu Thr Arg Asn Val Ala Asp Val Gly Ala
65                  70                  75                  80

Ser His Ala Pro Lys Arg Val Val Val Val Gly Gly Gly Leu Ala Gly
                85                  90                  95

Leu Ser Cys Ala Lys Tyr Leu Ala Asp Ala Gly His Val Pro Ile Val
            100                 105                 110

Ile Glu Arg Gly Asp Val Leu Gly Gly Lys Val Ser Ala Trp Arg Asp
        115                 120                 125

Asp Asp Gly Asp Trp Ile Glu Thr Gly Leu His Ile Phe Phe Gly Ala
    130                 135                 140

Tyr Pro Asn Met Met Asn Leu Phe Asp Glu Leu Gly Ile Gly Asp Arg
145                 150                 155                 160

Leu Gln Trp Lys Glu His Ala Met Thr Phe Ala Met Arg Asp Phe Pro
                165                 170                 175

Gly Glu Phe Thr Lys Phe Asn Phe Pro Lys Gly Val Pro Ala Pro Phe
            180                 185                 190

Asn Met Ala Tyr Ala Ile Leu Ser Asn Asp Arg Met Leu Ser Pro Ala
        195                 200                 205

Glu Lys Leu Arg Thr Gly Ala Pro Leu Val Pro Met Leu Leu Gly Gly
    210                 215                 220

Gln Asp Tyr Ile Asp Ala Gln Asp Glu Leu Ser Val Gln Glu Trp Met
225                 230                 235                 240

Arg Arg Asn Phe Met Pro Glu Arg Val Arg Glu Glu Leu Phe Ile Ala
                245                 250                 255

Met Gly Lys Ala Leu Asp Phe Ile Asp Ser Asp Lys Leu Ser Met Thr
            260                 265                 270

Val Ile Leu Thr Ala Met Asn Arg Phe Ile Asn Glu Thr His Gly Ser
        275                 280                 285

Lys Thr Ala Phe Leu Asp Gly Asn Gln Pro Asp Arg Leu Cys Ala Pro
    290                 295                 300

Met Ala Glu His Phe Val Ser Arg Gly Gly Ser Val Arg Leu Gly Ala
305                 310                 315                 320

Gly Met Lys Lys Phe Leu Thr Thr Asp Asp Ser Val Ser Val Thr Gly
                325                 330                 335

Ile Glu Leu Val Ser Gly Glu Val Val Thr Gly Asp His Tyr Val Ser
            340                 345                 350

Ala Met Pro Val Asp Ala Leu Lys Leu Leu Leu Pro Glu Pro Trp Lys
        355                 360                 365
```

```
Arg Ala Pro Phe Phe Ala Gln Leu Lys Glu Leu Glu Gly Ile Pro Val
    370                 375                 380

Ile Asn Val His Leu Trp Phe Asp Arg Lys Leu Arg Pro Tyr Asp Gly
385                 390                 395                 400

Leu Val Phe Ser Arg Ser Lys Leu Leu Ser Val Tyr Ala Asp Met Ser
                405                 410                 415

Glu Cys Cys Ala Glu Tyr Ala Asp Ala Glu Arg Ser Met Leu Glu Leu
            420                 425                 430

Val Phe Ala Pro Cys Asp Glu Arg Ala Gly Ser Asp Val Asn Trp Ile
        435                 440                 445

Ala Lys Ser Asp Gln Asp Ile Val Asp Ala Thr Val Ala Glu Leu Arg
    450                 455                 460

Arg Leu Phe Pro Asn Glu Ile Lys Ala Asp Gly Thr Gly Ala Lys Val
465                 470                 475                 480

Val Lys His Ala Val Val Lys Thr Pro Arg Ser Val Tyr Ala Ala Ile
                485                 490                 495

Pro Gly Arg Asn Lys Phe Arg Pro Ser Gln Arg Thr Pro Ile Glu Asn
            500                 505                 510

Phe Thr Leu Ala Gly Asp Phe Thr Ser Gln Lys Phe Leu Gly Ser Met
        515                 520                 525

Glu Gly Ala Val Leu Ser Gly Lys Leu Ala Ala Glu Val Ile Ala Asp
    530                 535                 540

Gln Tyr Ala Gly Arg Val Gly Lys Pro Ile Lys Glu Val Asp Ala Arg
545                 550                 555                 560

Tyr Arg


<210> SEQ ID NO 22
<211> LENGTH: 602
<212> TYPE: PRT
<213> ORGANISM: Artificial Sequence
<220> FEATURE:
<223> OTHER INFORMATION: Synthetic peptide sequence

<400> SEQUENCE: 22

Met Asp Ala Arg Ala Leu Arg Ala Gln Lys Thr Gln Arg Gly Ser Thr
1               5                   10                  15

Ser Ser Ser Arg Arg Ala Val Arg Val Val Ala Lys Asp Tyr Pro Lys
            20                  25                  30

Pro Asp Asn Ile Asp Lys Thr Glu Asn Tyr Arg Ile Ala Gly Asp Leu
        35                  40                  45

Ser Lys Arg Phe Ala Ser Asp Leu Arg Val Arg Asp Gly Glu Lys Lys
    50                  55                  60

Lys Val Ala Ile Val Gly Gly Gly Leu Ser Gly Leu Ala Cys Ala Lys
65                  70                  75                  80

Tyr Leu Ala Glu Ala Gly His Glu Pro Ile Val Leu Glu Ala Arg Asp
                85                  90                  95

Val Leu Gly Gly Lys Val Ser Ala Trp Lys Asp Lys Asp Gly Asp Trp
            100                 105                 110

Ile Glu Thr Gly Leu His Ile Phe Phe Gly Ala Tyr Pro Asn Met Met
        115                 120                 125

Asn Leu Phe Ala Glu Leu Asp Ile Glu Asp Arg Leu Gln Trp Lys Val
    130                 135                 140

His Lys Met Ile Phe Ala Met Gln Glu Leu Pro Gly Glu Phe Thr Ser
145                 150                 155                 160
```

-continued

```
Phe Asp Phe Ile Lys Gly Ile Pro Ala Pro Leu Asn Phe Gly Leu Ala
                165                 170                 175

Ile Leu Leu Asn Gln Lys Met Leu Thr Leu Pro Glu Lys Leu Gln Thr
            180                 185                 190

Ala Pro Pro Leu Leu Pro Met Leu Ile Glu Gly Gln Asp Phe Ile Asp
        195                 200                 205

Lys Gln Asp Glu Leu Ser Val Gln Gln Phe Met Arg Lys Tyr Gly Met
    210                 215                 220

Pro Glu Arg Ile Asn Glu Glu Val Phe Ile Ser Met Ala Lys Ala Leu
225                 230                 235                 240

Asp Phe Ile Asp Pro Asp Lys Leu Ser Met Thr Val Val Leu Thr Ala
                245                 250                 255

Met Asn Arg Phe Leu Asn Glu Thr Asp Gly Leu Gln Met Ala Phe Leu
            260                 265                 270

Asp Gly Asn Gln Pro Asp Arg Leu Cys Ala Pro Met Val Glu Ser Ile
        275                 280                 285

Thr Lys Asn Gly Gly Ser Val Met Thr Lys Gln Arg Leu Lys Glu Phe
    290                 295                 300

Val Leu Asn Glu Asp Gly Ser Val Lys His Leu Ala Met Ala Asn Gly
305                 310                 315                 320

Asp Ile Val Glu Ala Asp Glu Tyr Ile Ser Ala Met Pro Val Asp Val
                325                 330                 335

Met Lys Arg Met Met Pro Lys Lys Trp Gly Glu Ile Pro His Phe Ala
            340                 345                 350

Gln Leu Lys Glu Leu Glu Gly Ile Pro Val Ile Asn Ile His Leu Trp
        355                 360                 365

Phe Asp Arg Lys Leu Lys Asn Val Asp His Leu Cys Phe Ser Arg Ser
    370                 375                 380

Pro Leu Leu Ser Val Tyr Ala Asp Met Ser Thr Thr Cys Lys Glu Tyr
385                 390                 395                 400

Tyr Asp Glu Glu Lys Ser Met Leu Glu Leu Val Phe Ala Pro Cys Ser
                405                 410                 415

Pro Ile Ala Gly Gly Lys Thr Asn Trp Ile Ala Lys Ser Asn Gln Glu
            420                 425                 430

Ile Val Asp Ala Thr Met Leu Glu Leu Glu Arg Leu Phe Pro Leu Glu
        435                 440                 445

Ile Gly Pro Lys Ser Pro Asp Gly Val Gly Ala Arg Leu Leu Lys His
    450                 455                 460

Ala Val Val Lys Thr Pro Arg Ser Val Tyr Ala Ala Ile Pro Gly Arg
465                 470                 475                 480

Asn Lys Phe Arg Pro Ser Gln Glu Thr Pro Ile Lys Asn Phe Thr Leu
                485                 490                 495

Ala Gly Asp Tyr Thr Ser Gln Lys Phe Leu Gly Ser Met Glu Gly Ala
            500                 505                 510

Val Leu Ala Gly Lys Leu Ala Ala Glu Val Val Ala Ser Arg Ala Lys
        515                 520                 525

Gly Lys Ala Thr Gln Gly Leu Lys Pro Val Gln Gln Ser Ile Ile Asn
    530                 535                 540

Ala Ile Gly Pro Val Ser Glu Pro Val Gly Val Ile Gly Asp Thr Glu
545                 550                 555                 560

Phe Ala Phe Gly Gly Gly Lys Val Met Glu Val Ala Asp Glu Ala Glu
                565                 570                 575

Leu Glu Lys Phe Asp Ala Glu Gln Leu Val Lys Leu Asp Gly Trp Thr
```

```
            580                 585                 590

Gly Ser Lys Glu Lys Ala Ala Arg Ala Arg
        595                 600


<210> SEQ ID NO 23
<211> LENGTH: 540
<212> TYPE: PRT
<213> ORGANISM: Artificial Sequence
<220> FEATURE:
<223> OTHER INFORMATION: Synthetic peptide sequence

<400> SEQUENCE: 23

Met Arg Ser Ala Leu Ile Thr Ala Pro Ile Val Asp Ala Arg Arg Ala
1               5                   10                  15

Arg Val His Arg His Ala Ser Ile Thr Arg Ala Arg Asp Tyr Pro Lys
            20                  25                  30

Pro Asp Leu Asp Val Pro Ser Asn Gly Asn Tyr Gln Glu Ser Lys Ala
        35                  40                  45

Leu Ser Gln Lys Leu Lys Ser Ile Ala Leu Ala Glu Arg Lys Ser Val
    50                  55                  60

Leu Ile Ile Gly Gly Gly Leu Ala Gly Leu Ser Cys Gly Lys Tyr Leu
65                  70                  75                  80

Ser Asp Ala Gly Ala Arg Pro Ile Val Val Glu Arg Asn Lys Met Leu
                85                  90                  95

Gly Gly Lys Val Ser Ala Trp Arg Asp Ala Glu Gly Asp Trp Ile Glu
            100                 105                 110

Thr Gly Leu His Ile Phe Phe Gly Ala Tyr Pro Asn Met Met Asn Leu
        115                 120                 125

Phe Ala Glu Leu Gly Ile Glu Asp Arg Leu Gln Trp Lys Glu His Ser
    130                 135                 140

Met Thr Phe Ala Met Lys Asp Tyr Pro Gly Glu Phe Thr Lys Phe Lys
145                 150                 155                 160

Phe Pro Glu Asn Val Pro Ala Pro Phe Asn Met Ala Tyr Ala Ile Leu
                165                 170                 175

Ser Asn Asp Lys Met Leu Thr Trp Thr Glu Lys Leu Arg Thr Gly Ala
            180                 185                 190

Pro Leu Val Pro Met Leu Ala Gly Gly Gln Gly Tyr Ile Asp Ala Gln
        195                 200                 205

Asp Glu Leu Ser Val Glu Glu Trp Met Lys Lys Asn Phe Met Pro Lys
    210                 215                 220

Arg Val Ser Asp Glu Leu Phe Ile Ala Met Gly Lys Ala Leu Asp Phe
225                 230                 235                 240

Ile Asp Val Asp Lys Leu Ser Met Thr Val Ile Leu Thr Ala Met Asn
                245                 250                 255

Arg Phe Ile Asn Glu Thr His Gly Ser Lys Thr Ala Phe Leu Asp Gly
            260                 265                 270

Asn Gln Pro Asp Arg Leu Cys Ala Pro Met Lys Glu His Ile Glu Arg
        275                 280                 285

Val Gly Gly Gly Glu Val Met Val Asp Thr Pro Met Gln Glu Ile Leu
    290                 295                 300

Thr Asp Val Glu Gly Asn Val Glu Gly Val Lys Leu Arg Asn Gly Glu
305                 310                 315                 320

Ile Leu Thr Ala Asp His Tyr Val Ser Ala Met Pro Val Asp Ala Leu
                325                 330                 335

Lys Leu Lys Leu Pro Asp Ala Trp Lys Pro Met Pro Phe Phe Lys Gln
```

```
            340                 345                 350

Leu Asp Glu Leu Glu Gly Ile Pro Val Ile Asn Val His Leu Trp Phe
        355                 360                 365

Asp Arg Lys Leu Arg Pro Tyr Asp Gly Leu Val Phe Ser Arg Ser Pro
    370                 375                 380

Leu Leu Ser Val Tyr Ala Asp Met Ser Glu Cys Cys Lys Glu Tyr Thr
385                 390                 395                 400

Asp Ser Glu Arg Ser Met Leu Glu Leu Val Phe Ala Pro Cys Asp Lys
                405                 410                 415

Arg Ala Gly Ser Asp Ile Asn Trp Ile Gly Ala Ser Asp Glu Glu Ile
            420                 425                 430

Val Ala Ala Thr Leu Lys Glu Leu Glu Lys Leu Phe Pro Asp Glu Leu
        435                 440                 445

Gly Ser Asn Gly Gly Ala Lys Leu Arg Lys Ser Ala Val Val Lys Thr
    450                 455                 460

Pro Arg Ser Val Tyr Ala Ala Ile Pro Gly Arg Asn Lys Phe Arg Pro
465                 470                 475                 480

Ser Gln Gln Thr Pro Ile Lys Asn Phe Thr Leu Ala Gly Asp Phe Thr
                485                 490                 495

Ser Gln Lys Phe Leu Gly Ser Met Glu Gly Ala Val Leu Ser Gly Lys
            500                 505                 510

Leu Ala Ala Glu Val Val Ala Glu Thr Leu Ala Gly Cys Glu Pro Thr
        515                 520                 525

Arg Gly Ile Lys Pro Val His Glu Ser Val Arg Val
    530                 535                 540


<210> SEQ ID NO 24
<211> LENGTH: 599
<212> TYPE: PRT
<213> ORGANISM: Artificial Sequence
<220> FEATURE:
<223> OTHER INFORMATION: Synthetic peptide sequence

<400> SEQUENCE: 24

Met Thr Ser Arg Ala Gly Thr Lys Ala Lys Thr Arg Ala Thr Arg Arg
1               5                   10                  15

Ser Gly Met Arg Val Glu Ala Lys Asp Tyr Pro Lys Pro Asp Asn Ile
            20                  25                  30

Asp Lys Thr Asp Asn Tyr Arg Ile Ala Ser Glu Leu Ser Lys Arg Phe
        35                  40                  45

Ala Thr Asp Leu Lys Ala Asn Gly Thr Glu Lys Lys Arg Val Ala Ile
    50                  55                  60

Val Gly Gly Gly Leu Ser Gly Leu Ala Cys Ala Lys Tyr Leu Ala Glu
65                  70                  75                  80

Ala Gly His Glu Pro Ile Val Leu Glu Ala Arg Asp Val Leu Gly Gly
                85                  90                  95

Lys Val Ser Ala Trp Gln Asp Lys Asp Gly Asp Trp Ile Glu Thr Gly
            100                 105                 110

Leu His Ile Phe Phe Gly Ala Tyr Pro Asn Met Met Asn Leu Phe Asn
        115                 120                 125

Glu Leu Lys Ile Glu Asp Arg Leu Gln Trp Lys Val His Lys Met Ile
    130                 135                 140

Phe Ala Met Gln Glu Leu Pro Gly Glu Phe Thr Ser Phe Asp Phe Ile
145                 150                 155                 160

Lys Gly Ile Pro Ala Pro Phe Asn Phe Gly Leu Ala Ile Leu Met Asn
```

```
                165                 170                 175

Gln Lys Met Leu Ser Leu Pro Glu Lys Leu Gln Thr Ala Pro Pro Leu
            180                 185                 190

Leu Pro Met Leu Ile Glu Gly Gln Asp Phe Ile Asp Lys Gln Asp Glu
        195                 200                 205

Leu Ser Val Gln Asp Phe Met Arg Lys Tyr Gly Met Pro Glu Arg Ile
    210                 215                 220

Asn Glu Glu Val Phe Ile Ser Met Ala Lys Ala Leu Asp Phe Ile Asp
225                 230                 235                 240

Pro Asp Lys Leu Ser Met Thr Val Val Leu Thr Ala Met Asn Arg Phe
                245                 250                 255

Leu Asn Glu Thr Asp Gly Leu Gln Met Ala Phe Leu Asp Gly Asn Gln
            260                 265                 270

Pro Asp Arg Leu Cys Ala Pro Met Val Asp Ser Ile Glu Lys Asn Gly
        275                 280                 285

Gly Ser Val Lys Thr Lys Gln Arg Leu Lys Glu Phe Val Leu Asn Glu
    290                 295                 300

Asp Gly Ser Val Lys His Leu Ala Met Ala Asn Gly Asp Ile Ile Glu
305                 310                 315                 320

Ala Asp Glu Tyr Ile Ser Ala Met Pro Val Asp Val Ile Lys Arg Met
                325                 330                 335

Met Pro Lys Pro Trp Ala Glu Met Pro His Phe Ala Gln Leu Lys Glu
            340                 345                 350

Leu Glu Gly Ile Pro Val Ile Asn Ile His Leu Trp Phe Asp Arg Lys
        355                 360                 365

Leu Lys Asn Val Asp His Leu Cys Phe Ser Arg Ser Pro Leu Leu Ser
    370                 375                 380

Val Tyr Ala Asp Met Ser Thr Thr Cys Lys Glu Tyr Tyr Asp Glu Glu
385                 390                 395                 400

Lys Ser Met Leu Glu Leu Val Phe Ala Pro Cys Ser Pro Ile Ala Gly
                405                 410                 415

Gly Lys Thr Asn Trp Ile Ala Lys Ser Asn Gln Glu Ile Val Asp Ala
            420                 425                 430

Thr Met Leu Glu Leu Glu Arg Leu Phe Pro Leu Glu Ile Gly Pro Lys
        435                 440                 445

Ser Pro Asp Gly Val Gly Ala Lys Leu Leu Lys His Ala Val Val Lys
    450                 455                 460

Thr Pro Arg Ser Val Tyr Ala Ala Ile Pro Gly Arg Asn Lys Phe Arg
465                 470                 475                 480

Pro Ser Gln Glu Thr Pro Ile Lys Asn Phe Thr Leu Ala Gly Asp Tyr
                485                 490                 495

Thr Ser Gln Lys Phe Leu Gly Ser Met Glu Gly Ala Val Leu Gly Gly
            500                 505                 510

Lys Leu Ala Ala Glu Val Val Ala Ser Arg Ala Lys Gly Met Lys Thr
        515                 520                 525

Gln Gly Leu Lys Ala Val Gln Lys Ser Ile Ile Asp Ser Ile Gly Pro
    530                 535                 540

Ala Lys Glu Pro Leu Gly Val Val Gly Glu Ser Glu Phe Ala Phe Gly
545                 550                 555                 560

Gly Gly Lys Val Met Glu Asp Ala Asp Glu Ala Glu Leu Ala Asn Phe
                565                 570                 575

Asp Ala Glu Gln Leu Thr Lys Leu Asp Gly Trp Thr Gly Ser Lys Glu
            580                 585                 590
```

Ala Ala Ser Val Arg Ala Arg
595

<210> SEQ ID NO 25
<211> LENGTH: 552
<212> TYPE: PRT
<213> ORGANISM: Artificial Sequence
<220> FEATURE:
<223> OTHER INFORMATION: Synthetic peptide sequence

<400> SEQUENCE: 25

Met Arg Ala Ala Leu Ala Pro Arg Pro Ile Pro Leu Ser Arg Ala Ser
1 5 10 15

Gly Ala Arg Ala Arg Thr Ala Thr Pro Arg Thr Arg Cys Ala Asp Tyr
20 25 30

Pro Lys Pro Asp Leu Asp Val Lys Ser Asn Ala Asn Phe Gln Glu Ala
35 40 45

Lys Ala Lys Ser Ala Arg Leu Ala Thr Phe Arg Ala Arg Val Arg Arg
50 55 60

Asp Asp Ala Pro Glu Lys Pro Thr Val Leu Val Ile Gly Gly Gly Leu
65 70 75 80

Ala Gly Leu Ser Cys Gly Lys Tyr Leu Ala Asp Ala Gly Cys Ala Pro
85 90 95

Thr Val Ile Glu Arg Gly Lys Ala Leu Gly Gly Lys Val Ser Ala Trp
100 105 110

Arg Asp Asp Asp Gly Asp Trp Ile Glu Thr Gly Leu His Ile Phe Phe
115 120 125

Gly Ala Tyr Pro Asn Val Met Asn Leu Phe Arg Glu Leu Asp Ile Glu
130 135 140

Asp Arg Leu Gln Trp Lys Glu His Ala Met Thr Phe Ala Met Lys Asp
145 150 155 160

Tyr Pro Gly Glu Phe Thr Lys Phe Tyr Phe Pro Pro Ala Leu Pro Ala
165 170 175

Pro Leu Asn Met Gly Tyr Ala Ile Leu Ser Asn Asp Lys Met Leu Thr
180 185 190

Trp Ser Glu Lys Leu Arg Thr Gly Ala Pro Leu Val Pro Met Leu Val
195 200 205

Gly Gly Gln Asp Tyr Ile Asp Ala Gln Asp Glu Leu Ser Cys Glu Glu
210 215 220

Trp Met Lys Lys Asn Phe Met Pro Lys Arg Val Arg Asp Glu Leu Phe
225 230 235 240

Ile Ala Met Gly Lys Ala Leu Asp Phe Ile Asp Ala Asp Lys Leu Ser
245 250 255

Met Thr Val Ile Leu Thr Ala Met Asn Arg Phe Ile Asn Glu Thr His
260 265 270

Gly Ser Lys Thr Ala Phe Leu Asp Gly Asn Gln Pro Asp Arg Leu Cys
275 280 285

Ala Pro Met Ala Glu His Ile Glu Arg Val Gly Gly Gly Lys Val Ile
290 295 300

Thr Asp Ala Pro Met Gln Glu Ile Leu Val Asp Ala Asp Gly Asn Val
305 310 315 320

Glu Gly Val Lys Met Arg Asp Gly Gln Ile Met Thr Ala Asp His Tyr
325 330 335

Val Ser Ala Met Pro Val Asp Ala Leu Lys Leu Lys Leu Pro Asp Val
340 345 350

```
Trp Lys Ala Met Pro Phe Phe Arg Gln Leu Asn Glu Leu Glu Gly Ile
        355                 360                 365

Pro Val Ile Asn Val His Leu Trp Phe Asp Arg Lys Leu Arg Pro Tyr
    370                 375                 380

Asp Gly Leu Val Phe Ser Arg Ser Pro Leu Leu Ser Val Tyr Ala Asp
385                 390                 395                 400

Met Ser Glu Cys Cys Ala Glu Tyr Lys Asp Asp Asp Arg Ser Met Leu
                405                 410                 415

Glu Leu Val Phe Ala Pro Cys Asp Lys Arg Ala Gly Ser Asp Val Asn
            420                 425                 430

Trp Ile Gly Ala Ser Asp Glu Asp Ile Val Ala Ala Thr Met Lys Glu
        435                 440                 445

Leu Glu Thr Leu Phe Pro Asp Glu Leu Gly Ala Gly Lys Asp Gly Ala
    450                 455                 460

Ser Gly Ala Lys Leu Arg Lys Phe Ala Val Val Lys Thr Pro Arg Ser
465                 470                 475                 480

Val Tyr Ala Ala Ile Pro Gly Arg Asn Lys Phe Arg Pro Ser Gln His
                485                 490                 495

Thr Pro Ile Lys Asn Phe Thr Leu Ala Gly Asp Tyr Thr Ser Gln Lys
            500                 505                 510

Phe Leu Gly Ser Met Glu Gly Ala Val Leu Ser Gly Lys Leu Ala Ala
        515                 520                 525

Glu Val Val Ala Glu Thr Phe Ala Gly Val Glu Pro Thr Thr Arg Val
    530                 535                 540

Lys Pro Val His Glu Ser Val Ala
545                 550
```

<210> SEQ ID NO 26
<211> LENGTH: 619
<212> TYPE: PRT
<213> ORGANISM: Artificial Sequence
<220> FEATURE:
<223> OTHER INFORMATION: Synthetic peptide sequence

<400> SEQUENCE: 26

```
Met Ser Ser Ser Ala Leu Ser Ala Arg Arg Gly Ala Leu Ser Gln Gly
1               5                   10                  15

Ser Pro Thr Thr Arg Gly Ala Arg Asn Gln Arg Arg Gln His Arg Ala
            20                  25                  30

Gly Gly Arg Ala Arg Val Val Arg Val Glu Ala Lys Asp Tyr Pro Lys
        35                  40                  45

Pro Asp Ala Ile Ser Gln Thr Glu Asn Tyr Arg Val Ala Gly Ala Leu
    50                  55                  60

Ser Ser Arg Phe Thr Ser Asp Leu Lys Val Ser Gly Glu Gly Gln Lys
65                  70                  75                  80

Lys Lys Val Ala Ile Val Gly Gly Gly Leu Ser Gly Leu Ala Cys Ala
                85                  90                  95

Lys Tyr Leu Ala Glu Ala Gly His Glu Pro Ile Val Leu Glu Ala Arg
            100                 105                 110

Asp Val Leu Gly Gly Lys Val Ser Ala Trp Gln Asp Lys Asp Gly Asp
        115                 120                 125

Trp Ile Glu Thr Gly Leu His Ile Phe Phe Gly Ala Tyr Pro Asn Met
    130                 135                 140

Met Asn Leu Phe Ser Glu Leu Asp Ile Glu Asp Arg Leu Gln Trp Lys
145                 150                 155                 160
```

Val His Lys Met Ile Phe Ala Met Gln Glu Leu Pro Gly Glu Phe Thr
165 170 175

Thr Phe Asp Phe Ile Lys Gly Ile Pro Ala Pro Phe Asn Phe Gly Leu
180 185 190

Ala Ile Leu Leu Asn Gln Lys Met Leu Thr Leu Pro Glu Lys Leu Gln
195 200 205

Thr Ala Pro Ala Leu Leu Pro Met Leu Ile Lys Gly Gln Glu Phe Ile
210 215 220

Asp Glu Gln Asp Glu Leu Ser Val Leu Asp Phe Met Arg Lys Tyr Gly
225 230 235 240

Met Pro Glu Arg Ile Asn Lys Glu Val Phe Ile Ser Met Ala Lys Ala
245 250 255

Leu Asp Phe Ile Asp Pro Asp Lys Leu Ser Met Thr Val Val Leu Thr
260 265 270

Ala Met Asn Arg Phe Leu Asn Glu Thr Asp Gly Leu Gln Met Ala Phe
275 280 285

Leu Asp Gly Asn Gln Pro Asp Arg Leu Cys Ala Pro Met Val Asp Ser
290 295 300

Ile Thr Lys Asn Gly Gly Ser Val His Met Lys Gln Arg Leu Lys Glu
305 310 315 320

Phe Val Leu Asn Glu Asp Gly Ser Val Lys His Leu Ala Met Ala Asn
325 330 335

Gly Asp Ile Ile Glu Ala Asp Glu Tyr Ile Ser Ala Met Pro Val Asp
340 345 350

Val Met Lys Arg Met Met Pro Lys Gln Trp Gly Glu Met Pro His Phe
355 360 365

Ala Gln Leu Lys Glu Leu Glu Gly Ile Pro Val Ile Asn Ile His Leu
370 375 380

Trp Phe Asp Arg Lys Leu Thr Asn Val Asp His Leu Cys Phe Ser Arg
385 390 395 400

Ser Pro Leu Leu Ser Val Tyr Ala Asp Met Ser Thr Thr Cys Lys Glu
405 410 415

Tyr Tyr Asp Glu Glu Lys Ser Met Leu Glu Leu Val Phe Ala Pro Cys
420 425 430

Ser Pro Ile Ala Gly Gly Lys Thr Asn Trp Ile Ala Lys Ser Asn Gln
435 440 445

Glu Ile Val Asp Ala Thr Met Lys Glu Leu Glu Arg Leu Phe Pro Leu
450 455 460

Asp Ile Gly Pro Asn Ser Pro Asp Gly Val Gly Ala Lys Leu Leu Lys
465 470 475 480

His Ala Val Val Lys Thr Pro Arg Ser Val Tyr Ala Ala Ile Pro Gly
485 490 495

Arg Asn Lys Phe Arg Pro Ser Gln Glu Thr Pro Ile Ser Asn Phe Thr
500 505 510

Leu Ala Gly Asp Tyr Thr Ser Gln Lys Phe Leu Gly Ser Met Glu Gly
515 520 525

Ala Val Leu Gly Gly Lys Leu Ala Ala Glu Val Val Ala Ser Arg Ala
530 535 540

Lys Gly Met Ala Thr Gln Gly Leu Lys Pro Val Gln Gln Ser Ile Ile
545 550 555 560

Asn Gly Leu Ser Ala Gly Ala Asp Glu Ala Met Gly Pro Val Gly Glu
565 570 575

```
Thr Glu Leu Ala Phe Gly Gly Gly Lys Val Met Asp Glu Ser Asp Glu
            580                 585                 590

Ala Asp Leu Ala Arg Phe Asp Ala Glu Gln Leu Val Lys Leu Asp Gly
        595                 600                 605

Trp Thr Gly Ser Lys Glu Ala Ala Arg Ala Arg
    610                 615


<210> SEQ ID NO 27
<211> LENGTH: 525
<212> TYPE: PRT
<213> ORGANISM: Artificial Sequence
<220> FEATURE:
<223> OTHER INFORMATION: Synthetic peptide sequence

<400> SEQUENCE: 27

Met Thr Ser Ser Ala Leu Arg Leu Gly Asp Phe Pro Lys Pro Ala Leu
1               5                   10                  15

Asp Val Pro Thr Asn Glu Asn Tyr Ala Glu Ala Lys Ala Leu Ser Gln
            20                  25                  30

Lys Leu Arg Asn Phe Gln Ile Asp Arg Ser Ser Thr Glu Lys Pro Thr
        35                  40                  45

Val Leu Val Ile Gly Gly Gly Leu Ala Gly Leu Ser Cys Gly Lys Tyr
    50                  55                  60

Cys Ser Asp Ala Gly Ala Glu Val Thr Leu Ile Glu Arg Ala Lys Met
65                  70                  75                  80

Leu Gly Gly Lys Thr Ser Ala Trp Gln Asp Lys Asp Gly Asp Trp Ile
                85                  90                  95

Glu Thr Gly Leu His Ile Phe Phe Gly Ala Tyr Pro Asn Met Met Asn
            100                 105                 110

Leu Phe Ala Glu Leu Glu Ile Glu Asp Arg Leu Gln Trp Lys Glu His
        115                 120                 125

Ser Met Thr Phe Ala Met Arg Asp Phe Pro Gly Glu Phe Thr Lys Phe
    130                 135                 140

Phe Phe Pro Pro Ala Leu Pro Ala Pro Phe Asn Met Gly Trp Ala Ile
145                 150                 155                 160

Leu Ser Asn Asp Lys Met Leu Ser Trp Thr Glu Lys Ile Arg Thr Gly
                165                 170                 175

Ile Pro Leu Leu Pro Met Leu Leu Gly Gly Gln Glu Tyr Ile Asp Ala
            180                 185                 190

Gln Asp Glu Leu Ser Val Glu Glu Trp Met Lys Lys Asn Phe Met Pro
        195                 200                 205

Lys Arg Val Arg Asp Glu Leu Phe Ile Ala Met Gly Lys Ala Leu Asp
    210                 215                 220

Phe Ile Asp Ala Asp Lys Leu Ser Met Thr Val Ile Leu Thr Ala Met
225                 230                 235                 240

Asn Arg Phe Ile Asn Glu Thr His Gly Ser Lys Thr Ala Phe Leu Asp
                245                 250                 255

Gly Asn Gln Pro Asp Arg Leu Cys Ala Pro Met Ala Glu His Ile Glu
            260                 265                 270

Arg Val Gly Gly Gly Lys Val Leu Val Asp Thr Pro Met Gln Glu Ile
        275                 280                 285

Leu Val Asp Glu Asn Gly Arg Val Glu Gly Val Lys Leu Arg Asn Gly
    290                 295                 300

Glu Ile Val Thr Ala Asp His Tyr Val Ser Ala Met Pro Val Asp Ala
305                 310                 315                 320
```

-continued

Leu Lys Leu Lys Leu Pro Glu Lys Trp Arg Ala Met Pro Phe Phe Lys
325 330 335

Gln Leu Asp Glu Leu Glu Gly Ile Pro Val Ile Asn Val His Leu Trp
340 345 350

Phe Asp Arg Lys Leu Arg Pro Tyr Asn Gly Leu Val Phe Ser Arg Ser
355 360 365

Pro Leu Leu Ser Val Tyr Ala Asp Met Ser Glu Cys Cys Ala Glu Tyr
370 375 380

Ala Asp Glu Asn Arg Ser Met Leu Glu Leu Val Phe Ala Pro Cys Asp
385 390 395 400

Met Thr Ala Gly Ser Asp Val Asn Trp Ile Ala Ala Ser Asp Asp Glu
405 410 415

Ile Val Ser Ala Thr Leu Lys Glu Leu Glu Asn Leu Phe Pro Asp Glu
420 425 430

Ile Gly Gly Glu Glu Gly Ala Lys Leu Arg Lys Ala Ala Val Val Lys
435 440 445

Thr Pro Arg Ser Val Tyr Ala Ala Thr Pro Gly Arg Asn Lys Phe Arg
450 455 460

Pro Ser Gln Asn Thr Pro Ile Glu Asn Phe Thr Leu Ala Gly Asp Phe
465 470 475 480

Thr Ser Gln Lys Phe Leu Gly Ser Met Glu Gly Ala Ile Leu Ser Gly
485 490 495

Lys Leu Ala Ala Glu Val Thr Ala Glu Lys Leu Ser Gly Arg Gln Pro
500 505 510

Ser Arg Gly Val Lys Pro Val His His Ser Met Lys Met
515 520 525

<210> SEQ ID NO 28
<211> LENGTH: 621
<212> TYPE: PRT
<213> ORGANISM: Thalassiosira pseudonana

<400> SEQUENCE: 28

Met Ile Ile Thr Asn Phe Ile Leu Ser Thr Val Leu Ala Thr Ser Met
1 5 10 15

Ala Phe Gln Pro His Thr Pro Ile Leu Ser Lys Pro Ser Phe Ser Asn
20 25 30

Arg Val His Arg Ser Pro Lys Ile Gly Ser Ser Asn Leu Val Met Lys
35 40 45

Asp Phe Pro Lys Pro Asn Val Glu Asp Thr Asp Asn Tyr Arg Tyr Ala
50 55 60

Glu Ala Met Ser Thr Ser Phe Lys Thr Ser Leu Arg Val Thr Asn Asp
65 70 75 80

Ser Gln Lys Lys Lys Val Ala Ile Ile Gly Gly Gly Leu Ser Gly Leu
85 90 95

Ser Cys Ala Lys Tyr Leu Ser Asp Ala Gly His Glu Pro Thr Val Tyr
100 105 110

Glu Ala Arg Asp Val Leu Gly Gly Lys Val Ser Ala Trp Gln Asp Glu
115 120 125

Asp Gly Asp Trp Ile Glu Thr Gly Leu His Ile Phe Phe Gly Ala Tyr
130 135 140

Pro Asn Val Met Asn Met Phe Ala Glu Leu Gly Ile His Asp Arg Leu
145 150 155 160

Gln Trp Lys Ile His Gln Met Ile Phe Ala Met Gln Glu Leu Pro Gly
165 170 175

-continued

```
Glu Phe Thr Thr Phe Asp Phe Ile Pro Gly Ile Pro Ala Pro Phe Asn
            180                 185                 190

Phe Gly Leu Ala Ile Leu Met Asn Gln Lys Met Leu Thr Leu Gly Glu
        195                 200                 205

Lys Ile Gln Thr Ala Pro Pro Leu Leu Pro Met Leu Ile Glu Gly Gln
    210                 215                 220

Ser Phe Ile Asp Ala Gln Asp Glu Leu Ser Val Thr Gln Phe Met Arg
225                 230                 235                 240

Lys Tyr Gly Met Pro Glu Arg Ile Asn Glu Glu Val Phe Ile Ala Met
                245                 250                 255

Ala Lys Ala Leu Asp Phe Ile Asp Pro Asp Lys Leu Ser Met Thr Val
            260                 265                 270

Val Leu Thr Ala Met Asn Arg Phe Leu Asn Glu Ser Asn Gly Leu Gln
        275                 280                 285

Met Ala Phe Leu Asp Gly Asn Gln Pro Asp Arg Trp Cys Thr Pro Thr
    290                 295                 300

Lys Glu Tyr Val Glu Ala Arg Gly Gly Lys Val Lys Leu Asn Ser Pro
305                 310                 315                 320

Ile Lys Glu Ile Val Thr Asn Asp Asp Gly Thr Ile Asn His Leu Leu
                325                 330                 335

Leu Arg Ser Gly Glu Lys Ile Val Ala Asp Glu Tyr Val Ser Ala Met
            340                 345                 350

Pro Val Asp Ile Val Lys Arg Met Leu Pro Thr Thr Trp Gln Thr Met
        355                 360                 365

Pro Tyr Phe Arg Gln Leu Asp Glu Leu Glu Gly Ile Pro Val Ile Asn
    370                 375                 380

Leu His Met Trp Phe Asp Arg Lys Leu Lys Ala Val Asp His Leu Cys
385                 390                 395                 400

Phe Ser Arg Ser Pro Leu Leu Ser Val Tyr Ala Asp Met Ser Val Thr
                405                 410                 415

Cys Lys Glu Tyr Glu Asp Pro Asn Lys Ser Met Leu Glu Leu Val Phe
            420                 425                 430

Ala Pro Cys Ser Pro Ile Ala Gly Gly Asn Val Asn Trp Ile Gly Lys
        435                 440                 445

Ser Asp Glu Glu Ile Ile Asp Ala Thr Met Gly Glu Leu Ala Arg Leu
    450                 455                 460

Phe Pro Thr Glu Ile Ala Asn Asp Asp Lys Trp Pro Ala Thr Lys Met
465                 470                 475                 480

Gln Gly Pro Asn Gly Gln Ala Lys Leu Glu Lys Tyr Ala Val Val Lys
                485                 490                 495

Val Pro Arg Ser Val Tyr Ala Ala Ile Pro Gly Arg Asn Lys Tyr Arg
            500                 505                 510

Pro Ser Gln Thr Ser Pro Ile Pro His Phe Thr Met Ala Gly Cys Tyr
        515                 520                 525

Thr Ser Gln Lys Phe Leu Gly Ser Met Glu Gly Ala Thr Leu Ala Gly
    530                 535                 540

Lys Leu Ala Ala Glu Val Ile Ala Asn Arg Ala Leu Gly Asn Ala Asp
545                 550                 555                 560

Lys Pro Val Lys Glu Ile Gln Gln His Ile Ile Asp Ser Ala Ser Lys
                565                 570                 575

His Val Val Lys Glu Pro Val Gly Val Lys Gly Glu Gly Ala Ile Ala
            580                 585                 590
```

```
Phe Gly Gly Gly Tyr Thr Val Gly Lys Lys Glu Glu Asp Leu Leu Arg
        595                 600                 605

Glu Ser Asp Pro Ala Gln Tyr Glu Leu Ala Val Ala Lys
    610                 615                 620


<210> SEQ ID NO 29
<211> LENGTH: 602
<212> TYPE: PRT
<213> ORGANISM: Thalassiosira pseudonana

<400> SEQUENCE: 29

Met Lys Phe Leu Leu Pro Leu Leu Pro Ala Val Ala Gly Ala Phe Ser
1               5                   10                  15

Ile Thr His Leu Ser Gln His Pro Ser Leu Arg Met His Gln Ser Leu
            20                  25                  30

Ser Thr Ser Leu Tyr Ser Ser Ser Ser Ser Thr Ser Gln Arg Pro Arg
        35                  40                  45

Arg Pro Thr Pro Asp Arg Ile Arg Asn Thr Gln Asn Phe Lys Glu Ala
    50                  55                  60

Lys Glu Leu Ser Gln Lys Phe Ile Thr Asp Phe Gln Gln Leu Gln Lys
65                  70                  75                  80

Val Gly Ser Gly Glu Pro Lys Arg Val Ala Ile Phe Gly Gly Gly Leu
                85                  90                  95

Ser Gly Leu Ser Cys Ala Lys Tyr Leu Ser Asp Ala Gly His Ile Pro
            100                 105                 110

Thr Leu Tyr Glu Ala Arg Gly Val Leu Gly Gly Lys Val Ser Ala Trp
        115                 120                 125

Gln Asp Glu Asp Gly Asp Thr Val Glu Thr Gly Leu His Ile Phe Phe
    130                 135                 140

Gly Ala Tyr Pro Asn Ile His Asn Leu Phe Asp Gly Leu Lys Ile Gln
145                 150                 155                 160

Asp Arg Leu Gln Trp Ala Pro His Arg Met Thr Phe Ala Met Gln Glu
                165                 170                 175

Leu Pro Gly Gln Phe Thr Thr Phe Glu Phe Pro Ala Gly Val Pro Ala
            180                 185                 190

Pro Leu Asn Met Ala Ala Ala Ile Leu Gly Asn Thr Glu Met Leu Thr
        195                 200                 205

Leu Glu Glu Lys Ile Lys Met Val Pro Gly Leu Leu Pro Met Leu Leu
    210                 215                 220

Glu Gly Gln Ser Phe Ile Asp Glu Gln Asp Glu Leu Ser Val Leu Gln
225                 230                 235                 240

Phe Met Arg Lys Tyr Gly Met Pro Glu Arg Ile Asn Glu Glu Ile Phe
                245                 250                 255

Ile Ala Met Gly Lys Ala Leu Asp Phe Ile Asp Pro Asp Leu Leu Ser
            260                 265                 270

Met Thr Val Val Leu Thr Ala Met Asn Arg Phe Ile Asn Glu Ala Asp
        275                 280                 285

Gly Ser Gln Thr Ala Phe Leu Asp Gly Asn Pro Pro Glu Arg Leu Cys
    290                 295                 300

Gln Pro Met Lys Glu Ser Ile Glu Lys Lys Gly Gly Glu Val Val Cys
305                 310                 315                 320

Asn Ser Pro Val Val Glu Ile Gln Leu Asn Glu Glu Ser Asn Val Lys
                325                 330                 335

Ser Leu Lys Leu Ala Asn Gly Thr Glu Ile Thr Ala Asp Tyr Tyr Val
            340                 345                 350
```

```
Ser Ala Val Pro Val Asp Val Phe Lys Arg Leu Val Pro Thr Gln Trp
        355                 360                 365

Ser Thr Met Pro Tyr Phe Arg Gln Leu Asp Glu Leu Glu Gly Ile Pro
    370                 375                 380

Val Ile Asn Ile Gln Ile Trp Phe Asp Arg Lys Leu Asn Ser Val Asp
385                 390                 395                 400

Gly Leu Cys Phe Ser Arg Ser Pro Leu Leu Ser Val Tyr Ala Asp Met
                405                 410                 415

Ser Thr Cys Cys Glu Glu Tyr Ala Ser Asn Asp Lys Ser Met Leu Glu
            420                 425                 430

Leu Val Phe Ala Pro Cys Ser Pro Glu Ala Gly Ser Pro Leu Asn Trp
        435                 440                 445

Ile Ala Lys Pro Asp Ser Asp Ile Ile Asp Ala Thr Met Lys Glu Leu
    450                 455                 460

Glu Arg Leu Phe Pro Leu Glu Ile Gly Pro Asp Ala Pro Glu Glu Lys
465                 470                 475                 480

Arg Ala Asn Val Val Lys Ser Thr Val Val Arg Val Pro Arg Ser Val
                485                 490                 495

Tyr Ala Ala Val Pro Gly Arg Asn Lys Tyr Arg Pro Ser Gln Glu Ser
            500                 505                 510

Pro Ile Glu Asn Phe Ile Met Ala Gly Asp Tyr Ala Thr Gln Lys Tyr
        515                 520                 525

Leu Gly Ser Met Glu Gly Ala Val Leu Ser Gly Lys Leu Ala Ala Glu
    530                 535                 540

Val Ile Cys Asp Lys Phe Met Gly Arg Ala Glu Arg Lys Gly Val Lys
545                 550                 555                 560

Glu Val His Ser Ser Val Leu Thr Lys Gln Ile Glu Glu Arg Thr Pro
                565                 570                 575

Ala Gly Ile Ala Met Glu Lys Gly Arg Val Ser Pro Thr Ser Tyr Gly
            580                 585                 590

Gly Gly Gln Gln Gly Gly Phe Glu Asn Pro
        595                 600


<210> SEQ ID NO 30
<211> LENGTH: 624
<212> TYPE: PRT
<213> ORGANISM: Phaeodactylum tricornutum

<400> SEQUENCE: 30

Met Met Phe His Tyr Lys Thr Gly Ser Ser Trp Phe Leu Leu Leu Ser
1               5                   10                  15

Ala Ser Ile Thr Thr Thr Leu Thr Thr Thr Thr Met Thr Thr Thr His
            20                  25                  30

Ala Phe Ala Pro His Thr Arg Leu Ser Val Pro His Gly Ala Ser Arg
        35                  40                  45

Leu Val Met Lys Asp Phe Pro Lys Pro Asn Leu Glu Asp Thr Asp Asn
    50                  55                  60

Tyr Arg Phe Tyr Arg Asp Leu Ser His Ser Phe Ser Thr Thr Leu Lys
65                  70                  75                  80

Ala Pro Ser Pro Glu Ser Arg Lys Lys Val Ala Ile Ile Gly Gly Gly
                85                  90                  95

Leu Ser Gly Leu Ala Cys Ala Lys Tyr Leu Ala Asp Ala Gly His Gln
            100                 105                 110

Pro Val Val Tyr Glu Ala Arg Asp Val Leu Gly Gly Lys Val Ser Ala
```

-continued

```
        115                 120                 125

Trp Gln Asp Ala Asp Gly Asp Trp Ile Glu Thr Gly Leu His Ile Phe
    130                 135                 140

Phe Gly Ala Tyr Pro Asn Met Met Asn Leu Phe Ala Glu Leu Asp Ile
145                 150                 155                 160

His Asp Arg Leu Gln Trp Lys Val His Lys Met Ile Phe Ala Met Gln
                165                 170                 175

Glu Leu Pro Gly Glu Phe Thr Thr Phe Asp Phe Ile Pro Gly Ile Pro
            180                 185                 190

Ala Pro Phe Asn Phe Gly Leu Ala Ile Leu Met Asn Gln Lys Met Leu
        195                 200                 205

Thr Leu Pro Glu Lys Ile Gln Thr Ala Pro Pro Leu Leu Pro Met Leu
    210                 215                 220

Val Arg Gly Gln Asp Phe Ile Asp Glu Gln Asp Glu Leu Ser Val Leu
225                 230                 235                 240

Asp Phe Met Arg Lys Tyr Gly Met Pro Glu Arg Ile Asn Glu Glu Val
                245                 250                 255

Phe Ile Ser Met Ala Lys Ala Leu Asp Phe Ile Asp Pro Asp Lys Leu
            260                 265                 270

Ser Met Thr Val Val Leu Thr Ala Met Asn Arg Phe Leu Asn Glu Asp
        275                 280                 285

Asn Gly Leu Gln Met Ala Phe Leu Asp Gly Asn Gln Pro Asp Arg Leu
    290                 295                 300

Cys Ala Pro Met Val Glu His Ile Gln Ala Arg Gly Gly Gln Val Asn
305                 310                 315                 320

Leu Asn Ser Pro Val Gln Glu Ile Val Thr Arg Glu Asp Gly Ser Val
                325                 330                 335

Asp Tyr Leu Leu Met Arg Ser Gly Glu Lys Val Val Ala Asp Glu Tyr
            340                 345                 350

Val Ser Ala Met Pro Val Asp Ile Val Lys Arg Met Leu Pro Glu Lys
        355                 360                 365

Trp Gln Thr Met Pro Tyr Phe Arg Gln Phe Asp Glu Leu Glu Gly Ile
    370                 375                 380

Pro Val Ile Asn Leu His Met Trp Phe Asp Arg Lys Leu Lys Ala Val
385                 390                 395                 400

Asp His Leu Cys Phe Ser Arg Ser Pro Leu Leu Ser Val Tyr Ala Asp
                405                 410                 415

Met Ser Val Thr Cys Lys Glu Tyr Tyr Asp Glu Ser Ala Ser Met Leu
            420                 425                 430

Glu Leu Val Phe Ala Pro Cys Ser Pro Leu Ala Gly Gly Asn Val Asn
        435                 440                 445

Trp Ile Ala Lys Thr Asp Glu Glu Ile Ile Asp Ala Thr Met Gly Glu
    450                 455                 460

Leu Ala Arg Leu Phe Pro Thr Glu Ile Ala Ala Asp Pro Thr Trp Pro
465                 470                 475                 480

Ala Thr Lys Asn Gln Gly Pro Asn Gly Glu Ala Lys Leu Arg Lys Tyr
                485                 490                 495

Ala Val Val Lys Val Pro Arg Ser Val Tyr Ala Ala Ile Pro Gly Arg
            500                 505                 510

Asn Lys Tyr Arg Pro Ser Gln Thr Thr Pro Ile Asp Asn Phe Thr Leu
        515                 520                 525

Ala Gly Asp Trp Thr Ser Gln Lys Phe Leu Gly Ser Met Glu Gly Ala
    530                 535                 540
```

```
Val Leu Gly Gly Lys Leu Ala Ala Glu Val Leu Ala Arg Lys Ala Ala
545                 550                 555                 560

Asn Leu Pro Ala Pro Glu Leu Ala Asn Lys Pro Val Arg Asp Glu Ile
                565                 570                 575

Val Gln Lys Ala Gln Thr His Val Ala Arg Pro Pro Ala Gly Val Lys
            580                 585                 590

Gly Gln Gly Ala Ile Ala Phe Gly Gly Gly Ala Val Leu Gly Thr Glu
        595                 600                 605

Asn Lys Ala Leu Leu Arg Asp Val Asp Pro Ser Gln Phe Val Glu Ala
    610                 615                 620


<210> SEQ ID NO 31
<211> LENGTH: 589
<212> TYPE: PRT
<213> ORGANISM: Phaeodactylum tricornutum

<400> SEQUENCE: 31

Met Lys Leu Val Phe Ser Val Ala Val Leu Ser Cys Trp Asn Ala Trp
1               5                   10                  15

Ala Glu Ala Phe Ala Pro Asn Thr Asn Val Pro Phe His Arg Ile Ala
            20                  25                  30

Lys Ala Gln Ser Ser Leu Ser Ile Val Gln Ala Pro Asp Phe Ser Ser
        35                  40                  45

Val Gly Ser His Leu Glu Ala Gln Ala Asn Val Glu Tyr Leu Lys Lys
    50                  55                  60

Leu Ala Arg Pro Asp Lys Pro Leu Gln Val Ile Val Val Gly Gly Gly
65                  70                  75                  80

Leu Ala Gly Leu Ser Thr Ala Lys His Leu Val Asp Ala Gly His Arg
                85                  90                  95

Pro Ile Val Leu Glu Ala Arg Ser Leu Leu Gly Gly Lys Val Ala Ala
            100                 105                 110

Trp Arg Asp Thr Asp Gly Asp Val Thr Glu Thr Gly Leu His Val Phe
        115                 120                 125

Phe Gly Ala Tyr Pro Asn Ala Leu Thr Leu Phe Asp Glu Leu Lys Ile
    130                 135                 140

Ala Asp Arg Leu Gln Trp Lys Pro His Gln Met Leu Phe Ala Lys Pro
145                 150                 155                 160

Gly Arg Pro Thr Arg Glu Phe Ser Val Phe Asp Phe Pro Pro Leu Pro
                165                 170                 175

Ala Pro Leu Asn Ala Ala Val Ala Ile Leu Ser Cys Thr Asp Met Leu
            180                 185                 190

Thr Trp Pro Glu Lys Ile Arg Leu Gly Ile Gly Leu Ile Pro Ala Tyr
        195                 200                 205

Leu Gln Gly Gln Thr Tyr Val Glu Ser Gln Glu His Val Thr Val Gln
    210                 215                 220

Gln Trp Met Glu Gln Arg Gly Ile Pro Gln Ser Val Thr Asp Glu Val
225                 230                 235                 240

Phe Leu Ala Met Ser Lys Ala Leu Gly Phe Ile Gly Pro Glu Gln Leu
                245                 250                 255

Ser Met Gln Cys Val Leu Ile Ala Leu Asn Arg Phe Leu Gln Glu Thr
            260                 265                 270

Asn Gly Ser Arg Ile Ala Phe Leu Asp Gly Ser Pro Thr Glu Arg Leu
        275                 280                 285

Cys Glu Pro Leu Lys Glu Tyr Ile Glu Ala Arg Gly Gly Leu Val Arg
```

```
    290                 295                 300

Thr Asn Val Pro Val Lys Arg Ile Leu Thr Asn Leu Asp Glu Asn Asp
305                 310                 315                 320

Ser Val Ala Gly Leu Leu Leu Lys Gly Gly Glu Val Val Ser Gly Asp
                325                 330                 335

Ala Tyr Val Asn Ala Met Pro Val Asp Ala Leu Lys Lys Leu Thr Pro
            340                 345                 350

Glu Pro Trp Arg Lys Met Glu Tyr Phe Gln Arg Met Gln Lys Leu Arg
        355                 360                 365

Gly Val Pro Val Met Asn Leu His Leu Trp Phe Asp Arg Lys Leu Ser
    370                 375                 380

Thr Val Asp Asn Leu Ile Phe Ser Arg Ser Pro Leu Leu Ser Val Tyr
385                 390                 395                 400

Ala Asp Met Ser Glu Ala Cys Glu Gly Tyr Ala Ser Lys His Val Ser
                405                 410                 415

Met Leu Glu Leu Val Leu Ala Pro Ala Ala Lys Tyr Met Thr Lys Ser
            420                 425                 430

Asp Asp Glu Ile Leu Gln Ala Thr Met Leu Glu Leu Glu Arg Leu Phe
        435                 440                 445

Pro Gln Glu Ile Lys Ala Asp Gly Ser Leu Ala Ala Val Thr Lys Phe
    450                 455                 460

Thr Leu Val Arg Thr Pro Thr Ser Val Tyr Glu Thr Leu Pro Gly Met
465                 470                 475                 480

Glu Ala Ala Arg Pro Thr Gln Lys Ser Pro Ile Ser Asn Phe Phe Cys
                485                 490                 495

Ala Gly Asp Phe Ser Ser Gln Lys Tyr Leu Ala Ser Met Glu Gly Ala
            500                 505                 510

Ile Leu Ser Gly Gln Leu Ala Ala Lys Ala Val Ala Asp Ser Tyr Val
        515                 520                 525

Asn Ala Ala Ser Asn Asp Gln Ser Ala Val Val Ala Pro Pro Arg Gln
    530                 535                 540

Leu Thr Pro Arg Pro Ala Asp Pro Ser Ala Ala Asp Ala His Asp Val
545                 550                 555                 560

Val Pro Asp Arg Thr Met Tyr Val Ala Lys Val Ala Ser His Ile Pro
                565                 570                 575

Ala Ser Val Gln Glu Glu Leu Glu Gly Ala Val Val Val
            580                 585


<210> SEQ ID NO 32
<211> LENGTH: 594
<212> TYPE: PRT
<213> ORGANISM: Aureococcus anophagefferens

<400> SEQUENCE: 32

Met Ser Arg Leu Leu Cys Ile Ala Ala Phe Ala Ala Ala Leu Gln Pro
1               5                   10                  15

Gln Pro Arg Ala Pro Glu Pro Pro Arg Ile Glu Lys Thr Ala Asn Tyr
            20                  25                  30

Lys Ala Ala Ala Glu Ala Ser Ala Arg Leu Ala Gly Glu Leu Lys Ala
        35                  40                  45

Pro Pro Ala Ser Arg Thr Pro Glu Pro Pro Arg Ile Glu Lys Thr Ala
    50                  55                  60

Asn Tyr Lys Ala Ala Ala Glu Ala Ser Ala Arg Leu Ala Gly Glu Leu
65                  70                  75                  80
```

-continued

```
Lys Ala Pro Pro Ala Ser Arg Lys Thr Val Ala Val Val Gly Gly Gly
                85                  90                  95

Leu Ser Gly Leu Ala Cys Gly Lys Tyr Leu Ser Asp Ala Gly His Glu
            100                 105                 110

Ala Thr Val Tyr Glu Ala Arg Asp Val Leu Gly Gly Lys Val Ser Ala
        115                 120                 125

Trp Gln Asp Asp Asp Gly Asp Trp Ile Glu Thr Gly Leu His Val Phe
    130                 135                 140

Phe Gly Ala Tyr Pro Asn Val Leu Asn Leu Phe Lys Glu Leu Asp Ile
145                 150                 155                 160

Arg Asp Arg Leu Gln Trp Lys Ala His Arg Met Ser Phe Ala Met Arg
                165                 170                 175

Glu Arg Pro Gly Glu Phe Thr Ser Phe Glu Phe Pro Glu Gly Val Pro
            180                 185                 190

Ala Pro Leu Asn Met Ala Ala Ala Ile Leu Thr Asn Thr Glu Met Leu
        195                 200                 205

Ser Leu Val Asp Lys Ile Arg Met Val Pro Gly Leu Leu Pro Met Leu
    210                 215                 220

Leu Glu Gly Gln Ser Phe Ile Asp Glu Gln Asp Glu Leu Ser Val Leu
225                 230                 235                 240

Gln Phe Met Lys Lys Tyr Gly Met Pro Asp Thr Ile Asn Glu Glu Ile
                245                 250                 255

Phe Ile Ala Met Gly Lys Ala Leu Asp Phe Ile Asp Pro Asp Lys Leu
            260                 265                 270

Ser Met Thr Val Val Leu Thr Ala Met Asn Arg Phe Ile Asn Glu Ala
        275                 280                 285

Asp Gly Ser Gln Thr Ala Phe Leu Asp Gly Asn Gln Pro Glu Arg Val
    290                 295                 300

Cys Ala Pro Met Ala Asp Arg Ile Arg Asp Ala Gly Gly Asp Val Glu
305                 310                 315                 320

Thr Asp Ala Pro Leu Ala Glu Ile Arg Val Asn Asp Asp Gly Gly Val
                325                 330                 335

Ala Ala Leu Val Leu Lys Asp Gly Arg Glu Val Val Ala Asp Glu Tyr
            340                 345                 350

Val Leu Ala Met Pro Val Asp Val Thr Lys Arg Leu Ile Pro Glu Ala
        355                 360                 365

Trp Ser Thr Met Pro Phe Phe Arg Gln Leu Asn Glu Leu Glu Gly Ile
    370                 375                 380

Pro Val Ile Asn Val Gln Leu Trp Phe Asp Ala Lys Phe Asp Ser Leu
385                 390                 395                 400

Asp Gly Leu Ala Phe Ser Arg Ser Pro Leu Leu Ser Val Tyr Ala Asp
                405                 410                 415

Met Ser Arg Ser Cys Ala Glu Tyr Ala Asp Asp Asp Arg Ser Met Leu
            420                 425                 430

Glu Leu Val Phe Ala Pro Cys Ala Pro Glu Ala Gly Ser Pro Val Asn
        435                 440                 445

Trp Leu Ala Lys Pro Asp Asp Val Val Ala Ala Thr Leu Asp Glu
    450                 455                 460

Leu Lys Gln Leu Phe Pro Ala Asp Met Ala Asp Ala Lys Leu Leu Lys
465                 470                 475                 480

Ser Ala Val Val Arg Thr Pro Arg Ser Val Tyr Ala Ala Ile Pro Gly
                485                 490                 495

Arg Asn Lys Tyr Arg Pro Ser Gln Arg Thr Pro Ile Pro Asn Leu Thr
```

```
            500                 505                 510

Leu Ala Gly Cys Tyr Thr Ser Gln Lys Phe Leu Gly Ser Met Glu Gly
        515                 520                 525

Ala Val Leu Ala Gly Lys Leu Ala Ala Glu Val Val Ala Ala Arg Ala
    530                 535                 540

Val Gly Ala Ala Ala Pro Gly Leu Lys Asp Val Gln Arg Thr Val Val
545                 550                 555                 560

Ala Ala Ala Ala Asp Ala Ala Pro Arg Arg Pro Thr Gly Cys Gly Lys
                565                 570                 575

Gly Asp Ser Ala Ile Ala Tyr Gly Gly Gly Ala Val Leu Ala Ala Arg
            580                 585                 590

Gly Ser


<210> SEQ ID NO 33
<211> LENGTH: 572
<212> TYPE: PRT
<213> ORGANISM: Aureococcus anophagefferens

<400> SEQUENCE: 33

Met Ala Arg Leu Val Cys Leu Ser Leu Ala Ala Val Ala Gly Ala Leu
1               5                   10                  15

Val Gly Ser Arg Ser Arg Leu Pro Ala Pro Ala Ala Arg Ser Ser Arg
            20                  25                  30

Ala Thr Thr Val Met Lys Asp Phe Ala Lys Pro Asn Val Glu Asp Thr
        35                  40                  45

Ile Pro Tyr Arg Glu Ala Ser Thr Leu Ser Asp Arg Phe Pro Asn Glu
    50                  55                  60

Leu Tyr Ala Pro Ala Pro Gln Lys Lys Lys Val Ala Ile Ile Gly Gly
65                  70                  75                  80

Gly Leu Ser Gly Leu Ser Cys Ala Lys Tyr Leu Ser Asp Ala Gly His
                85                  90                  95

Glu Pro Thr Val Tyr Glu Ala Arg Asp Val Leu Gly Gly Lys Val His
            100                 105                 110

Lys Met Val Phe Ala Met Gln Glu Leu Pro Gly Glu Phe Thr Thr Phe
        115                 120                 125

Asp Phe Ile Pro Gly Ile Pro Ala Pro Phe Asn Phe Gly Leu Ala Ile
    130                 135                 140

Leu Leu Asn Gln Lys Met Leu Thr Leu Gly Glu Lys Leu Gln Thr Ala
145                 150                 155                 160

Pro Pro Leu Leu Pro Met Leu Ile Glu Gly Gln Asp Phe Ile Asn Ala
                165                 170                 175

Gln Asp Glu Leu Ser Val Leu Asp Phe Met Arg Lys Tyr Gly Met Pro
            180                 185                 190

Asp Arg Ile Asn Asp Glu Val Phe Ile Ser Met Ala Lys Ala Leu Asp
        195                 200                 205

Phe Ile Asp Pro Asp Lys Leu Ser Met Thr Val Val Leu Thr Ala Met
    210                 215                 220

Asn Arg Phe Leu Asn Glu Asp Asn Gly Leu Gln Met Ala Phe Leu Asp
225                 230                 235                 240

Gly Asn Gln Pro Asp Arg Leu Cys Ala Pro Met Val Glu Ser Val Glu
                245                 250                 255

Lys Lys Gly Gly Arg Val Val Thr Gly Ala Pro Leu Asp Arg Ile Glu
            260                 265                 270

Val Asp Ala Ala Gly Asn Val Asp Lys Leu Val Leu Arg Ser Gly Glu
```

```
        275                 280                 285

Glu Val Val Ala Asp Glu Tyr Val Ser Ala Met Pro Val Asp Val Leu
    290                 295                 300

Lys Arg Met Val Pro Glu Ala Trp Ser Thr Met Pro Tyr Phe Lys Gln
305                 310                 315                 320

Leu Asp Glu Leu Glu Gly Ile Pro Val Ile Asn Leu His Leu Trp Phe
                325                 330                 335

Asp Glu Lys Leu Thr Thr Ile Asp His Leu Cys Phe Ser Arg Ser Pro
            340                 345                 350

Leu Leu Ser Val Tyr Ala Asp Met Ser Thr Thr Cys Lys Glu Tyr Tyr
        355                 360                 365

Asp Glu Asp Lys Ser Met Leu Glu Leu Val Phe Ala Pro Cys Ser Pro
    370                 375                 380

Leu Ala Gly Gly Asp Thr Asn Trp Ile Gly Lys Thr Asp Glu Asp Ile
385                 390                 395                 400

Ile Gln Ala Thr Met Gly Glu Leu Ala Arg Leu Phe Pro Thr Glu Ile
                405                 410                 415

Ala Ala Asp Pro Ala Tyr Pro Gly Thr Met Thr Glu Arg Thr Phe Leu
            420                 425                 430

Gly Glu Lys Gln Ala Gln Leu Thr Gly Gly Ala Lys Leu Arg Lys Ser
        435                 440                 445

Thr Val Val Lys Val Pro Arg Ser Val Tyr Ala Ala Ile Pro Gly Arg
    450                 455                 460

Asn Lys Tyr Arg Pro Ser Gln Lys Thr Pro Ile Pro Asn Phe Ser Leu
465                 470                 475                 480

Cys Gly Cys Phe Thr Ser Gln Lys Phe Leu Gly Ser Met Glu Gly Ala
                485                 490                 495

Ile Leu Ala Gly Lys Leu Ala Ala Glu Val Val Ser Ala Arg Ala Val
            500                 505                 510

Gly Ala Asp Ala Pro Gly Leu Lys Glu Val Gln Gln His Val Ile Asp
        515                 520                 525

Ala Ala Ala Asp Ala Ala Pro Lys Lys Pro Val Gly Cys Arg Gly Asp
    530                 535                 540

Thr Ala Ile Ala Phe Gly Gly Gly Tyr Thr Phe Asp Gln Leu Val Thr
545                 550                 555                 560

Arg Glu Leu Lys Glu Gln Asp Ala Val Gln Phe Asn
                565                 570


<210> SEQ ID NO 34
<211> LENGTH: 594
<212> TYPE: PRT
<213> ORGANISM: Emiliania huxleyi

<400> SEQUENCE: 34

Met Leu Arg Thr Ala Thr Ile Ser Leu Leu Ala Ala Leu Ser Ser Leu
1               5                   10                  15

Leu Ser Val Ala Ala Ala Ala His Ala Pro Arg Pro Pro Thr Pro Ser
            20                  25                  30

Arg Ile Lys Leu Thr Gln Asn Phe Arg Glu Ala Ala Ala Leu Ser Ala
        35                  40                  45

Lys Leu Ala Asp Pro Ala Thr Pro Gln Gln Arg Lys Lys Val Ala Val
    50                  55                  60

Ile Gly Gly Gly Leu Ser Gly Leu Ala Cys Ala Lys Tyr Leu Ser Asp
65                  70                  75                  80
```

```
Ala Gly His Thr Pro Leu Val Leu Glu Ala Arg Asp Val Leu Gly Gly
                85                  90                  95

Lys Val Ser Ala Trp Gln Asp Ala Asp Gly Asp Met Ile Glu Thr Gly
            100                 105                 110

Leu His Ile Phe Phe Gly Ala Tyr Pro Asn Met Met Asn Leu Phe Gln
        115                 120                 125

Glu Leu Gly Ile Glu Asp Arg Leu Gln Trp Lys Ala His Arg Met Thr
    130                 135                 140

Phe Ala Met Pro Gln Leu Pro Gly Glu Phe Thr Ser Phe Asp Phe Pro
145                 150                 155                 160

Asp Gly Val Pro Ala Pro Leu Asn Met Ala Ala Ala Ile Leu Gly Asn
                165                 170                 175

Thr Glu Met Leu Ser Leu Leu Asp Lys Val Arg Met Val Pro Gly Leu
            180                 185                 190

Leu Pro Met Leu Leu Glu Gly Gln Pro Phe Ile Asp Ala Gln Asp Glu
        195                 200                 205

Leu Ser Val Lys Glu Phe Met Asp Lys Tyr Gly Met Pro Glu Thr Val
    210                 215                 220

Asn Glu Glu Ile Phe Ile Ala Met Ala Lys Ala Leu Tyr His Thr Ala
225                 230                 235                 240

His Ser Pro Glu Pro Thr Leu Asp Ser Ala Ala Leu Asp Phe Met Asp
                245                 250                 255

Pro Asp Arg Met Ser Met Ala Val Val Leu Thr Ala Met Asn Arg Phe
            260                 265                 270

Ile Asn Glu Ala Asp Gly Ser Gln Thr Ala Phe Leu Asp Gly Gly Gln
        275                 280                 285

Pro Glu Arg Leu Cys Ala Pro Val Val Asp His Val Leu Ser Arg Gly
    290                 295                 300

Gly Glu Val Arg Leu Gly Ala Pro Leu Ala Ala Ile Glu Val Gly Asp
305                 310                 315                 320

Asp Gly Gln Val Ala Cys Leu Arg Leu Ala Asp Gly Ser Ser Val Glu
                325                 330                 335

Ala Asp Val Tyr Val Ser Ala Val Pro Val Asp Val Phe Lys Lys Leu
            340                 345                 350

Leu Pro Ala Ser Trp Ser Thr Met Pro Phe Phe Arg Gln Thr Glu Glu
        355                 360                 365

Leu Ile Gly Ile Pro Val Ile Asn Val Gln Leu Trp Phe Asp Lys Lys
    370                 375                 380

Leu Arg Ser Val Asp Gly Leu Cys Phe Ser Arg Ser Pro Leu Leu Ser
385                 390                 395                 400

Val Tyr Ala Asp Met Ser Thr Cys Val Glu Glu Tyr Ala Asp Ala Asp
                405                 410                 415

Arg Ser Met Leu Glu Leu Val Phe Ala Pro Ala Thr Arg Glu Val Gly
            420                 425                 430

Ala Asp Arg Asn Trp Ile Gly Ala Ser Asp Ala Glu Val Val Ala Ala
        435                 440                 445

Cys Leu Gly Glu Leu Ser Arg Leu Phe Pro Gly Glu Ile Gly Gly Glu
    450                 455                 460

Gly Gly Ala Glu Leu Leu Lys His Ala Val Val Arg Thr Pro Arg Ser
465                 470                 475                 480

Val Tyr Ala Ala Thr Pro Gly Arg Asn Arg Tyr Arg Pro Ser Gln Ala
                485                 490                 495

Thr Gln Ala Thr Pro Val Pro Asn Phe Val Leu Ala Gly Asp Trp Thr
```

```
            500                 505                 510

Ser Gln Lys Phe Leu Gly Ser Met Glu Gly Ala Val Leu Ala Gly Lys
        515                 520                 525

Leu Ala Ala Glu Val Ile Ala Asp Arg Ala Ala Gly Arg Ala Ala Ala
    530                 535                 540

Thr Ser Gln Thr Leu Lys Pro Val His Glu Glu Val Val Ala Ala Ala
545                 550                 555                 560

Glu Gly Ala Ala Pro Arg Glu Pro Val Gly Val Arg Gly Arg His Pro
                565                 570                 575

Ile Ala Phe Gly Gly Gly Gln Gln Gly Leu Gly Glu Thr Lys Phe Glu
            580                 585                 590

His Ala


<210> SEQ ID NO 35
<211> LENGTH: 633
<212> TYPE: PRT
<213> ORGANISM: Emiliania huxleyi

<400> SEQUENCE: 35

Met Leu Arg Ala Ala Thr Ile Ser Leu Leu Ala Ala Leu Ser Ser Leu
1               5                   10                  15

Leu Ser Val Ala Ala Ala Ala His Ala Pro Arg Pro Pro Thr Pro Ser
            20                  25                  30

Arg Ile Lys Leu Thr Gln Asn Phe Arg Glu Ala Ala Ala Leu Ser Ala
        35                  40                  45

Lys Leu Ala Asp Pro Ala Thr Pro Gln Gln Arg Lys Lys Val Ala Val
    50                  55                  60

Ile Gly Gly Gly Leu Ser Gly Leu Ala Cys Ala Lys Tyr Leu Ser Asp
65                  70                  75                  80

Ala Gly His Thr Pro Leu Val Leu Glu Ala Arg Asp Val Leu Gly Gly
                85                  90                  95

Lys Val Ser Ala Trp Gln Asp Ala Asp Gly Asp Met Ile Glu Thr Gly
            100                 105                 110

Leu His Ile Phe Phe Gly Ala Tyr Pro Asn Met Met Asn Leu Phe Gln
        115                 120                 125

Glu Leu Gly Ile Glu Asp Arg Leu Gln Trp Lys Ala His Arg Met Thr
    130                 135                 140

Phe Ala Met Pro Gln Leu Pro Gly Glu Phe Thr Ser Phe Asp Phe Pro
145                 150                 155                 160

Asp Gly Val Pro Ala Pro Leu Asn Met Ala Ala Ala Ile Leu Gly Asn
                165                 170                 175

Thr Glu Met Leu Ser Leu Leu Asp Lys Val Arg Met Val Pro Gly Leu
            180                 185                 190

Leu Pro Met Leu Leu Glu Gly Gln Pro Phe Ile Asp Ala Gln Asp Glu
        195                 200                 205

Leu Ser Val Lys Glu Phe Met Asp Lys Tyr Gly Met Pro Glu Thr Val
    210                 215                 220

Asn Glu Glu Ile Phe Ile Ala Met Ala Lys Ala Leu Tyr His Thr Ala
225                 230                 235                 240

His Ser Pro Glu Pro Thr Leu Asp Ser Ala Ala Leu Asp Phe Met Asp
                245                 250                 255

Pro Asp Arg Met Ser Met Ala Val Val Leu Thr Ala Met Asn Arg Phe
            260                 265                 270

Ile Asn Glu Ala Asp Gly Ser Gln Ala Arg Ala Cys Thr Ala Phe Leu
```

```
        275                 280                 285

Asp Gly Gly Gln Pro Glu Arg Leu Cys Ala Pro Val Val Asp His Val
    290                 295                 300

Leu Ser Arg Gly Gly Glu Val Arg Leu Gly Ala Pro Leu Ala Ala Ile
305                 310                 315                 320

Glu Val Gly Asp Asp Gly Gln Val Ala Cys Leu Arg Leu Ala Asp Gly
                325                 330                 335

Ser Ser Val Glu Ala Asp Val Tyr Val Ser Ala Val Pro Val Asp Val
            340                 345                 350

Phe Lys Lys Leu Leu Pro Ala Ser Trp Ser Thr Met Pro Phe Phe Arg
        355                 360                 365

Gln Thr Glu Glu Leu Val Gly Ile Pro Val Ile Asn Val Gln Leu Trp
    370                 375                 380

Phe Asp Lys Lys Leu Arg Ser Val Asp Gly Leu Cys Phe Ser Arg Ser
385                 390                 395                 400

Pro Leu Leu Ser Val Tyr Ala Asp Met Ser Thr Cys Val Glu Glu Tyr
                405                 410                 415

Ala Asp Ala Asp Arg Ser Met Leu Glu Leu Val Phe Ala Pro Ala Thr
            420                 425                 430

Arg Glu Val Gly Ala Asp Arg Asn Trp Ile Gly Ala Ser Asp Ala Glu
        435                 440                 445

Val Val Ala Ala Cys Leu Gly Glu Leu Ser Arg Leu Phe Pro Gly Ala
    450                 455                 460

Pro Cys Thr Pro Pro Arg Pro Ala Ala Thr Ala Thr Gly Arg Ala Arg
465                 470                 475                 480

Arg Arg Pro Ser Pro Thr Leu Cys Ser Arg Ala Thr Gly Gln Ala Lys
                485                 490                 495

Ser Ser Ser Ala Arg Trp Arg Gly Arg Cys Trp Arg Ala Ser Ser Arg
            500                 505                 510

Pro Arg Ser Ser Pro Thr Ala Pro Pro Ala Ala Pro Pro Arg Arg Arg
        515                 520                 525

Arg Arg Ser Ser Pro Cys Thr Arg Arg Trp Ser Pro Arg Pro Arg Ala
    530                 535                 540

Pro Pro Arg Ala Ser Gln Trp Ala Cys Ala Gly Gly Thr Gln Leu Pro
545                 550                 555                 560

Leu Ala Ala Gly Ser Arg Ala Trp Glu Arg Arg Ser Leu Ser Thr Arg
                565                 570                 575

Asp Arg Ala Arg Gly Arg Gly Gly Gly Ser Arg His Thr Pro Ala Gly
            580                 585                 590

Pro Gly Pro Gly Arg Gln Gly Pro Gly Arg Ile Leu Ile Arg Val Gln
        595                 600                 605

Gln Ala Trp Leu Ser Ser Thr His Thr Asn Thr His Thr Ser Val Arg
    610                 615                 620

Cys Val Arg Gly Tyr Thr Ser Tyr Asn
625                 630
```

<210> SEQ ID NO 36
<211> LENGTH: 25
<212> TYPE: DNA
<213> ORGANISM: Artificial Sequence
<220> FEATURE:
<223> OTHER INFORMATION: Synthetic nucleotide sequence

<400> SEQUENCE: 36
agattttcac cggttggaag gaggt 25

-continued

```
<210> SEQ ID NO 37
<211> LENGTH: 11
<212> TYPE: DNA
<213> ORGANISM: Artificial Sequence
<220> FEATURE:
<223> OTHER INFORMATION: Synthetic nucleotide sequence

<400> SEQUENCE: 37

cgacttacga a                                                    11
```